(12) United States Patent
Petsko et al.

(10) Patent No.: US 10,533,038 B2
(45) Date of Patent: Jan. 14, 2020

(54) METHODS OF REDUCING TDP-43-MEDIATED NEURONAL CYTOTOXICITY IN AMYOTROPHIC LATERAL SCLEROSIS BY A UPF1 POLYPEPTIDE OR POLYNUCLEOTIDE

(71) Applicant: Brandeis University, Waltham, MA (US)

(72) Inventors: Greg Petsko, New York, NY (US); Dagmar Ringe, Cambridge, MA (US); Shulin Ju, Beavercreek, OH (US)

(73) Assignee: Brandeis University, Waltham, MA (US)

( * ) Notice: Subject to any disclaimer, the term of this patent is extended or adjusted under 35 U.S.C. 154(b) by 0 days.

(21) Appl. No.: 14/434,737

(22) PCT Filed: Oct. 8, 2013

(86) PCT No.: PCT/US2013/063858
§ 371 (c)(1),
(2) Date: Apr. 9, 2015

(87) PCT Pub. No.: WO2014/058866
PCT Pub. Date: Apr. 17, 2014

(65) Prior Publication Data
US 2015/0259391 A1 Sep. 17, 2015

Related U.S. Application Data

(60) Provisional application No. 61/712,322, filed on Oct. 11, 2012.

(51) Int. Cl.
| | |
|---|---|
| *A61K 38/00* | (2006.01) |
| *A61K 49/00* | (2006.01) |
| *A61B 5/00* | (2006.01) |
| *C07K 14/00* | (2006.01) |
| *A61K 48/00* | (2006.01) |
| *C07K 14/475* | (2006.01) |

(Continued)

(52) U.S. Cl.
CPC ........... *C07K 14/47* (2013.01); *A61K 9/0019* (2013.01); *A61K 38/17* (2013.01); *C12Q 1/025* (2013.01); *G01N 33/5058* (2013.01); *A01K 67/0275* (2013.01); *A01K 2207/05* (2013.01); *A01K 2207/10* (2013.01); *A01K 2207/20* (2013.01); *A01K 2217/206* (2013.01); *A01K 2267/03* (2013.01); *A01K 2267/0306* (2013.01); *A01K 2267/0318* (2013.01); *A01K 2267/0393* (2013.01); *A61K 31/7088* (2013.01); *A61K 31/711* (2013.01); *A61K 31/7105* (2013.01); *A61K 31/7115* (2013.01); *A61K 31/7125* (2013.01); *A61K 35/12* (2013.01); *A61K 38/00* (2013.01); *A61K 38/1709* (2013.01); *A61K 48/00* (2013.01); *A61K 48/005* (2013.01); *A61K 48/0066* (2013.01); *A61K 2300/00* (2013.01); *A61P 3/00* (2018.01); *C12N 15/85* (2013.01); *C12Q 1/6883* (2013.01); *C12Q 2600/106* (2013.01); *G01N 33/5023* (2013.01); *G01N 2333/47* (2013.01); *G01N 2500/10* (2013.01); *G01N 2800/56* (2013.01)

(58) Field of Classification Search
CPC ............ A61K 2300/00; A61K 31/7105; A61K 31/713; A61K 2267/0318; A61K 31/00; A61K 38/00; A61K 48/005; A61K 38/17; A61K 48/00; A61K 9/0019; A61K 31/711; A61K 35/30; A61K 2039/5156; A61K 38/1709; A61K 48/0066; A61K 31/7088; A61K 31/7115; A61K 31/7125; A61K 35/12; C12Q 1/6883; C12Q 2600/158; C12Q 2699/118; C12Q 2600/106; C12Q 2600/112; C12Q 2600/118; C07K 14/47; C07K 14/435; C07K 14/00; G01N 33/6896; G01N 2500/10; G01N 33/5058; G01N 2800/2835; G01N 33/5023; G01N 2333/4703; G01N 2333/4706; G01N 2800/56; G01N 2800/52; C12N 15/85; C12N 2510/00; C12N 2800/80; G06F 19/18; A01K 2207/05; A01K 2207/10; A01K 2207/20; A01K 2267/03; A01K 2267/0306; A01K 67/0275; A01K 2217/206; A01K 2227/105; A01K 2267/0318; A01K 2267/0393; A61P 3/00
See application file for complete search history.

(56) References Cited

U.S. PATENT DOCUMENTS

| | | | | |
|---|---|---|---|---|
| 8,486,635 B2 * | 7/2013 | Hutton | ................. | C12Q 1/6809 |
| | | | | 435/6.12 |
| 8,603,814 B2 * | 12/2013 | Pe'ery | ................. | A61K 31/426 |
| | | | | 435/372.3 |

(Continued)

FOREIGN PATENT DOCUMENTS

| | | | | |
|---|---|---|---|---|
| WO | WO98/45322 | * 10/1998 | ............. | C07K 14/00 |

OTHER PUBLICATIONS

Lagier-Tourenne et al. (Cell 2009; 136:1001-1004.*

(Continued)

*Primary Examiner* — Chang-Yu Wang
(74) *Attorney, Agent, or Firm* — Choate, Hall & Stewart LLP; John P. Rearick; Nicholas J. Pace

(57) ABSTRACT

Nonsense-mediated mRNA decay (NMD) polypeptides, nucleic acids encoding NMD polypeptides, and methods of using such polypeptides and nucleic acids in the treatment of ALS and in screening for agents for the treatment of ALS are described.

3 Claims, 1 Drawing Sheet
Specification includes a Sequence Listing.

(51) Int. Cl.
| | |
|---|---|
| A61K 35/12 | (2015.01) |
| C12N 15/00 | (2006.01) |
| C12N 15/09 | (2006.01) |
| C12N 15/10 | (2006.01) |
| C12N 15/12 | (2006.01) |
| C12N 15/13 | (2006.01) |
| C07H 21/04 | (2006.01) |
| C07H 19/00 | (2006.01) |
| C07H 21/00 | (2006.01) |
| C12N 15/11 | (2006.01) |
| C07K 14/48 | (2006.01) |
| C07K 14/47 | (2006.01) |
| A61K 38/17 | (2006.01) |
| G01N 33/50 | (2006.01) |
| A61K 9/00 | (2006.01) |
| C12Q 1/02 | (2006.01) |
| A61K 31/7125 | (2006.01) |
| A61K 31/7088 | (2006.01) |
| A61K 31/711 | (2006.01) |
| A61K 31/7105 | (2006.01) |
| A61K 31/7115 | (2006.01) |
| C12Q 1/6883 | (2018.01) |
| C12N 15/85 | (2006.01) |
| A61P 3/00 | (2006.01) |
| A01K 67/027 | (2006.01) |

(56) References Cited

U.S. PATENT DOCUMENTS

| | | | | |
|---|---|---|---|---|
| 9,271,998 | B2* | 3/2016 | Pe'ery | A61K 31/426 |
| 2003/0032158 | A1 | 2/2003 | Peltz et al. | |
| 2004/0127577 | A1 | 7/2004 | Blaugrund et al. | |
| 2010/0105034 | A1* | 4/2010 | Hutton | C12Q 1/6809 |
| | | | | 435/6.16 |
| 2011/0039911 | A1* | 2/2011 | Pe'ery | A61K 31/426 |
| | | | | 514/44 |
| 2013/0345142 | A1* | 12/2013 | Hutton | C12Q 1/6809 |
| | | | | 514/17.8 |
| 2014/0073685 | A1* | 3/2014 | Pe'ery | A61K 31/426 |
| | | | | 514/44 A |
| 2014/0206637 | A1* | 7/2014 | Pe'ery | A61K 31/7105 |
| | | | | 514/39 |

OTHER PUBLICATIONS

Ju et al. PLoS Biology Apr. 2011; 9: e1001052: 1-17.*
Bruijn et al. Annu. Rev. Neurosci. 2004, 27: 723-49.*
Rothstein Curr. Opin. In Neurobiol. 1996. 6: 679-687.*
Lagier-Tourenne et al. Hum. Mol. Genet. 2010; 19:R46-R64.*
Ju et al. PLoS Biology 2011; 9: 1-17; e1001052.*
Kryndushkin et al. Prion 2011, 4:250-257.*
Lagier-Tourenne et al., Human Mol. Genet. 2010; 19: R46-R64 published online Apr. 15, 2010; doi:10.1093/hmg/ddq137.*
Jackson et al. Gene Ther. 2015; 22:20-18.*
Vaccaro, A. et al., Mutant TDP-43 and FUS Cause Age-Dependent Paralysis and Neurodegeneration in C. elegans, PLoS One, 7(2): e31321 1-10 (2012).
Chen, Y. et al., DNA/RNA helicase gene mutations in a form of juvenile amyotrophic lateral sclerosis (ALS4), American Journal of Human Genetics, 74(6):1128-1135 (2004).
Ilieva, H. et al., Non-cell autonomous toxicity in neurodegenerative disorders: ALS and beyond, The Journal of Cell Biology, 187(6):761-772 (2009).
Kwiatkowski, T.J. et al., Mutations in the FUS/TLS gene on chromosome 16 cause familial amyotrophic lateral sclerosis, Science, 323(5918):1205-1208 (2009).
Maquat, L.E. and Carmichael, G.G., Quality control of mRNA function, Cell, 104(2):173-176 (2001).
Maquat, L.E., Nonsense-mediated mRNA decay in mammals, Journal of Cell Science, 118(9):1773-1776 (2005).
Maruyama, H. et al., Mutations of optineurin in amyotrophic lateral sclerosis, Nature, 465(7295):223-226 (2010).
Nicholson, P. and Mühlemann, O., Cutting the nonsense: the degradation of PTC-containing mRNAs, Biochemical Society Transactions, 38(6):1615-1620 (2010).
Nishimura, A.L. et al., A mutation in the vesicle-trafficking protein VAPB causes late-onset spinal muscular atrophy and amyotrophic lateral sclerosis, American Journal of Human Genetics, 75(5):822-831 (2004).
Rehwinkel, J. et al., Nonsense-mediated mRNA decay factors act in concert to regulate common mRNA targets, RNA, 11(10):1530-1544 (2005).
Rehwinkel, J. et al., Nonsense-mediated mRNA decay: Target genes and functional diversification of effectors, Trends Biochemical Science, 31(11):639-646 (2006).
Rosen, D.R. et al., Mutations in Cu/Zn superoxide dismutase gene are associated with familial amyotrophic lateral sclerosis, Nature, 362(6415):59-62 (1993).
Rothstein, J.D. et al., Current hypotheses for the underlying biology of amyotrophic lateral sclerosis, Annals of Neurology, 65(1):S3-S9 (2009).
Sreedharan, J. et al., TDP-43 mutations in familial and sporadic amyotrophic lateral sclerosis, Science, 319(5870):1668-1672 (2008).
Takahashi, K. and Yamanaka, K., Induction of pluripotent stem cells from mouse embryonic and adult fibroblast cultures by defined factors, Cell, 126(4):663-676 (2006).
Vance, C. et al., Mutations in FUS, an RNA processing protein, cause familial amyotrophic lateral sclerosis type 6, Science, 323(5918):1208-1211 (2009).
Wittkopp, N. et al., Nonsense-mediated mRNA decay effectors are essential for zebrafish embryonic development and survival, Molecular and Cellular Biology, 29(13):3517-3528 (2009).
Author Not Known, ALZFORUM: Networking for a Cure, DC: ALS Treatment Possibilities Presented at SfN, Satellite, 9 pages (Nov. 30, 2011).
International Search Report for PCT/US2013/063858, 4 pages (dated Aug. 19, 2014).
Ju, et al., A Yeast Model of FUS/TLS-Dependent Cytotoxicity, PLoS Biol, 9(4): e1001052, pp. 1-17 (2011).
Written Opinion for PCT/US2013/063858, 7 pages (dated Aug. 19, 2014).
Alaoui-Ismaili, M.H. and Falb, D., Design of second generation therapeutic recombinant bone morphogenetic proteins, Cytokine Growth Factor Rev., 20(5-6): 501-507 (2009).
Barmada, S. J. et al, Amelioration of toxicity in neuronal models of amyotrophic lateral sclerosis by hUPF1, PNAS, 112(25): 7821-7826 (2015).
Burgess, W. H. et al, Possible dissociation of the heparin-binding and mitogenic activities of heparin-binding (acidic fibroblast) growth factor-1 from its receptor-binding activities by site-directed mutagenesis of a single lysine residue, J. Cell Biol., 111: 2129-38 (1990).
Guo, H.H. et al, Protein tolerance to random amino acid change, PNAS, 101(25): 9205-10 (2004).
Pawson, T. and Nash, P., Assembly of cell regulatory systems through protein interaction domains, Science, 300: 445-52 (2003).

* cited by examiner

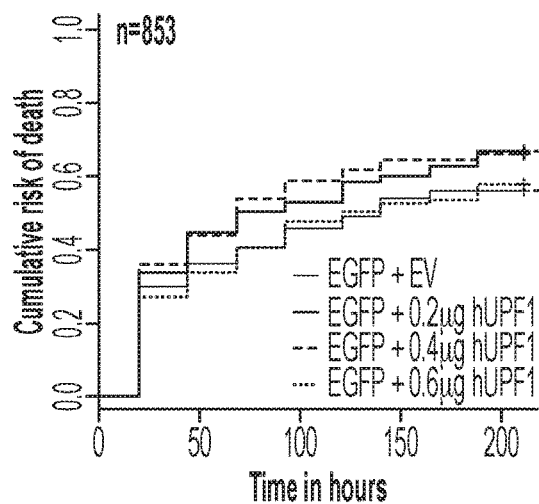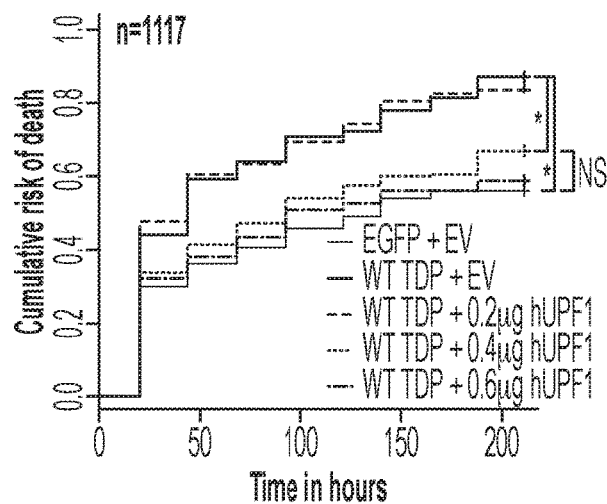

SEQUENCE LISTING

<160> NUMBER OF SEQ ID NOS: 14

<210> SEQ ID NO 1
<211> LENGTH: 3357
<212> TYPE: DNA
<213> ORGANISM: Homo sapiens

<400> SEQUENCE: 1

```
atgagcgtgg aggcgtacgg gcccagctcg cagactctca ctttcctgga cacggaggag      60
gccgagctgc ttggcgccga cacacagggc tccgagttcg agttcaccga ctttactctt     120
cctagccaga cgcagacgcc cccggcggc cccggcggcc cggcggtgg cggcgcggga       180 agcccgggcg cgcgggcgc cggcgctgcg gcgggacagc tcgacgcgca ggttgggccc      240
gaaggcatcc tgcagaacgg gctgtggac gacagtgtag ccaagaccag ccagttgttg      300
gctgagttga acttcgagga agatgaagaa gacacctatt acacgaagga cctccccata     360
cacgcctgca gttactgtgg aatacacgat cctgcctgcg tggtttactg taatacccagc    420 aagaagtggt tctgcaacgg acgtggaaat acttctggca gccacattgt aaatcacctt     480
gtgagggcaa aatgcaaaga ggtgacccctg cacaaggacg ggcccctggg ggagacagtc    540
ctggagtgct acaactgcgg ctgtcgcaac gtcttcctcc tcggcttcat cccggccaaa    600
gctgactcag tggtggtgct gctgtgcagg cagcccgtg ccagcagag cagcctcaag      660 gacatcaact gggacagctc gcagtggcag ccgctgatcc aggaccgctg cttcctgtcc    720
tggctggtca agatcccctc cgagcaggag cagctgcggg cacgccagat acggcacag    780 cagatcaaca agctggagga gctgtggaag gaaaacccctt ctgccacgct ggaggacctg    840
gagaagccgg gggtggacga ggagccgcag catgtcctcc tgcggtacga ggacgcctac    900
cagtaccaga acatattcgg gcccctggtc aagctggagg ccgactacga caagaagctg    960
aaggagtccc agactcaaga taacatcact gtcaggtggg acctgggcct taacaagaag   1020
agaatcgcct acttcactt gcccaagact gactctgaca tgcggctcat gcaggggat    1080 gagatatgcc tgcggtacaa aggggacctt gcgcccctgt ggaaagggat cggccacgtc   1140
atcaaggtcc tgataaatta tggcgatgag atcgccattg agctgcggag cagcgtgggt   1200
```

-continued

```
gcacctgtgg aggtgactca caacttccag gtggattttg tgtggaagtc gacctccttt    1260
gacaggatgc agagcgcatt gaaaacgttt gccgtggatg agacctcggt gtctggctac    1320
atctaccaca agctgttggg ccacgaggtg gaggacgtaa tcaccaagtg ccagctgccc    1380
aagcgcttca cggcgcaggg cctccccgac ctcaaccact cccaggttta tgccgtgaag    1440
actgtgctgc aaagaccact gagcctgatc cagggcccgc caggcacggg gaagacggtg    1500
acgtcggcca ccatcgtcta ccacctggcc cggcaaggca acgggccggt gctggtgtgt    1560
gctccgagca acatcgccgt ggaccagcta acggagaaga tccaccagac ggggctaaag    1620
gtcgtgcgcc tctgcgccaa gagccgtgag gccatcgact ccccggtgtc ttttctggcc    1680
ctgcacaacc agatcaggaa catggacagc atgcctgagc tgcagaagct gcagcagctg    1740
aaagacgaga ctggggagct gtcgtctgcc gacgagaagc ggtaccgggc cttgaagcgc    1800
accgcagaga gagagctgct gatgaacgca gatgtcatct gctgcacatg tgtgggcgcc    1860
ggtgacccga ggctgccaa gatgcagttc cgctccattt taatcgacga aagcacccag    1920
gccaccgagc cggagtgcat ggttcccgtg gtcctcgggg ccaagcagct gatccttgta    1980
ggcgaccact gccagctggg cccagtggtg atgtgcaaga aggcggccaa ggccgggctg    2040
tcacagtcgc tcttcgagcg cctggtggtg ctgggcatcc ggcccatccg cctgcaggtc    2100
cagtaccgga tgcaccctgc actcagcgcc ttcccatcca acatcttcta cgagggctcc    2160
ctccagaatg tgtcactgc agcggatcgt gtgaagaagg gatttgactt ccagtggccc    2220
caacccgata aaccgatgtt cttctacgtg acccagggcc aagaggagat tgccagctcg    2280
ggcacctcct acctgaacag gaccgaggct gcgaacgtgg agaagatcac cacgaagttg    2340
ctgaaggcag gcgccaagcc ggaccagatt ggcatcatca cgccctacga gggccagcgc    2400
tcctacctgg tgcagtacat gcagttcagc ggctccctgc acaccaagct ctaccaggaa    2460
gtggagatcg ccagtgtgga cgcctttcag ggacgcgaga aggacttcat catcctgtcc    2520
tgtgtgcggg ccaacgagca ccaaggcatt ggcttttaa atgaccccag gcgtctgaac    2580
gtggccctga ccagagcaag gtatggcgtc atcattgtgg gcaacccgaa ggcactatca    2640
aagcagccgc tctggaacca cctgctgaac tactataagg agcagaaggt gctggtggag    2700
gggccgctca acaacctgcg tgagagcctc atgcagttca gcaagccacg gaagctggtc    2760
aacactatca acccgggagc ccgcttcatg accacagcca tgtatgatgc ccggaggcc    2820 atcatcccag gctccgtcta tgatcggagc agccagggcc ggccttccag catgtacttc    2880
cagacccatg accagattgg catgatcagt gccggcccta gccacgtggc tgccatgaac    2940
attcccatcc ccttcaacct ggtcatgcca cccatgccac cgcctggcta ttttggacaa    3000
gccaacgggc ctgctgcagg gcgaggcacc ccgaaaggca agactggtcg tggggacgc    3060 cagaagaacc gctttgggct tcctggaccc agccagacta acctcccaa cagccaagcc    3120 agccaggatg tggcgtcaca gcccttctct cagggcgccc tgacgcaggg ctacatctcc    3180
atgagccagc cttcccagat gagccagccc ggcctctccc agccggagct gtcccaggac    3240
agttaccttg gtgacgagtt taaatcacaa atcgacgtgg cgctctcaca ggactccacg    3300
taccagggag agcgggctta ccagcatggc ggggtgacgg ggctgtccca gtattaa       3357
```

<210> SEQ ID NO 2
<211> LENGTH: 1118
<212> TYPE: PRT
<213> ORGANISM: Homo sapiens

<400> SEQUENCE: 2

```
Met Ser Val Glu Ala Tyr Gly Pro Ser Ser Gln Thr Leu Thr Phe Leu
1               5                   10                  15

Asp Thr Glu Glu Ala Glu Leu Leu Gly Ala Asp Thr Gln Gly Ser Glu
            20                  25                  30

Phe Glu Phe Thr Asp Phe Thr Leu Pro Ser Gln Thr Gln Thr Pro Pro
                35                  40                  45

Gly Gly Pro Gly Gly Pro Gly Gly Gly Ala Gly Ser Pro Gly Gly
        50                  55                  60

Ala Gly Ala Gly Ala Ala Ala Gly Gln Leu Asp Ala Gln Val Gly Pro
65                  70                  75                  80

Glu Gly Ile Leu Gln Asn Gly Ala Val Asp Asp Ser Val Ala Lys Thr
                85                  90                  95

Ser Gln Leu Leu Ala Glu Leu Asn Phe Glu Glu Asp Glu Glu Asp Thr
                100                 105                 110

Tyr Tyr Thr Lys Asp Leu Pro Ile His Ala Cys Ser Tyr Cys Gly Ile
            115                 120                 125

His Asp Pro Ala Cys Val Val Tyr Cys Asn Thr Ser Lys Lys Trp Phe
    130                 135                 140

Cys Asn Gly Arg Gly Asn Thr Ser Gly Ser His Ile Val Asn His Leu
145                 150                 155                 160

Val Arg Ala Lys Cys Lys Glu Val Thr Leu His Lys Asp Gly Pro Leu
                165                 170                 175

Gly Glu Thr Val Leu Glu Cys Tyr Asn Cys Gly Cys Arg Asn Val Phe
            180                 185                 190

Leu Leu Gly Phe Ile Pro Ala Lys Ala Asp Ser Val Val Val Leu Leu
        195                 200                 205

Cys Arg Gln Pro Cys Ala Ser Gln Ser Ser Leu Lys Asp Ile Asn Trp
210                 215                 220

Asp Ser Ser Gln Trp Gln Pro Leu Ile Gln Asp Arg Cys Phe Leu Ser
225                 230                 235                 240

Trp Leu Val Lys Ile Pro Ser Glu Gln Glu Gln Leu Arg Ala Arg Gln
                245                 250                 255

Ile Thr Ala Gln Gln Ile Asn Lys Leu Glu Glu Leu Trp Lys Glu Asn
            260                 265                 270

Pro Ser Ala Thr Leu Glu Asp Leu Glu Lys Pro Gly Val Asp Glu Glu
    275                 280                 285

Pro Gln His Val Leu Leu Arg Tyr Glu Asp Ala Tyr Gln Tyr Gln Asn
    290                 295                 300

Ile Phe Gly Pro Leu Val Lys Leu Glu Ala Asp Tyr Asp Lys Lys Leu
305                 310                 315                 320

Lys Glu Ser Gln Thr Gln Asp Asn Ile Thr Val Arg Trp Asp Leu Gly
                325                 330                 335

Leu Asn Lys Lys Arg Ile Ala Tyr Phe Thr Leu Pro Lys Thr Asp Ser
        340                 345                 350

Asp Met Arg Leu Met Gln Gly Asp Glu Ile Cys Leu Arg Tyr Lys Gly
            355                 360                 365

Asp Leu Ala Pro Leu Trp Lys Gly Ile Gly His Val Ile Lys Val Pro
    370                 375                 380

Asp Asn Tyr Gly Asp Glu Ile Ala Ile Glu Leu Arg Ser Ser Val Gly
385                 390                 395                 400

Ala Pro Val Glu Val Thr His Asn Phe Gln Val Asp Phe Val Trp Lys
                405                 410                 415
```

```
Ser Thr Ser Phe Asp Arg Met Gln Ser Ala Leu Lys Thr Phe Ala Val
            420                 425                 430

Asp Glu Thr Ser Val Ser Gly Tyr Ile Tyr His Lys Leu Leu Gly His
        435                 440                 445

Glu Val Glu Asp Val Ile Thr Lys Cys Gln Leu Pro Lys Arg Phe Thr
    450                 455                 460

Ala Gln Gly Leu Pro Asp Leu Asn His Ser Gln Val Tyr Ala Val Lys
465                 470                 475                 480

Thr Val Leu Gln Arg Pro Leu Ser Leu Ile Gln Gly Pro Pro Gly Thr
                485                 490                 495

Gly Lys Thr Val Thr Ser Ala Thr Ile Val Tyr His Leu Ala Arg Gln
            500                 505                 510

Gly Asn Gly Pro Val Leu Val Cys Ala Pro Ser Asn Ile Ala Val Asp
        515                 520                 525

Gln Leu Thr Glu Lys Ile His Gln Thr Gly Leu Lys Val Val Arg Leu
    530                 535                 540

Cys Ala Lys Ser Arg Glu Ala Ile Asp Ser Pro Val Ser Phe Leu Ala
545                 550                 555                 560

Leu His Asn Gln Ile Arg Asn Met Asp Ser Met Pro Glu Leu Gln Lys
                565                 570                 575

Leu Gln Gln Leu Lys Asp Glu Thr Gly Glu Leu Ser Ser Ala Asp Glu
            580                 585                 590

Lys Arg Tyr Arg Ala Leu Lys Arg Thr Ala Glu Arg Glu Leu Leu Met
        595                 600                 605

Asn Ala Asp Val Ile Cys Cys Thr Cys Val Gly Ala Gly Asp Pro Arg
    610                 615                 620

Leu Ala Lys Met Gln Phe Arg Ser Ile Leu Ile Asp Glu Ser Thr Gln
625                 630                 635                 640

Ala Thr Glu Pro Glu Cys Met Val Pro Val Leu Gly Ala Lys Gln
                645                 650                 655

Leu Ile Leu Val Gly Asp His Cys Gln Leu Gly Pro Val Val Met Cys
            660                 665                 670

Lys Lys Ala Ala Lys Ala Gly Leu Ser Gln Ser Leu Phe Glu Arg Leu
        675                 680                 685

Val Val Leu Gly Ile Arg Pro Ile Arg Leu Gln Val Gln Tyr Arg Met
    690                 695                 700

His Pro Ala Leu Ser Ala Phe Pro Ser Asn Ile Phe Tyr Glu Gly Ser
705                 710                 715                 720

Leu Gln Asn Gly Val Thr Ala Ala Asp Arg Val Lys Lys Gly Phe Asp
                725                 730                 735

Phe Gln Trp Pro Gln Pro Asp Lys Pro Met Phe Phe Tyr Val Thr Gln
            740                 745                 750

Gly Gln Glu Glu Ile Ala Ser Ser Gly Thr Ser Tyr Leu Asn Arg Thr
        755                 760                 765

Glu Ala Ala Asn Val Glu Lys Ile Thr Thr Lys Leu Leu Lys Ala Gly
    770                 775                 780

Ala Lys Pro Asp Gln Ile Gly Ile Ile Thr Pro Tyr Glu Gly Gln Arg
785                 790                 795                 800

Ser Tyr Leu Val Gln Tyr Met Gln Phe Ser Gly Ser Leu His Thr Lys
                805                 810                 815

Leu Tyr Gln Glu Val Glu Ile Ala Ser Val Asp Ala Phe Gln Gly Arg
            820                 825                 830

Glu Lys Asp Phe Ile Ile Leu Ser Cys Val Arg Ala Asn Glu His Gln
```

```
                835                 840                 845
Gly Ile Gly Phe Leu Asn Asp Pro Arg Arg Leu Asn Val Ala Leu Thr
        850                 855                 860
Arg Ala Arg Tyr Gly Val Ile Val Gly Asn Pro Lys Ala Leu Ser
865                 870                 875                 880
Lys Gln Pro Leu Trp Asn His Leu Leu Asn Tyr Tyr Lys Glu Gln Lys
                885                 890                 895
Val Leu Val Glu Gly Pro Leu Asn Asn Leu Arg Glu Ser Leu Met Gln
            900                 905                 910
Phe Ser Lys Pro Arg Lys Leu Val Asn Thr Ile Asn Pro Gly Ala Arg
        915                 920                 925
Phe Met Thr Thr Ala Met Tyr Asp Ala Arg Glu Ala Ile Ile Pro Gly
    930                 935                 940
Ser Val Tyr Asp Arg Ser Ser Gln Gly Arg Pro Ser Ser Met Tyr Phe
945                 950                 955                 960
Gln Thr His Asp Gln Ile Gly Met Ile Ser Ala Gly Pro Ser His Val
                965                 970                 975
Ala Ala Met Asn Ile Pro Ile Pro Phe Asn Leu Val Met Pro Pro Met
            980                 985                 990
Pro Pro Pro Gly Tyr Phe Gly Gln Ala Asn Gly Pro Ala Ala Gly Arg
        995                 1000                1005
Gly Thr Pro Lys Gly Lys Thr Gly Arg Gly Gly Arg Gln Lys Asn
    1010                1015                1020
Arg Phe Gly Leu Pro Gly Pro Ser Gln Thr Asn Leu Pro Asn Ser
    1025                1030                1035
Gln Ala Ser Gln Asp Val Ala Ser Gln Pro Phe Ser Gln Gly Ala
    1040                1045                1050
Leu Thr Gln Gly Tyr Ile Ser Met Ser Gln Pro Ser Gln Met Ser
    1055                1060                1065
Gln Pro Gly Leu Ser Gln Pro Glu Leu Ser Gln Asp Ser Tyr Leu
    1070                1075                1080
Gly Asp Glu Phe Lys Ser Gln Ile Asp Val Ala Leu Ser Gln Asp
    1085                1090                1095
Ser Thr Tyr Gln Gly Glu Arg Ala Tyr Gln His Gly Val Thr
    1100                1105                1110
Gly Leu Ser Gln Tyr
    1115

<210> SEQ ID NO 3
<211> LENGTH: 3819
<212> TYPE: DNA
<213> ORGANISM: Homo sapiens

<400> SEQUENCE: 3
atgccagctg agcgtaaaaa gccagcaagt atggaagaaa aagactcttt accaaacaac      60
aaggaaaaag actgcagtga aaggcggaca gtgagcagca ggagaggcc aaaagacgat     120 atcaagctca ctgccaagaa ggaggtcagc aaggcccctg aagacaagaa gaagagactg     180
gaagatgata gagaaaaaaa ggaagacaag gaacgcaaga aaaagacgga agaaaaggtg     240
aaggcagagg aagaatcaaa gaaaaagaa gaggaagaaa aaagaaaca tcaagaggaa     300 gagagaaaga agcaagaaga gcaggccaaa cgtcagcaag aagaagagc agctgctcag     360 atgaaagaaa aagaagaatc cattcagctt catcaggaag cttgggaacg acatcattta     420
agaaaggaac ttcgtagcaa aaaccaaaat gctccggaca gccgaccaga ggaaaacttc     480
```

```
ttcagccgcc tcgactcaag tttgaagaaa aatactgctt ttgtcaagaa actaaaaact      540
attacagaac aacagagaga ctccttgtcc catgatttta atggcctaaa tttaagcaaa      600
tacattgcag aagctgtagc ttccatcgtg gaagcaaaac taaaaatctc tgatgtgaac      660
tgtgctgtgc acctctgctc tctctttcac cagcgttatg ctgactttgc cccatcactt      720
cttcaggtct ggaaaaaaca ttttgaagca aggaaagagg agaaaacacc taacatcacc      780
aagttaagaa ctgatttgcg ttttattgca gaattgacaa tagttgggat tttcactgac      840
aaggaaggtc tttccttaat ctatgaacag ctaaaaaata ttattaatgc tgatcgggag      900
tcccacactc atgtctctgt agtgattagt ttctgtcgac attgtggaga tgatattgct      960
ggacttgtac caaggaaagt aaagagtgct gcagagaagt taatttgag ttttcctcct      1020 agtgagataa ttagtccaga gaaacaacag cccttccaga atcttttaaa agagtacttt      1080
acgtctttga ccaaacacct gaaaagggac cacagggagc tccagaatac tgagagacaa      1140
aacaggcgca ttctacattc taaaggggag ctcagtgaag atagacataa acagtatgag      1200
gaatttgcta tgtcttacca gaagctgctg gcaaattctc aatccttagc agaccttttg      1260
gatgaaaata tgccagatct tcctcaagac aaacccacac cagaagaaca tgggcctgga      1320
attgatatat tcacacctgg taaacctgga gaatatgact tggaaggtgg tatatgggaa      1380
gatgaagatg ctcggaattt ttatgagaac ctcattgatt tgaaggcttt tgtcccagcc      1440
atcttgttta aagacaatga aaaagttgt cagaataaag agtccaacaa agatgatacc      1500
aaagaggcaa aagaatctaa ggagaataag gaggtatcaa gtcccgatga tttggaactt      1560
gagttggaga atctagaaat taatgatgac accttagaat tagaggtgg agatgaagct      1620 gaagatctta caaagaaact tcttgatgaa caagaacaag aagatgagga agccagcact      1680
ggatctcatc tcaagctcat agtagatgct ttcctacagc agttacccaa ctgtgtcaac      1740
cgagatctga tagacaaggc agcaatggat ttttgcatga acatgaacac aaaagcaaac      1800
aggaagaagt tggtacgggc actcttcata gttcctagac aaaggttgga tttgctacca      1860
ttttatgcaa gattggttgc tacattgcat ccctgcatgt ctgatgtagc agaggatctt      1920
tgttccatgc tgaggggga tttcagattt catgtacgga aaaaggacca gatcaatatt      1980
gaaacaaaga ataaaactgt tcgttttata ggagaactaa ctaagtttaa gatgttcacc      2040
aaaaatgaca cactgcattg tttaaagatg cttctgtcag acttctctca tcaccatatt      2100
gaaatggcat gcaccctgct ggagacatgt ggacggtttc ttttcagatc tccagaatct      2160
cacctgagga ccagtgtact tttggagcaa atgatgagaa agaagcaagc aatgcatctt      2220
gatgcgagat acgtcacaat ggtagagaat gcatattact actgcaaccc acctccagct      2280 gaaaaaccg tgaaaagaa acgtcctcct ctccaggaat atgtccggaa acttttgtac      2340
aaagatctct ctaaggttac caccgagaag gttttgagac agatgcgaaa gctgccctgg      2400
caggaccaag aagtgaaaga ctatgttatt tgttgtatga taaacatctg gaatgtgaaa      2460
tataatagta ttcattgtgt agccaacctc ttagcaggac tagtgctcta ccaagaggat      2520
gttgggatcc acgttgtgga tggagtgtta gaagatattc gattaggaat ggaggttaat      2580
caacctaaat ttaatcagag gcgcatcagc agtgccaagt tcttaggaga actttacaat      2640
taccgaatgg tggaatcagc tgttattttc agaactctgt attcttttac ctcatttggt      2700
gttaatcctg atggctctcc aagttccctg gacccacctg agcatctttt cagaattaga      2760
ctcgtatgca ctattctgga cacatgtggc cagtactttg acagaggttc cagtaaacga      2820
```

-continued

```
aaacttgatt gtttccttgt atattttcag cgttatgttt ggtggaagaa aagtttggag    2880
gtttggacaa aagaccatcc atttcctatt gatatagatt acatgatcag tgatacacta    2940
gaactgctaa gaccaaagat caaactctgt aattctctgg aagaatccat caggcaggta    3000
caagacttgg aacgagaatt cttaataaaa ctaggcctag taaatgacaa agactcaaaa    3060
gattctatga cagaaggaga aaatcttgaa gaggatgaag aagaagaaga aggtggggct    3120
gaaacagaag aacaatctgg aaatgaaagt gaagtaaatg agccagaaga gaggagggt    3180 tctgataatg atgatgatga gggagaagaa gaggaggaag agaatacaga ttaccttaca    3240
gattccaata aggaaaatga aaccgatgaa gagaatactg aggtaatgat taaaggcggt    3300
ggacttaagc atgtaccttg tgtagaagat gaggacttca ttcaagctct ggataaaatg    3360
atgctagaaa atctcacagca acgaagtggt gaatctgtta aagtgcacca actagatgtg    3420
gccattcctt tgcatctcaa aagccagctg aggaaagggc ccccactggg aggtggggaa    3480
ggagaggctg agtctgcaga cacaatgccg tttgtcatgt taacaagaaa aggcaataaa    3540
cagcagttta agatccttaa tgtacccatg tcctctcaac ttgctgcaaa tcactggaac    3600
cagcaacagg cagaacaaga agagaggatg agaatgaaga agctcacact agatatcaat    3660
gaacggcaag aacaagaaga ttatcaagaa atgttgcagt ctcttgcaca gcgcccagct    3720
ccagcaaaca ccaatcgtga gaggcggcct cgctaccaac atccgaaggg agcacctaat    3780
gcagatctaa tctttaagac tggtgggagg agacgttga                          3819
```

<210> SEQ ID NO 4
<211> LENGTH: 1272
<212> TYPE: PRT
<213> ORGANISM: Homo sapiens

<400> SEQUENCE: 4

```
Met Pro Ala Glu Arg Lys Lys Pro Ala Ser Met Glu Glu Lys Asp Ser
1               5                  10                  15

Leu Pro Asn Asn Lys Glu Lys Asp Cys Ser Glu Arg Arg Thr Val Ser
            20                  25                  30

Ser Lys Glu Arg Pro Lys Asp Asp Ile Lys Leu Thr Ala Lys Lys Glu
        35                  40                  45

Val Ser Lys Ala Pro Glu Asp Lys Lys Arg Leu Glu Asp Asp Lys
    50                  55                  60

Arg Lys Lys Glu Asp Lys Glu Arg Lys Lys Asp Glu Glu Lys Val
65                  70                  75                  80

Lys Ala Glu Glu Glu Ser Lys Lys Glu Glu Glu Glu Lys Lys Lys
                85                  90                  95

His Gln Glu Glu Glu Arg Lys Lys Gln Glu Glu Gln Ala Lys Arg Gln
            100                 105                 110

Gln Glu Glu Glu Ala Ala Ala Gln Met Lys Glu Lys Glu Glu Ser Ile
        115                 120                 125

Gln Leu His Gln Glu Ala Trp Glu Arg His His Leu Arg Lys Glu Leu
    130                 135                 140

Arg Ser Lys Asn Gln Asn Ala Pro Asp Ser Arg Pro Glu Glu Asn Phe
145                 150                 155                 160

Phe Ser Arg Leu Asp Ser Ser Leu Lys Lys Asn Thr Ala Phe Val Lys
                165                 170                 175

Lys Leu Lys Thr Ile Thr Glu Gln Gln Arg Asp Ser Leu Ser His Asp
            180                 185                 190

Phe Asn Gly Leu Asn Leu Ser Lys Tyr Ile Ala Glu Ala Val Ala Ser
```

```
                195                 200                 205
Ile Val Glu Ala Lys Leu Lys Ile Ser Asp Val Asn Cys Ala Val His
    210                 215                 220

Leu Cys Ser Leu Phe His Gln Arg Tyr Ala Asp Phe Ala Pro Ser Leu
225                 230                 235                 240

Leu Gln Val Trp Lys Lys His Phe Glu Ala Arg Lys Glu Glu Lys Thr
                245                 250                 255

Pro Asn Ile Thr Lys Leu Arg Thr Asp Leu Arg Phe Ile Ala Glu Leu
            260                 265                 270

Thr Ile Val Gly Ile Phe Thr Asp Lys Glu Gly Leu Ser Leu Ile Tyr
        275                 280                 285

Glu Gln Leu Lys Asn Ile Ile Asn Ala Asp Arg Glu Ser His Thr His
    290                 295                 300

Val Ser Val Val Ile Ser Phe Cys Arg His Cys Gly Asp Asp Ile Ala
305                 310                 315                 320

Gly Leu Val Pro Arg Lys Val Lys Ser Ala Ala Glu Lys Phe Asn Leu
                325                 330                 335

Ser Phe Pro Pro Ser Glu Ile Ile Ser Pro Glu Lys Gln Gln Pro Phe
            340                 345                 350

Gln Asn Leu Leu Lys Glu Tyr Phe Thr Ser Leu Thr Lys His Leu Lys
        355                 360                 365

Arg Asp His Arg Glu Leu Gln Asn Thr Glu Arg Gln Asn Arg Arg Ile
    370                 375                 380

Leu His Ser Lys Gly Glu Leu Ser Glu Asp Arg His Lys Gln Tyr Glu
385                 390                 395                 400

Glu Phe Ala Met Ser Tyr Gln Lys Leu Leu Ala Asn Ser Gln Ser Leu
                405                 410                 415

Ala Asp Leu Leu Asp Glu Asn Met Pro Asp Leu Pro Gln Asp Lys Pro
            420                 425                 430

Thr Pro Glu Glu His Gly Pro Gly Ile Asp Ile Phe Thr Pro Gly Lys
        435                 440                 445

Pro Gly Glu Tyr Asp Leu Glu Gly Gly Ile Trp Glu Asp Glu Asp Ala
    450                 455                 460

Arg Asn Phe Tyr Glu Asn Leu Ile Asp Leu Lys Ala Phe Val Pro Ala
465                 470                 475                 480

Ile Leu Phe Lys Asp Asn Glu Lys Ser Cys Gln Asn Lys Glu Ser Asn
                485                 490                 495

Lys Asp Asp Thr Lys Glu Ala Lys Glu Ser Lys Glu Asn Lys Glu Val
            500                 505                 510

Ser Ser Pro Asp Asp Leu Glu Leu Glu Leu Glu Asn Leu Glu Ile Asn
        515                 520                 525

Asp Asp Thr Leu Glu Leu Gly Gly Asp Glu Ala Glu Asp Leu Thr
    530                 535                 540

Lys Lys Leu Leu Asp Glu Gln Glu Gln Glu Asp Glu Glu Ala Ser Thr
545                 550                 555                 560

Gly Ser His Leu Lys Leu Ile Val Asp Ala Phe Leu Gln Gln Leu Pro
                565                 570                 575

Asn Cys Val Asn Arg Asp Leu Ile Asp Lys Ala Ala Met Asp Phe Cys
            580                 585                 590

Met Asn Met Asn Thr Lys Ala Asn Arg Lys Lys Leu Val Arg Ala Leu
        595                 600                 605

Phe Ile Val Pro Arg Gln Arg Leu Asp Leu Leu Pro Phe Tyr Ala Arg
    610                 615                 620
```

```
Leu Val Ala Thr Leu His Pro Cys Met Ser Asp Val Ala Glu Asp Leu
625                 630                 635                 640

Cys Ser Met Leu Arg Gly Asp Phe Arg Phe His Val Arg Lys Lys Asp
            645                 650                 655

Gln Ile Asn Ile Glu Thr Lys Asn Lys Thr Val Arg Phe Ile Gly Glu
                660                 665                 670

Leu Thr Lys Phe Lys Met Phe Thr Lys Asn Asp Thr Leu His Cys Leu
        675                 680                 685

Lys Met Leu Leu Ser Asp Phe Ser His His Ile Glu Met Ala Cys
690                 695                 700

Thr Leu Leu Glu Thr Cys Gly Arg Phe Leu Phe Arg Ser Pro Glu Ser
705                 710                 715                 720

His Leu Arg Thr Ser Val Leu Leu Glu Gln Met Met Arg Lys Lys Gln
            725                 730                 735

Ala Met His Leu Asp Ala Arg Tyr Val Thr Met Val Glu Asn Ala Tyr
                740                 745                 750

Tyr Tyr Cys Asn Pro Pro Ala Glu Lys Thr Val Lys Lys Arg
        755                 760                 765

Pro Pro Leu Gln Glu Tyr Val Arg Lys Leu Leu Tyr Lys Asp Leu Ser
770                 775                 780

Lys Val Thr Thr Glu Lys Val Leu Arg Gln Met Arg Lys Leu Pro Trp
785                 790                 795                 800

Gln Asp Gln Glu Val Lys Asp Tyr Val Ile Cys Cys Met Ile Asn Ile
            805                 810                 815

Trp Asn Val Lys Tyr Asn Ser Ile His Cys Val Ala Asn Leu Leu Ala
                820                 825                 830

Gly Leu Val Leu Tyr Gln Glu Asp Val Gly Ile His Val Val Asp Gly
        835                 840                 845

Val Leu Glu Asp Ile Arg Leu Gly Met Glu Val Asn Gln Pro Lys Phe
850                 855                 860

Asn Gln Arg Arg Ile Ser Ser Ala Lys Phe Leu Gly Glu Leu Tyr Asn
865                 870                 875                 880

Tyr Arg Met Val Glu Ser Ala Val Ile Phe Arg Thr Leu Tyr Ser Phe
            885                 890                 895

Thr Ser Phe Gly Val Asn Pro Asp Gly Ser Pro Ser Ser Leu Asp Pro
                900                 905                 910

Pro Glu His Leu Phe Arg Ile Arg Leu Val Cys Thr Ile Leu Asp Thr
        915                 920                 925

Cys Gly Gln Tyr Phe Asp Arg Gly Ser Ser Lys Arg Lys Leu Asp Cys
930                 935                 940

Phe Leu Val Tyr Phe Gln Arg Tyr Val Trp Trp Lys Lys Ser Leu Glu
945                 950                 955                 960

Val Trp Thr Lys Asp His Pro Phe Pro Ile Asp Ile Asp Tyr Met Ile
            965                 970                 975

Ser Asp Thr Leu Glu Leu Leu Arg Pro Lys Ile Lys Leu Cys Asn Ser
                980                 985                 990

Leu Glu Glu Ser Ile Arg Gln Val Gln Asp Leu Glu Arg Glu Phe Leu
        995                 1000                1005

Ile Lys Leu Gly Leu Val Asn Asp Lys Asp Ser Lys Asp Ser Met
    1010                1015                1020

Thr Glu Gly Glu Asn Leu Glu Glu Asp Glu Glu Glu Glu Gly
    1025                1030                1035
```

Gly Ala Glu Thr Glu Glu Gln Ser Gly Asn Glu Ser Glu Val Asn
    1040                1045                1050

Glu Pro Glu Glu Glu Gly Ser Asp Asn Asp Asp Asp Glu Gly
    1055                1060                1065

Glu Glu Glu Glu Glu Glu Asn Thr Asp Tyr Leu Thr Asp Ser Asn
    1070                1075                1080

Lys Glu Asn Glu Thr Asp Glu Glu Asn Thr Glu Val Met Ile Lys
    1085                1090                1095

Gly Gly Gly Leu Lys His Val Pro Cys Val Glu Asp Glu Asp Phe
    1100                1105                1110

Ile Gln Ala Leu Asp Lys Met Met Leu Glu Asn Leu Gln Gln Arg
    1115                1120                1125

Ser Gly Glu Ser Val Lys Val His Gln Leu Asp Val Ala Ile Pro
    1130                1135                1140

Leu His Leu Lys Ser Gln Leu Arg Lys Gly Pro Pro Leu Gly Gly
    1145                1150                1155

Gly Glu Gly Glu Ala Glu Ser Ala Asp Thr Met Pro Phe Val Met
    1160                1165                1170

Leu Thr Arg Lys Gly Asn Lys Gln Gln Phe Lys Ile Leu Asn Val
    1175                1180                1185

Pro Met Ser Ser Gln Leu Ala Ala Asn His Trp Asn Gln Gln Gln
    1190                1195                1200

Ala Glu Gln Glu Glu Arg Met Arg Met Lys Lys Leu Thr Leu Asp
    1205                1210                1215

Ile Asn Glu Arg Gln Glu Gln Glu Asp Tyr Gln Glu Met Leu Gln
    1220                1225                1230

Ser Leu Ala Gln Arg Pro Ala Pro Ala Asn Thr Asn Arg Glu Arg
    1235                1240                1245

Arg Pro Arg Tyr Gln His Pro Lys Gly Ala Pro Asn Ala Asp Leu
    1250                1255                1260

Ile Phe Lys Thr Gly Gly Arg Arg
    1265                1270

<210> SEQ ID NO 5
<211> LENGTH: 1359
<212> TYPE: DNA
<213> ORGANISM: Homo sapiens

<400> SEQUENCE: 5
atgctgtcgg ccctagaagt gcagttccac cgcgactcgc agcagcagga ggctgagacg    60
ccgccaactt cgtcctccgg ttgcgggggc ggtgcgggca aacctcgcga ggagaagagg   120
acggccctga gcaaggtggt catccgccgc ctgcctccgg gcctcaccaa ggagcagctg   180
gaggagcagc tgcgcccgct gccagcacac gactacttcg agttcttcgc cgccgacctg   240
agtctttatc ctcatctcta ctcaagagca tacattaatt ttaggaatcc tgatgacatc   300
cttcttttta gagatcgttt tgatggatat atcttccttg acagcaaagg cctagaatat   360
cctgcagtgg tagagtttgc tccattccag aagatagcca aaaagaagct gagaaaaaaa   420
gatgccaaga ctggaagcat cgaagatgat ccagaatata gaagtttttt agaaacctac   480
tgtgtggagg aagagaagac cagtgccaac cctgagactc tgctggggga gatggaggcg   540
aagacaagag agctcattgc tagaagaacc acacctcttt tggaatatat taaaaataga   600
aaattagaaa agcagagaat tcgagaagag aagcgagaag aacggaggag gagagagtta   660
gaaaagaaac gtttgcggga gaggaaaaaa gaagaagaa gagaagaaga aagatgcaaa   720

```
aaaaaagaga cagataaaca gaagaaaatt gcagagaaag aagtaaggat taagcttctt      780
aagaaaccag aaaagggaga ggaaccaacc acagagaaac caaagaaag aggagaggag       840 attgatactg gaggtggcaa gcaggaatcc tgtgcccccg gtgcagtcgt aaaagccagg      900
cccatggaag gctcgctgga ggagccccag gagacgtcac acagcggcag tgataaagag      960
cacagggatg tggagagatc tcaagaacaa gaatctgaag cacaaagata ccatgtggat     1020
gacggcagga ggcacagagc tcaccacgag cctgaacggc tttccagaag gagtgaggat     1080
gagcagagat gggggaaagg acctggccaa gacagaggga agaaggggag ccaggacagc     1140
ggggctccgg gggaggccat ggagagactg gaagagcgc aaaggtgtga cgacagtcca      1200
gcacccagaa aagagcgact ggcaaacaag gaccggccag ccttgcagct gtatgatcca     1260
ggagctcgct tccgagcgcg agagtgtggc ggaaacagga ggatctgcaa ggcagaaggt     1320
tcggggactg gtcctgagaa gagggaagag gcagagtga                            1359
```

<210> SEQ ID NO 6
<211> LENGTH: 452
<212> TYPE: PRT
<213> ORGANISM: Homo sapiens

<400> SEQUENCE: 6

```
Met Leu Ser Ala Leu Glu Val Gln Phe His Arg Asp Ser Gln Gln Gln
1               5                   10                  15

Glu Ala Glu Thr Pro Pro Thr Ser Ser Ser Gly Cys Gly Gly Gly Ala
            20                  25                  30

Gly Lys Pro Arg Glu Glu Lys Arg Thr Ala Leu Ser Lys Val Val Ile
        35                  40                  45

Arg Arg Leu Pro Pro Gly Leu Thr Lys Glu Gln Leu Glu Glu Gln Leu
    50                  55                  60

Arg Pro Leu Pro Ala His Asp Tyr Phe Glu Phe Phe Ala Ala Asp Leu
65                  70                  75                  80

Ser Leu Tyr Pro His Leu Tyr Ser Arg Ala Tyr Ile Asn Phe Arg Asn
                85                  90                  95

Pro Asp Asp Ile Leu Leu Phe Arg Asp Arg Phe Asp Gly Tyr Ile Phe
            100                 105                 110

Leu Asp Ser Lys Gly Leu Glu Tyr Pro Ala Val Val Glu Phe Ala Pro
        115                 120                 125

Phe Gln Lys Ile Ala Lys Lys Lys Leu Arg Lys Lys Asp Ala Lys Thr
    130                 135                 140

Gly Ser Ile Glu Asp Asp Pro Glu Tyr Lys Lys Phe Leu Glu Thr Tyr
145                 150                 155                 160

Cys Val Glu Glu Glu Lys Thr Ser Ala Asn Pro Glu Thr Leu Leu Gly
                165                 170                 175

Glu Met Glu Ala Lys Thr Arg Glu Leu Ile Ala Arg Arg Thr Thr Pro
            180                 185                 190

Leu Leu Glu Tyr Ile Lys Asn Arg Lys Leu Glu Lys Gln Arg Ile Arg
        195                 200                 205

Glu Glu Lys Arg Glu Glu Arg Arg Arg Arg Glu Leu Glu Lys Lys Arg
    210                 215                 220

Leu Arg Glu Glu Glu Lys Arg Arg Arg Arg Glu Glu Glu Arg Cys Lys
225                 230                 235                 240

Lys Lys Glu Thr Asp Lys Gln Lys Lys Ile Ala Glu Lys Glu Val Arg
                245                 250                 255
```

```
Ile Lys Leu Leu Lys Lys Pro Glu Lys Gly Glu Pro Thr Glu
        260                 265                 270
Lys Pro Lys Glu Arg Gly Glu Ile Asp Thr Gly Gly Lys Gln
        275                 280                 285
Glu Ser Cys Ala Pro Gly Ala Val Val Lys Ala Arg Pro Met Glu Gly
        290                 295                 300
Ser Leu Glu Glu Pro Gln Glu Thr Ser His Ser Gly Ser Asp Lys Glu
305                 310                 315                 320
His Arg Asp Val Glu Arg Ser Gln Glu Gln Ser Glu Ala Gln Arg
                325                 330                 335
Tyr His Val Asp Asp Gly Arg Arg His Arg Ala His His Glu Pro Glu
                340                 345                 350
Arg Leu Ser Arg Arg Ser Glu Asp Glu Gln Arg Trp Gly Lys Gly Pro
                355                 360                 365
Gly Gln Asp Arg Gly Lys Lys Gly Ser Gln Asp Ser Gly Ala Pro Gly
        370                 375                 380
Glu Ala Met Glu Arg Leu Gly Arg Ala Gln Arg Cys Asp Asp Ser Pro
385                 390                 395                 400
Ala Pro Arg Lys Glu Arg Leu Ala Asn Lys Asp Arg Pro Ala Leu Gln
                405                 410                 415
Leu Tyr Asp Pro Gly Ala Arg Phe Arg Ala Arg Glu Cys Gly Gly Asn
                420                 425                 430
Arg Arg Ile Cys Lys Ala Glu Gly Ser Gly Thr Gly Pro Glu Lys Arg
        435                 440                 445
Glu Glu Ala Glu
    450

<210> SEQ ID NO 7
<211> LENGTH: 10986
<212> TYPE: DNA
<213> ORGANISM: Homo sapiens

<400> SEQUENCE: 7
atgagccgca gagcccccggg gtctcggctg agcagcggcg gcggcggcgg cggcaccaag      60
tatccgcgga gctggaatga ctggcaaccc agaactgata gtgcatcagc cgacccagat     120
aatttaaaat attcttcatc agagataga  ggtggttctt cctcttatgg actgcaacct     180
tcaaattcag ctgtggtgtc tcggcaaagg cacgatgata ccagagtcca cgctgacata     240
cagaatgacg aaaagggtgg ctacagtgtc aatggaggat ctggggaaaa tacttatggt     300
cggaagtcgt tggggcaaga gctgagggtt aacaatgtga ccagccctga gttcaccagt     360
gttcagcatg gcagtcgtgc tttagccacc aaagacatga ggaaatcaca ggagagatcg     420
atgtcttatt ctgatgagtc tcgactgtcg aatcttcttc ggaggatcac ccgggaagac     480
gacagagacc gaagattggc tactgtaaag cagttgaaag aatttattca gcaaccagaa     540
aataagctgg tactagttaa caattggat  aatatcttgg ctgctgtaca tgacgtgctt     600
aatgaaagta gcaaattgct tcaggagttg agacaggagg gagcttgctg tcttggcctt     660
ctttgtgctt ctctgagcta tgaggctgag aagatcttca gtggattttt agcaaatttt     720
agctcatctg caaagatga  agttaaactc ctctacttat gtgccaccta caaagcacta     780
gagactgtag agaaaagaa  agccttttca tctgtaatgc agcttgtaat gaccagcctg     840
cagtctattc ttgaaaatgt ggatacacca gaattgcttt gtaaatgtgt taagtgcatt     900
cttttggtgg ctcgatgtta ccctcatatt ttcagcacta attttaggga tacagttgat     960
```

```
atattagttg gatggcatat agatcatact cagaaacctt cgctcacgca gcaggtatct    1020
gggtggttgc agagtttgga gccattttgg gtagctgatc ttgcattttc tactactctt    1080
cttggtcagt ttctggaaga catggaagca tatgctgagg acctcagcca tgtggcctct    1140
ggggaatcag tggatgaaga tgtccctcct ccatcagtgt cattaccaaa gctggctgca    1200
cttctccggg tatttagtac tgtggtgagg agcattgggg aacgcttcag cccaattcgg    1260
ggtcctccaa ttactgaggc atatgtaaca gatgttctgt acagagtaat gagatgtgtg    1320
acggctgcaa accaggtgtt tttttctgag gctgtgttga cagctgctaa tgagtgtgtt    1380
ggtgttttgc tcggcagctt ggatcctagc atgactatac attgtgacat ggtcattaca    1440
tatggattag accaactgga gaattgccag acttgtggta ccgattatat catctcagtc    1500
ttgaatttac tcacgctgat tgttgaacag ataaatacga aactgccatc atcatttgta    1560
gaaaaactgt ttataccatc atctaaacta ctattcttgc gttatcataa agaaaaagag    1620
gttgttgctg tagcccatgc tgtttatcaa gcagtgctca gcttgaagaa tattcctgtt    1680
ttggagactg cctataagtt aatattggga gaaatgactt gtgccctaaa caacctccta    1740
cacagtctac aacttcctga ggcctgttct gaaataaaac atgaggcttt taagaatcat    1800
gtgttcaatg tagacaatgc aaaatttgta gttatatttg acctcagtgc cctgactaca    1860
attggaaatg ccaaaaactc actaataggg atgtgggcgc tatctccaac tgtctttgca    1920
cttctgagta agaatctgat gattgtgcac agtgacctgg ctgttcactt ccctgccatt    1980
cagtatgctg tgctctacac attgtattct cattgtacca ggcatgatca ctttatctct    2040
agtagcctca gttcttcctc tccttctttg tttgatggag ctgtgattag cactgtaact    2100
acggctacaa agaaacattt ctcaattata ttaaatcttc tgggaatatt acttaagaaa    2160
gataacctta accaggacac gaggaaactg ttaatgactt gggctttgga agcagctgtt    2220
ttaatgaaga agtctgaaac atacgcacct ttattctctc ttccgtcttt ccataaattt    2280
tgcaaaggcc ttttagccaa cactctcgtt gaagatgtga atatctgtct gcaggcatgc    2340
agcagtctac atgctctgtc ctcttccttg ccagatgatc ttttacagag atgtgtcgat    2400
gtttgccgtg ttcaactagt gcacagtgga actcgtattc gacaagcatt tggaaaactg    2460
ttgaaatcaa ttcctttaga tgttgtccta agcaataaca atcacacaga aattcaagaa    2520
atttctttag cattaagaag tcacatgagt aaagcaccaa gtaatacatt ccaccccccaa    2580 gatttctctg atgttattag ttttattttg tatgggaact ctcatagaac agggaaggac    2640
aattggttgg aaagactgtt ctatagctgc cagagactgg ataagcgtga ccagtcaaca    2700
attccacgca atctcctgaa gacagatgct gtcctttggc agtgggccat atgggaagct    2760
gcacaattca ctgttctttc taagctgaga accccactgg gcagagctca agacaccttc    2820
cagacaattg aaggtatcat tcgaagtctc gcagctcaca cattaaaccc tgatcaggat    2880
gttagtcagt ggacaactgc agacaatgat gaaggccatg gtaacaacca acttagactt    2940
gttcttcttc tgcagtatct ggaaaatctg gagaaattaa tgtataatgc atacgaggga    3000
tgtgctaatg cattaacttc acctcccaag gtcattagaa ctttttttcta taccaatcgc    3060 caaacttgtc aggactggct aacgcggatt cgactctcca tcatgagggt aggattgttg    3120
gcaggccagc ctgcagtgac agtgagacat ggctttgact tgcttacaga gatgaaaaca    3180
accagcctat ctcaggggaa tgaattggaa gtaaccatta tgatggtggt agaagcatta    3240
tgtgaacttc attgtcctga agctatacag ggaattgctg tctggtcatc atctattgtt    3300
ggaaaaaatc ttctgtggat taactcagtg gctcaacagg ctgaagggag gtttgaaaag    3360
```

| | | | | |
|---|---|---|---|---|
| gcctctgtgg | agtaccagga | acacctgtgt | gccatgacag | gtgttgattg | ctgcatctcc | 3420 |
| agctttgaca | aatcggtgct | caccttagcc | aatgctgggc | gtaacagtgc | cagcccgaaa | 3480 |
| cattctctga | atggtgaatc | cagaaaaact | gtgctgtcca | aaccgactga | ctcttcccct | 3540 |
| gaggttataa | attatttagg | aaataaagca | tgtgagtgct | acatctcaat | tgccgattgg | 3600 |
| gctgctgtgc | aggaatggca | gaacgctatc | catgacttga | aaagagtac | cagtagcact | 3660 |
| tccctcaacc | tgaaagctga | cttcaactat | ataaaatcat | taagcagctt | tgagtctgga | 3720 |
| aaatttgttg | aatgtaccga | gcagttagaa | ttgttaccag | gagaaaatat | caatctactt | 3780 |
| gctggaggat | caaagaaaaa | aatagacatg | aaaaaactgc | ttcctaacat | gttaagtccg | 3840 |
| gatccgaggg | aacttcagaa | atccattgaa | gttcaattgt | taagaagttc | tgtttgtttg | 3900 |
| gcaactgctt | taaacccgat | agaacaagat | cagaagtggc | agtctataac | tgaaaatgtg | 3960 |
| gtaaagtact | tgaagcaaac | atcccgcatc | gctattggac | ctctgagact | ttctacttta | 4020 |
| acagtttcac | agtctttgcc | agttctaagt | accttgcagc | tgtattgctc | atctgctttg | 4080 |
| gagaacacag | tttctaacag | actttcaaca | gaggactgtc | ttattccact | cttcagtgaa | 4140 |
| gctttacgtt | catgtaaaca | gcatgacgtg | aggccatgga | tgcaggcatt | aaggtatact | 4200 |
| atgtaccaga | atcagttgtt | ggagaaaatt | aaagaacaaa | cagtcccaat | tagaagccat | 4260 |
| ctcatggaat | taggtctaac | agcagcaaaa | tttgctagaa | aacgagggaa | tgtgtccctt | 4320 |
| gcaacaagac | tgctggcaca | gtgcagtgaa | gttcagctgg | gaaagaccac | cactgcacag | 4380 |
| gatttagtcc | aacatttaa | aaaactatca | acccaaggtc | aagtggatga | aaaatggggg | 4440 |
| cccgaacttg | atattgaaaa | aaccaaattg | ctttatacag | caggccagtc | aacacatgca | 4500 |
| atggaaatgt | tgagttcttg | tgccatatct | ttctgcaagt | ctgtgaaagc | tgaatatgca | 4560 |
| gttgctaaat | caattctgac | actggctaaa | tggatccagg | cagaatggaa | agagatttca | 4620 |
| ggacagctga | aacaggttta | cagagctcag | caccaacaga | acttcacagg | tctttctact | 4680 |
| ttgtctaaaa | acatactcac | tctaatagaa | ctgccatctg | ttaatacgat | ggaagaagag | 4740 |
| tatcctcgga | tcgagagtga | atctacagtg | catattggag | ttggagaacc | tgacttcatt | 4800 |
| ttgggacagt | tgtatcacct | gtcttcagta | caggcacctg | aagtagccaa | atcttgggca | 4860 |
| gcgttggcca | gctgggctta | taggtggggc | agaaaggtgg | ttgacaatgc | cagtcaggga | 4920 |
| gaaggtgttc | gtctgctgcc | tagagaaaaa | tctgaagttc | agaatctact | tccagacact | 4980 |
| ataactgagg | aagagaaaga | gagaatatat | ggtattcttg | gacaggctgt | gtgtcggccg | 5040 |
| gcggggattc | aggatgaaga | tataacactt | cagataactg | agagtgaaga | caacgaagaa | 5100 |
| gatgacatgg | ttgatgttat | ctggcgtcag | ttgatatcaa | gctgcccatg | gctttcagaa | 5160 |
| cttgatgaaa | gtgcaactga | aggagttatt | aaagtgtgga | ggaaagttgt | agatagaata | 5220 |
| ttcagcctgt | acaaactctc | ttgcagtgca | tactttactt | tccttaaact | caacgctggt | 5280 |
| caaattcctt | tagatgagga | tgaccctagg | ctgcatttaa | gtcacagagt | ggaacagagc | 5340 |
| actgatgaca | tgattgtgat | ggccacattg | cgcctgctgc | ggttgctcgt | gaagcatgct | 5400 |
| ggtgagcttc | ggcagtatct | ggagcacggc | ttggagacaa | cacccactgc | accatggaga | 5460 |
| ggaattattc | cgcaactttt | ctcacgctta | aaccaccctg | aagtgtatgt | gcgccaaagt | 5520 |
| atttgtaacc | ttctctgccg | tgtggctcaa | gattccccac | atctcatatt | gtatcctgca | 5580 |
| atagtgggta | ccatatcgct | tagtagtgaa | tcccaggctt | caggaaataa | attttccact | 5640 |
| gcaattccaa | ctttacttgg | caatattcaa | ggagaagaat | tgctggtttc | tgaatgtgag | 5700 |

```
ggaggaagtc ctcctgcatc tcaggatagc aataaggatg aacctaaaag tggattaaat    5760
gaagaccaag ccatgatgca ggattgttac agcaaaattg tagataagct gtcctctgca    5820
aaccccacca tggtattaca ggttcagatg ctcgtggctg aactgcgcag ggtcactgtg    5880
ctctgggatg agctctggct gggagttttg ctgcaacaac acatgtatgt cctgagacga    5940
attcagcagc ttgaagatga ggtgaagaga gtccagaaca caacacctt acgcaaagaa     6000 gagaaaattg caatcatgag ggagaagcac acagctttga tgaagcccat cgtatttgct    6060
ttggagcatg tgaggagtat cacagcggct cctgcagaaa cacctcatga aaaatggttt    6120
caggataact atggtgatgc cattgaaaat gccctagaaa actgaagac tccattgaac      6180 cctgcaaagc ctgggagcag ctggattcca tttaaagaga taatgctaag tttgcaacag    6240
agagcacaga aacgtgcaag ttacatcttg cgtcttgaag aaatcagtcc atggttggct    6300
gccatgacta acactgaaat tgctcttcct ggggaagtct cagccagaga cactgtcaca    6360
atccatagtg tgggcggaac catcacaatc ttaccgacta aaaccaagcc aaagaaactt    6420 ctcttttcttg gatcagatgg gaagagctat ccttatcttt tcaaaggact ggaggattta    6480
catctggatg agagaataat gcagttccta tctattgtga ataccatgtt tgctacaatt    6540
aatcgccaag aaacaccccg gttccatgct cgacactatt ctgtaacacc actaggaaca    6600
agatcaggac taatccagtg ggtagatgga gccacaccct tatttggtct ttacaaacga    6660
tggcaacaac gggaagctgc cttacaagca caaaaggccc aagattccta ccaaactcct    6720
cagaatcctg gaattgtacc ccgtcctagt gaactttatt acagtaaaat tggccctgct    6780
ttgaaaacag ttgggcttag cctggatgtg tcccgtcggg attggcctct tcatgtaatg    6840
aaggcagtat tggaagagtt aatggaggcc acaccccccga atctccttgc caaagagctc    6900
tggtcatctt gcacaacacc tgatgaatgg tggagagtta cgcagtctta tgcaagatct    6960
actgcagtca tgtctatggt tggatacata attggccttg gagacagaca tctggataat    7020
gttcttatag atatgacgac tggagaagtt gttcacatag attacaatgt ttgctttgaa    7080
aaaggtaaaa gccttagagt tcctgagaaa gtacctttc gaatgacaca aaacattgaa     7140
acagcactgg gtgtaactgg agtagaaggt gtatttaggc tttcatgtga gcaggtttta    7200
cacattatgc ggcgtggcag agagaccctg ctgacgctgc tggaggcctt tgtgtacgac    7260
cctctggtgg actggacagc aggaggcgag gctgggtttg ctggtgctgt ctatggtgga    7320
ggtggccagc aggccgagag caagcagagc aagagagaga tggagcgaga gatcacccgc    7380
agcctgtttt cttctagagt agctgagatt aaggtgaact ggtttaagaa tagagatgag    7440
atgctggttg tgcttcccaa gttggacggt agcttagatg aatacctaag cttgcaagag    7500
caactgacag atgtggaaaa actgcagggc aaactactgg aggaaataga gtttctagaa    7560
ggagctgaag gggtggatca tccttctcat actctgcaac acaggtattc tgagcacacc    7620
caactacaga ctcagcaaag agctgttcag gaagcaatcc aggtgaagct gaatgaattt    7680
gaacaatgga taacacatta tcaggctgca ttcaataatt tagaagcaac acagcttgca    7740
agcttgcttc aagagataag cacacaaatg gaccttggtc ctccaagtta cgtgccagca    7800
acagcctttc tgcagaatgc tggtcaggcc cacttgatta gccagtgcga gcagctggag    7860
ggggaggttg gtgctctcct gcagcagagg cgctccgtgc tccgtggctg tctggagcaa    7920
ctgcatcact atgcaaccgt ggccctgcag tatccgaagg ccatatttca gaaacatcga    7980
attgaacagt ggaagacctg gatggaagag ctcatctgta acaccacagt agagcgttgt    8040
caagagctct ataggaaata tgaaatgcaa tatgctcccc agccacccccc aacagtgtgt    8100
```

```
cagttcatca ctgccactga aatgaccctg cagcgatacg cagcagacat caacagcaga    8160
cttattagac aagtggaacg cttgaaacag gaagctgtca ctgtgccagt ttgtgaagat    8220
cagttgaaag aaaattgaacg ttgcattaaa gttttccttc atgagaatgg agaagaagga    8280
tctttgagtc tagcaagtgt tattatttct gcccttttgta cccttacaag gcgtaacctg    8340
atgatggaag gtgcagcgtc aagtgctgga gaacagctgg ttgatctgac ttctcgggat    8400
ggagcctggt tcttggagga actctgcagt atgagcggaa acgtcacctg cttggttcag    8460
ttactgaagc agtgccacct ggtgccacag gacttagata tcccgaaccc catggaagcg    8520
tctgagacag ttcacttagc caatggagtg tatacctcac ttcaggaatt gaattcgaat    8580
ttccggcaaa tcatatttcc agaagcactt cgatgtttaa tgaaggggga atacacgtta    8640
gaaagtatgc tgcatgaact ggacggtctt attgagcaga ccaccgatgg cgttcccctg    8700
cagactctag tggaatctct tcaggcctac ttaagaaacg cagctatggg actggaagaa    8760
gaaacacatg ctcattacat cgatgttgcc agactactac atgctcagta cggtgaatta    8820
atccaaccga gaaatggttc agttgatgaa acacccaaaa tgtcagctgg ccagatgctt    8880
ttggtagcat tcgatggcat gttttgctcaa gttgaaactg ctttcagctt attagttgaa    8940
aagttgaaca agatggaaat tcccatagct tggcgaaaga ttgacatcat aagggaagcc    9000
aggagtactc aagttaattt ttttgatgat gataatcacc ggcaggtgct agaagagatt    9060
ttctttctaa aaagactaca gactattaag gagttcttca ggctctgtgg tacctttttct    9120 aaaacattgt caggatcaag ttcacttgaa gatcagaata ctgtgaatgg gcctgtacag    9180
attgtcaatg tgaaaaccct ttttagaaac tcttgtttca gtgaagacca aatggccaaa    9240
cctatcaagg cattcacagc tgactttgtg aggcagctct tgatagggct acccaaccaa    9300
gccctcggac tcacactgtg cagttttatc agtgctctgg gtgtagacat cattgctcaa    9360
gtagaggcaa aggactttgg tgccgaaagc aaagtttctg ttgatgatct ctgtaagaaa    9420
gcggtggaac ataacatcca gatagggaag ttctctcagc tggttatgaa cagggcaact    9480
gtgttagcaa gttcttacga cactgcctgg aagaagcatg acttggtgcg aaggctagaa    9540
accagtattt cttcttgtaa gacaagcctg cagcgggttc agctgcatat tgccatgttt    9600
cagtggcaac atgaagatct acttatcaat agaccacaag ccatgtcagt cacacctccc    9660
ccacggtctg ctatcctaac cagcatgaaa agaagctgc atacccctgag ccagattgaa    9720 acttctattg caacagttca ggagaagcta gctgcacttg aatcaagtat tgaacagcga    9780
ctcaagtggg caggtggtgc caaccctgca ttggcccctg tactacaaga ttttgaagca    9840
acgatagctg aaagaagaaa tcttgtcctt aaagagagcc aaagagcaag tcaggtcaca    9900
tttctctgca gcaatatcat tcatttgaaa agtttacgaa caagaactgc agaagcctta    9960
aacctggatg cggcgttatt tgaactaatc aagcgatgtc agcagatgtg ttcgtttgca   10020
tcacagttta acgttcagt gtctgagtta gagcttcgtt tattacagag agtggacact   10080
ggtcttgaac atcctattgg cagctctgaa tggcttttgt cagcacacaa acagttgacc   10140
caggatatgt ctactcagag ggcaattcag acagagaaag agcagcagat agaaacggtc   10200
tgtgaaacaa ttcagaatct ggttgataat ataaagactg tgctcactgg tcataaccga   10260
cagcttggag atgtcaaaca tctcttgaaa gctatggcta aggatgaaga agctgctctg   10320
gcagatggtg aagatgttcc ctatgagaac agtgttaggc agttttttggg tgaatataaa   10380 tcatggcaag acaacattca aacagttcta tttacattag tccaggctat gggtcaggtt   10440
```

-continued

```
cgaagtcaag aacacgttga atgctccag gaaatcactc ccaccttgaa agaactgaaa    10500
acacaaagtc agagtatcta taataattta gtgagttttg catcacccct agtcaccgat    10560
gcaacaaatg aatgttcgag tccaacgtca tctgctactt atcagccatc cttcgctgca    10620
gcagtccgga gtaacactgg ccagaagact cagcctgatg tcatgtcaca gaatgctaga    10680
aagctgatcc agaaaaatct tgctacatca gctgatactc caccaagcac cgttccagga    10740
actggcaaga gtgttgcttg tagtcctaaa aaggcagtca gagaccctaa aactgggaaa    10800
gcggtgcaag agagaaactc ctatgcagtg agtgtgtgga agagagtgaa agccaagtta    10860
gagggccgag atgttgatcc gaataggagg atgtcagttg ctgaacaggt tgactatgtc    10920
attaaggaag caactaatct agataacttg gctcagctgt atgaaggttg gacagcctgg    10980
gtgtga                                                              10986
```

<210> SEQ ID NO 8
<211> LENGTH: 3661
<212> TYPE: PRT
<213> ORGANISM: Homo sapiens
<400> SEQUENCE: 8

```
Met Ser Arg Arg Ala Pro Gly Ser Arg Leu Ser Gly Gly Gly Gly
1               5                   10                  15

Gly Gly Thr Lys Tyr Pro Arg Ser Trp Asn Asp Trp Gln Pro Arg Thr
            20                  25                  30

Asp Ser Ala Ser Ala Asp Pro Asp Asn Leu Lys Tyr Ser Ser Arg
        35                  40                  45

Asp Arg Gly Gly Ser Ser Tyr Gly Leu Gln Pro Ser Asn Ser Ala
    50                  55                  60

Val Val Ser Arg Gln Arg His Asp Asp Thr Arg Val His Ala Asp Ile
65                  70                  75                  80

Gln Asn Asp Glu Lys Gly Gly Tyr Ser Val Asn Gly Ser Gly Glu
                85                  90                  95

Asn Thr Tyr Gly Arg Lys Ser Leu Gly Gln Glu Leu Arg Val Asn Asn
            100                 105                 110

Val Thr Ser Pro Glu Phe Thr Val Gln His Gly Ser Arg Ala Leu
        115                 120                 125

Ala Thr Lys Asp Met Arg Lys Ser Gln Glu Arg Ser Met Ser Tyr Ser
    130                 135                 140

Asp Glu Ser Arg Leu Ser Asn Leu Leu Arg Arg Ile Thr Arg Glu Asp
145                 150                 155                 160

Asp Arg Asp Arg Arg Leu Ala Thr Val Lys Gln Leu Lys Glu Phe Ile
                165                 170                 175

Gln Gln Pro Glu Asn Lys Leu Val Leu Val Lys Gln Leu Asp Asn Ile
            180                 185                 190

Leu Ala Ala Val His Asp Val Leu Asn Glu Ser Ser Lys Leu Leu Gln
        195                 200                 205

Glu Leu Arg Gln Glu Gly Ala Cys Cys Leu Gly Leu Leu Cys Ala Ser
    210                 215                 220

Leu Ser Tyr Glu Ala Glu Lys Ile Phe Lys Trp Ile Phe Ser Lys Phe
225                 230                 235                 240

Ser Ser Ser Ala Lys Asp Glu Val Lys Leu Leu Tyr Leu Cys Ala Thr
                245                 250                 255

Tyr Lys Ala Leu Glu Thr Val Gly Glu Lys Lys Ala Phe Ser Ser Val
            260                 265                 270
```

```
Met Gln Leu Val Met Thr Ser Leu Gln Ser Ile Leu Glu Asn Val Asp
            275                 280                 285

Thr Pro Glu Leu Leu Cys Lys Cys Val Lys Cys Ile Leu Leu Val Ala
290                 295                 300

Arg Cys Tyr Pro His Ile Phe Ser Thr Asn Phe Arg Asp Thr Val Asp
305                 310                 315                 320

Ile Leu Val Gly Trp His Ile Asp His Thr Gln Lys Pro Ser Leu Thr
                325                 330                 335

Gln Gln Val Ser Gly Trp Leu Gln Leu Glu Pro Phe Trp Val Ala
                340                 345                 350

Asp Leu Ala Phe Ser Thr Thr Leu Leu Gly Gln Phe Leu Glu Asp Met
            355                 360                 365

Glu Ala Tyr Ala Glu Asp Leu Ser His Val Ala Ser Gly Glu Ser Val
    370                 375                 380

Asp Glu Asp Val Pro Pro Ser Val Ser Leu Pro Lys Leu Ala Ala
385                 390                 395                 400

Leu Leu Arg Val Phe Ser Thr Val Val Arg Ser Ile Gly Glu Arg Phe
                405                 410                 415

Ser Pro Ile Arg Gly Pro Pro Ile Thr Glu Ala Tyr Val Thr Asp Val
                420                 425                 430

Leu Tyr Arg Val Met Arg Cys Val Thr Ala Ala Asn Gln Val Phe Phe
        435                 440                 445

Ser Glu Ala Val Leu Thr Ala Ala Asn Glu Cys Val Gly Val Leu Leu
    450                 455                 460

Gly Ser Leu Asp Pro Ser Met Thr Ile His Cys Asp Met Val Ile Thr
465                 470                 475                 480

Tyr Gly Leu Asp Gln Leu Glu Asn Cys Gln Thr Cys Gly Thr Asp Tyr
                485                 490                 495

Ile Ile Ser Val Leu Asn Leu Thr Leu Ile Val Glu Gln Ile Asn
                500                 505                 510

Thr Lys Leu Pro Ser Ser Phe Val Glu Lys Leu Phe Ile Pro Ser Ser
        515                 520                 525

Lys Leu Leu Phe Leu Arg Tyr His Lys Glu Lys Glu Val Val Ala Val
    530                 535                 540

Ala His Ala Val Tyr Gln Ala Val Leu Ser Leu Lys Asn Ile Pro Val
545                 550                 555                 560

Leu Glu Thr Ala Tyr Lys Leu Ile Leu Gly Glu Met Thr Cys Ala Leu
                565                 570                 575

Asn Asn Leu Leu His Ser Leu Gln Leu Pro Glu Ala Cys Ser Glu Ile
            580                 585                 590

Lys His Glu Ala Phe Lys Asn His Val Phe Asn Val Asp Asn Ala Lys
        595                 600                 605

Phe Val Val Ile Phe Asp Leu Ser Ala Leu Thr Thr Ile Gly Asn Ala
610                 615                 620

Lys Asn Ser Leu Ile Gly Met Trp Ala Leu Ser Pro Thr Val Phe Ala
625                 630                 635                 640

Leu Leu Ser Lys Asn Leu Met Ile Val His Ser Asp Leu Ala Val His
                645                 650                 655

Phe Pro Ala Ile Gln Tyr Ala Val Leu Tyr Thr Leu Tyr Ser His Cys
                660                 665                 670

Thr Arg His Asp His Phe Ile Ser Ser Ser Leu Ser Ser Ser Ser Pro
            675                 680                 685

Ser Leu Phe Asp Gly Ala Val Ile Ser Thr Val Thr Thr Ala Thr Lys
```

```
              690             695             700
Lys His Phe Ser Ile Ile Leu Asn Leu Leu Gly Ile Leu Leu Lys Lys
705             710             715             720

Asp Asn Leu Asn Gln Asp Thr Arg Lys Leu Leu Met Thr Trp Ala Leu
            725             730             735

Glu Ala Ala Val Leu Met Lys Lys Ser Glu Thr Tyr Ala Pro Leu Phe
            740             745             750

Ser Leu Pro Ser Phe His Lys Phe Cys Lys Gly Leu Leu Ala Asn Thr
            755             760             765

Leu Val Glu Asp Val Asn Ile Cys Leu Gln Ala Cys Ser Ser Leu His
            770             775             780

Ala Leu Ser Ser Ser Leu Pro Asp Asp Leu Leu Gln Arg Cys Val Asp
785             790             795             800

Val Cys Arg Val Gln Leu Val His Ser Gly Thr Arg Ile Arg Gln Ala
            805             810             815

Phe Gly Lys Leu Leu Lys Ser Ile Pro Leu Asp Val Val Leu Ser Asn
            820             825             830

Asn Asn His Thr Glu Ile Gln Glu Ile Ser Leu Ala Leu Arg Ser His
            835             840             845

Met Ser Lys Ala Pro Ser Asn Thr Phe His Pro Gln Asp Phe Ser Asp
850             855             860

Val Ile Ser Phe Ile Leu Tyr Gly Asn Ser His Arg Thr Gly Lys Asp
865             870             875             880

Asn Trp Leu Glu Arg Leu Phe Tyr Ser Cys Gln Arg Leu Asp Lys Arg
            885             890             895

Asp Gln Ser Thr Ile Pro Arg Asn Leu Leu Lys Thr Asp Ala Val Leu
            900             905             910

Trp Gln Trp Ala Ile Trp Glu Ala Ala Gln Phe Thr Val Leu Ser Lys
            915             920             925

Leu Arg Thr Pro Leu Gly Arg Ala Gln Asp Thr Phe Gln Thr Ile Glu
            930             935             940

Gly Ile Ile Arg Ser Leu Ala Ala His Thr Leu Asn Pro Asp Gln Asp
945             950             955             960

Val Ser Gln Trp Thr Thr Ala Asp Asn Asp Glu Gly His Gly Asn Asn
            965             970             975

Gln Leu Arg Leu Val Leu Leu Gln Tyr Leu Glu Asn Leu Glu Lys
            980             985             990

Leu Met Tyr Asn Ala Tyr Glu Gly Cys Ala Asn Ala Leu Thr Ser Pro
            995             1000            1005

Pro Lys Val Ile Arg Thr Phe Phe Tyr Thr Asn Arg Gln Thr Cys
    1010            1015            1020

Gln Asp Trp Leu Thr Arg Ile Arg Leu Ser Ile Met Arg Val Gly
    1025            1030            1035

Leu Leu Ala Gly Gln Pro Ala Val Thr Val Arg His Gly Phe Asp
    1040            1045            1050

Leu Leu Thr Glu Met Lys Thr Thr Ser Leu Ser Gln Gly Asn Glu
    1055            1060            1065

Leu Glu Val Thr Ile Met Met Val Val Glu Ala Leu Cys Glu Leu
    1070            1075            1080

His Cys Pro Glu Ala Ile Gln Gly Ile Ala Val Trp Ser Ser Ser
    1085            1090            1095

Ile Val Gly Lys Asn Leu Leu Trp Ile Asn Ser Val Ala Gln Gln
    1100            1105            1110
```

```
Ala Glu Gly Arg Phe Glu Lys Ala Ser Val Glu Tyr Gln Glu His
1115                1120                1125

Leu Cys Ala Met Thr Gly Val Asp Cys Cys Ile Ser Ser Phe Asp
1130                1135                1140

Lys Ser Val Leu Thr Leu Ala Asn Ala Gly Arg Asn Ser Ala Ser
1145                1150                1155

Pro Lys His Ser Leu Asn Gly Glu Ser Arg Lys Thr Val Leu Ser
1160                1165                1170

Lys Pro Thr Asp Ser Ser Pro Glu Val Ile Asn Tyr Leu Gly Asn
1175                1180                1185

Lys Ala Cys Glu Cys Tyr Ile Ser Ile Ala Asp Trp Ala Ala Val
1190                1195                1200

Gln Glu Trp Gln Asn Ala Ile His Asp Leu Lys Lys Ser Thr Ser
1205                1210                1215

Ser Thr Ser Leu Asn Leu Lys Ala Asp Phe Asn Tyr Ile Lys Ser
1220                1225                1230

Leu Ser Ser Phe Glu Ser Gly Lys Phe Val Glu Cys Thr Glu Gln
1235                1240                1245

Leu Glu Leu Leu Pro Gly Glu Asn Ile Asn Leu Leu Ala Gly Gly
1250                1255                1260

Ser Lys Glu Lys Ile Asp Met Lys Lys Leu Leu Pro Asn Met Leu
1265                1270                1275

Ser Pro Asp Pro Arg Glu Leu Gln Lys Ser Ile Glu Val Gln Leu
1280                1285                1290

Leu Arg Ser Ser Val Cys Leu Ala Thr Ala Leu Asn Pro Ile Glu
1295                1300                1305

Gln Asp Gln Lys Trp Gln Ser Ile Thr Glu Asn Val Val Lys Tyr
1310                1315                1320

Leu Lys Gln Thr Ser Arg Ile Ala Ile Gly Pro Leu Arg Leu Ser
1325                1330                1335

Thr Leu Thr Val Ser Gln Ser Leu Pro Val Leu Ser Thr Leu Gln
1340                1345                1350

Leu Tyr Cys Ser Ser Ala Leu Glu Asn Thr Val Ser Asn Arg Leu
1355                1360                1365

Ser Thr Glu Asp Cys Leu Ile Pro Leu Phe Ser Glu Ala Leu Arg
1370                1375                1380

Ser Cys Lys Gln His Asp Val Arg Pro Trp Met Gln Ala Leu Arg
1385                1390                1395

Tyr Thr Met Tyr Gln Asn Gln Leu Leu Glu Lys Ile Lys Glu Gln
1400                1405                1410

Thr Val Pro Ile Arg Ser His Leu Met Glu Leu Gly Leu Thr Ala
1415                1420                1425

Ala Lys Phe Ala Arg Lys Arg Gly Asn Val Ser Leu Ala Thr Arg
1430                1435                1440

Leu Leu Ala Gln Cys Ser Glu Val Gln Leu Gly Lys Thr Thr Thr
1445                1450                1455

Ala Gln Asp Leu Val Gln His Phe Lys Lys Leu Ser Thr Gln Gly
1460                1465                1470

Gln Val Asp Glu Lys Trp Gly Pro Glu Leu Asp Ile Glu Lys Thr
1475                1480                1485

Lys Leu Leu Tyr Thr Ala Gly Gln Ser Thr His Ala Met Glu Met
1490                1495                1500
```

```
Leu Ser Ser Cys Ala Ile Ser Phe Cys Lys Ser Val Lys Ala Glu
1505                1510                1515

Tyr Ala Val Ala Lys Ser Ile Leu Thr Leu Ala Lys Trp Ile Gln
1520                1525                1530

Ala Glu Trp Lys Glu Ile Ser Gly Gln Leu Lys Gln Val Tyr Arg
1535                1540                1545

Ala Gln His Gln Gln Asn Phe Thr Gly Leu Ser Thr Leu Ser Lys
1550                1555                1560

Asn Ile Leu Thr Leu Ile Glu Leu Pro Ser Val Asn Thr Met Glu
1565                1570                1575

Glu Glu Tyr Pro Arg Ile Glu Ser Glu Ser Thr Val His Ile Gly
1580                1585                1590

Val Gly Glu Pro Asp Phe Ile Leu Gly Gln Leu Tyr His Leu Ser
1595                1600                1605

Ser Val Gln Ala Pro Glu Val Ala Lys Ser Trp Ala Ala Leu Ala
1610                1615                1620

Ser Trp Ala Tyr Arg Trp Gly Arg Lys Val Val Asp Asn Ala Ser
1625                1630                1635

Gln Gly Glu Gly Val Arg Leu Leu Pro Arg Glu Lys Ser Glu Val
1640                1645                1650

Gln Asn Leu Leu Pro Asp Thr Ile Thr Glu Glu Glu Lys Glu Arg
1655                1660                1665

Ile Tyr Gly Ile Leu Gly Gln Ala Val Cys Arg Pro Ala Gly Ile
1670                1675                1680

Gln Asp Glu Asp Ile Thr Leu Gln Ile Thr Glu Ser Glu Asp Asn
1685                1690                1695

Glu Glu Asp Asp Met Val Asp Val Ile Trp Arg Gln Leu Ile Ser
1700                1705                1710

Ser Cys Pro Trp Leu Ser Glu Leu Asp Glu Ser Ala Thr Glu Gly
1715                1720                1725

Val Ile Lys Val Trp Arg Lys Val Val Asp Arg Ile Phe Ser Leu
1730                1735                1740

Tyr Lys Leu Ser Cys Ser Ala Tyr Phe Thr Phe Leu Lys Leu Asn
1745                1750                1755

Ala Gly Gln Ile Pro Leu Asp Glu Asp Pro Arg Leu His Leu
1760                1765                1770

Ser His Arg Val Glu Gln Ser Thr Asp Asp Met Ile Val Met Ala
1775                1780                1785

Thr Leu Arg Leu Leu Arg Leu Leu Val Lys His Ala Gly Glu Leu
1790                1795                1800

Arg Gln Tyr Leu Glu His Gly Leu Glu Thr Thr Pro Thr Ala Pro
1805                1810                1815

Trp Arg Gly Ile Ile Pro Gln Leu Phe Ser Arg Leu Asn His Pro
1820                1825                1830

Glu Val Tyr Val Arg Gln Ser Ile Cys Asn Leu Leu Cys Arg Val
1835                1840                1845

Ala Gln Asp Ser Pro His Leu Ile Leu Tyr Pro Ala Ile Val Gly
1850                1855                1860

Thr Ile Ser Leu Ser Ser Glu Ser Gln Ala Ser Gly Asn Lys Phe
1865                1870                1875

Ser Thr Ala Ile Pro Thr Leu Leu Gly Asn Ile Gln Gly Glu Glu
1880                1885                1890

Leu Leu Val Ser Glu Cys Glu Gly Gly Ser Pro Pro Ala Ser Gln
```

-continued

```
              1895                1900                1905
Asp Ser Asn Lys Asp Glu Pro Lys Ser Gly Leu Asn Glu Asp Gln
        1910                1915                1920
Ala Met Met Gln Asp Cys Tyr Ser Lys Ile Val Asp Lys Leu Ser
        1925                1930                1935
Ser Ala Asn Pro Thr Met Val Leu Gln Val Gln Met Leu Val Ala
        1940                1945                1950
Glu Leu Arg Arg Val Thr Val Leu Trp Asp Glu Leu Trp Leu Gly
        1955                1960                1965
Val Leu Leu Gln Gln His Met Tyr Val Leu Arg Arg Ile Gln Gln
        1970                1975                1980
Leu Glu Asp Glu Val Lys Arg Val Gln Asn Asn Asn Thr Leu Arg
        1985                1990                1995
Lys Glu Glu Lys Ile Ala Ile Met Arg Glu Lys His Thr Ala Leu
        2000                2005                2010
Met Lys Pro Ile Val Phe Ala Leu Glu His Val Arg Ser Ile Thr
        2015                2020                2025
Ala Ala Pro Ala Glu Thr Pro His Glu Lys Trp Phe Gln Asp Asn
        2030                2035                2040
Tyr Gly Asp Ala Ile Glu Asn Ala Leu Glu Lys Leu Lys Thr Pro
        2045                2050                2055
Leu Asn Pro Ala Lys Pro Gly Ser Ser Trp Ile Pro Phe Lys Glu
        2060                2065                2070
Ile Met Leu Ser Leu Gln Gln Arg Ala Gln Lys Arg Ala Ser Tyr
        2075                2080                2085
Ile Leu Arg Leu Glu Glu Ile Ser Pro Trp Leu Ala Ala Met Thr
        2090                2095                2100
Asn Thr Glu Ile Ala Leu Pro Gly Glu Val Ser Ala Arg Asp Thr
        2105                2110                2115
Val Thr Ile His Ser Val Gly Gly Thr Ile Thr Ile Leu Pro Thr
        2120                2125                2130
Lys Thr Lys Pro Lys Lys Leu Leu Phe Leu Gly Ser Asp Gly Lys
        2135                2140                2145
Ser Tyr Pro Tyr Leu Phe Lys Gly Leu Glu Asp Leu His Leu Asp
        2150                2155                2160
Glu Arg Ile Met Gln Phe Leu Ser Ile Val Asn Thr Met Phe Ala
        2165                2170                2175
Thr Ile Asn Arg Gln Glu Thr Pro Arg Phe His Ala Arg His Tyr
        2180                2185                2190
Ser Val Thr Pro Leu Gly Thr Arg Ser Gly Leu Ile Gln Trp Val
        2195                2200                2205
Asp Gly Ala Thr Pro Leu Phe Gly Leu Tyr Lys Arg Trp Gln Gln
        2210                2215                2220
Arg Glu Ala Ala Leu Gln Ala Gln Lys Ala Gln Asp Ser Tyr Gln
        2225                2230                2235
Thr Pro Gln Asn Pro Gly Ile Val Pro Arg Pro Ser Glu Leu Tyr
        2240                2245                2250
Tyr Ser Lys Ile Gly Pro Ala Leu Lys Thr Val Gly Leu Ser Leu
        2255                2260                2265
Asp Val Ser Arg Arg Asp Trp Pro Leu His Val Met Lys Ala Val
        2270                2275                2280
Leu Glu Glu Leu Met Glu Ala Thr Pro Pro Asn Leu Leu Ala Lys
        2285                2290                2295
```

```
Glu Leu Trp Ser Ser Cys Thr Thr Pro Asp Glu Trp Trp Arg Val
    2300                2305                2310

Thr Gln Ser Tyr Ala Arg Ser Thr Ala Val Met Ser Met Val Gly
    2315                2320                2325

Tyr Ile Ile Gly Leu Gly Asp Arg His Leu Asp Asn Val Leu Ile
    2330                2335                2340

Asp Met Thr Thr Gly Glu Val Val His Ile Asp Tyr Asn Val Cys
    2345                2350                2355

Phe Glu Lys Gly Lys Ser Leu Arg Val Pro Glu Lys Val Pro Phe
    2360                2365                2370

Arg Met Thr Gln Asn Ile Glu Thr Ala Leu Gly Val Thr Gly Val
    2375                2380                2385

Glu Gly Val Phe Arg Leu Ser Cys Glu Gln Val Leu His Ile Met
    2390                2395                2400

Arg Arg Gly Arg Glu Thr Leu Leu Thr Leu Leu Glu Ala Phe Val
    2405                2410                2415

Tyr Asp Pro Leu Val Asp Trp Thr Ala Gly Gly Glu Ala Gly Phe
    2420                2425                2430

Ala Gly Ala Val Tyr Gly Gly Gly Gln Gln Ala Glu Ser Lys
    2435                2440                2445

Gln Ser Lys Arg Glu Met Glu Arg Glu Ile Thr Arg Ser Leu Phe
    2450                2455                2460

Ser Ser Arg Val Ala Glu Ile Lys Val Asn Trp Phe Lys Asn Arg
    2465                2470                2475

Asp Glu Met Leu Val Val Leu Pro Lys Leu Asp Gly Ser Leu Asp
    2480                2485                2490

Glu Tyr Leu Ser Leu Gln Glu Gln Leu Thr Asp Val Glu Lys Leu
    2495                2500                2505

Gln Gly Lys Leu Leu Glu Glu Ile Glu Phe Leu Glu Gly Ala Glu
    2510                2515                2520

Gly Val Asp His Pro Ser His Thr Leu Gln His Arg Tyr Ser Glu
    2525                2530                2535

His Thr Gln Leu Gln Thr Gln Gln Arg Ala Val Gln Glu Ala Ile
    2540                2545                2550

Gln Val Lys Leu Asn Glu Phe Glu Gln Trp Ile Thr His Tyr Gln
    2555                2560                2565

Ala Ala Phe Asn Asn Leu Glu Ala Thr Gln Leu Ala Ser Leu Leu
    2570                2575                2580

Gln Glu Ile Ser Thr Gln Met Asp Leu Gly Pro Pro Ser Tyr Val
    2585                2590                2595

Pro Ala Thr Ala Phe Leu Gln Asn Ala Gly Gln Ala His Leu Ile
    2600                2605                2610

Ser Gln Cys Glu Gln Leu Glu Gly Glu Val Gly Ala Leu Leu Gln
    2615                2620                2625

Gln Arg Arg Ser Val Leu Arg Gly Cys Leu Glu Gln Leu His His
    2630                2635                2640

Tyr Ala Thr Val Ala Leu Gln Tyr Pro Lys Ala Ile Phe Gln Lys
    2645                2650                2655

His Arg Ile Glu Gln Trp Lys Thr Trp Met Glu Glu Leu Ile Cys
    2660                2665                2670

Asn Thr Thr Val Glu Arg Cys Gln Glu Leu Tyr Arg Lys Tyr Glu
    2675                2680                2685
```

```
Met Gln Tyr Ala Pro Gln Pro Pro Thr Val Cys Gln Phe Ile
2690             2695            2700

Thr Ala Thr Glu Met Thr Leu Gln Arg Tyr Ala Ala Asp Ile Asn
2705             2710            2715

Ser Arg Leu Ile Arg Gln Val Glu Arg Leu Lys Gln Glu Ala Val
2720             2725            2730

Thr Val Pro Val Cys Glu Asp Gln Leu Lys Glu Ile Glu Arg Cys
2735             2740            2745

Ile Lys Val Phe Leu His Glu Asn Gly Glu Gly Ser Leu Ser
2750             2755            2760

Leu Ala Ser Val Ile Ile Ser Ala Leu Cys Thr Leu Thr Arg Arg
2765             2770            2775

Asn Leu Met Met Glu Gly Ala Ala Ser Ser Ala Gly Glu Gln Leu
2780             2785            2790

Val Asp Leu Thr Ser Arg Asp Gly Ala Trp Phe Leu Glu Glu Leu
2795             2800            2805

Cys Ser Met Ser Gly Asn Val Thr Cys Leu Val Gln Leu Leu Lys
2810             2815            2820

Gln Cys His Leu Val Pro Gln Asp Leu Asp Ile Pro Asn Pro Met
2825             2830            2835

Glu Ala Ser Glu Thr Val His Leu Ala Asn Gly Val Tyr Thr Ser
2840             2845            2850

Leu Gln Glu Leu Asn Ser Asn Phe Arg Gln Ile Ile Phe Pro Glu
2855             2860            2865

Ala Leu Arg Cys Leu Met Lys Gly Glu Tyr Thr Leu Glu Ser Met
2870             2875            2880

Leu His Glu Leu Asp Gly Leu Ile Glu Gln Thr Thr Asp Gly Val
2885             2890            2895

Pro Leu Gln Thr Leu Val Glu Ser Leu Gln Ala Tyr Leu Arg Asn
2900             2905            2910

Ala Ala Met Gly Leu Glu Glu Glu Thr His Ala His Tyr Ile Asp
2915             2920            2925

Val Ala Arg Leu Leu His Ala Gln Tyr Gly Glu Leu Ile Gln Pro
2930             2935            2940

Arg Asn Gly Ser Val Asp Glu Thr Pro Lys Met Ser Ala Gly Gln
2945             2950            2955

Met Leu Leu Val Ala Phe Asp Gly Met Phe Ala Gln Val Glu Thr
2960             2965            2970

Ala Phe Ser Leu Leu Val Glu Lys Leu Asn Lys Met Glu Ile Pro
2975             2980            2985

Ile Ala Trp Arg Lys Ile Asp Ile Ile Arg Glu Ala Arg Ser Thr
2990             2995            3000

Gln Val Asn Phe Phe Asp Asp Asn His Arg Gln Val Leu Glu
3005             3010            3015

Glu Ile Phe Phe Leu Lys Arg Leu Gln Thr Ile Lys Glu Phe Phe
3020             3025            3030

Arg Leu Cys Gly Thr Phe Ser Lys Thr Leu Ser Gly Ser Ser Ser
3035             3040            3045

Leu Glu Asp Gln Asn Thr Val Asn Gly Pro Val Gln Ile Val Asn
3050             3055            3060

Val Lys Thr Leu Phe Arg Asn Ser Cys Phe Ser Glu Asp Gln Met
3065             3070            3075

Ala Lys Pro Ile Lys Ala Phe Thr Ala Asp Phe Val Arg Gln Leu
```

-continued

```
                    3080                3085                3090
Leu Ile Gly Leu Pro Asn Gln Ala Leu Gly Leu Thr Leu Cys Ser
        3095                3100                3105

Phe Ile Ser Ala Leu Gly Val Asp Ile Ile Ala Gln Val Glu Ala
        3110                3115                3120

Lys Asp Phe Gly Ala Glu Ser Lys Val Ser Val Asp Asp Leu Cys
        3125                3130                3135

Lys Lys Ala Val Glu His Asn Ile Gln Ile Gly Lys Phe Ser Gln
        3140                3145                3150

Leu Val Met Asn Arg Ala Thr Val Leu Ala Ser Ser Tyr Asp Thr
        3155                3160                3165

Ala Trp Lys Lys His Asp Leu Val Arg Arg Leu Glu Thr Ser Ile
        3170                3175                3180

Ser Ser Cys Lys Thr Ser Leu Gln Arg Val Gln Leu His Ile Ala
        3185                3190                3195

Met Phe Gln Trp Gln His Glu Asp Leu Leu Ile Asn Arg Pro Gln
        3200                3205                3210

Ala Met Ser Val Thr Pro Pro Arg Ser Ala Ile Leu Thr Ser
        3215                3220                3225

Met Lys Lys Leu His Thr Leu Ser Gln Ile Glu Thr Ser Ile
        3230                3235                3240

Ala Thr Val Gln Glu Lys Leu Ala Ala Leu Glu Ser Ser Ile Glu
        3245                3250                3255

Gln Arg Leu Lys Trp Ala Gly Gly Ala Asn Pro Ala Leu Ala Pro
        3260                3265                3270

Val Leu Gln Asp Phe Glu Ala Thr Ile Ala Glu Arg Arg Asn Leu
        3275                3280                3285

Val Leu Lys Glu Ser Gln Arg Ala Ser Gln Val Thr Phe Leu Cys
        3290                3295                3300

Ser Asn Ile Ile His Phe Glu Ser Leu Arg Thr Arg Thr Ala Glu
        3305                3310                3315

Ala Leu Asn Leu Asp Ala Ala Leu Phe Glu Leu Ile Lys Arg Cys
        3320                3325                3330

Gln Gln Met Cys Ser Phe Ala Ser Gln Phe Asn Ser Ser Val Ser
        3335                3340                3345

Glu Leu Glu Leu Arg Leu Leu Gln Arg Val Asp Thr Gly Leu Glu
        3350                3355                3360

His Pro Ile Gly Ser Ser Glu Trp Leu Leu Ser Ala His Lys Gln
        3365                3370                3375

Leu Thr Gln Asp Met Ser Thr Gln Arg Ala Ile Gln Thr Glu Lys
        3380                3385                3390

Glu Gln Gln Ile Glu Thr Val Cys Glu Thr Ile Gln Asn Leu Val
        3395                3400                3405

Asp Asn Ile Lys Thr Val Leu Thr Gly His Asn Arg Gln Leu Gly
        3410                3415                3420

Asp Val Lys His Leu Leu Lys Ala Met Ala Lys Asp Glu Glu Ala
        3425                3430                3435

Ala Leu Ala Asp Gly Glu Asp Val Pro Tyr Glu Asn Ser Val Arg
        3440                3445                3450

Gln Phe Leu Gly Glu Tyr Lys Ser Trp Gln Asp Asn Ile Gln Thr
        3455                3460                3465

Val Leu Phe Thr Leu Val Gln Ala Met Gly Gln Val Arg Ser Gln
        3470                3475                3480
```

| Glu | His | Val | Glu | Met | Leu | Gln | Glu | Ile | Thr | Pro | Thr | Leu | Lys | Glu |
|  | 3485 |  |  |  | 3490 |  |  |  | 3495 |  |  |  |  |  |

| Leu | Lys | Thr | Gln | Ser | Gln | Ser | Ile | Tyr | Asn | Asn | Leu | Val | Ser | Phe |
|  | 3500 |  |  |  | 3505 |  |  |  | 3510 |  |  |  |  |  |

| Ala | Ser | Pro | Leu | Val | Thr | Asp | Ala | Thr | Asn | Glu | Cys | Ser | Ser | Pro |
|  | 3515 |  |  |  | 3520 |  |  |  | 3525 |  |  |  |  |  |

| Thr | Ser | Ser | Ala | Thr | Tyr | Gln | Pro | Ser | Phe | Ala | Ala | Ala | Val | Arg |
|  | 3530 |  |  |  | 3535 |  |  |  | 3540 |  |  |  |  |  |

| Ser | Asn | Thr | Gly | Gln | Lys | Thr | Gln | Pro | Asp | Val | Met | Ser | Gln | Asn |
|  | 3545 |  |  |  | 3550 |  |  |  | 3555 |  |  |  |  |  |

| Ala | Arg | Lys | Leu | Ile | Gln | Lys | Asn | Leu | Ala | Thr | Ser | Ala | Asp | Thr |
|  | 3560 |  |  |  | 3565 |  |  |  | 3570 |  |  |  |  |  |

| Pro | Pro | Ser | Thr | Val | Pro | Gly | Thr | Gly | Lys | Ser | Val | Ala | Cys | Ser |
|  | 3575 |  |  |  | 3580 |  |  |  | 3585 |  |  |  |  |  |

| Pro | Lys | Lys | Ala | Val | Arg | Asp | Pro | Lys | Thr | Gly | Lys | Ala | Val | Gln |
|  | 3590 |  |  |  | 3595 |  |  |  | 3600 |  |  |  |  |  |

| Glu | Arg | Asn | Ser | Tyr | Ala | Val | Ser | Val | Trp | Lys | Arg | Val | Lys | Ala |
|  | 3605 |  |  |  | 3610 |  |  |  | 3615 |  |  |  |  |  |

| Lys | Leu | Glu | Gly | Arg | Asp | Val | Asp | Pro | Asn | Arg | Arg | Met | Ser | Val |
|  | 3620 |  |  |  | 3625 |  |  |  | 3630 |  |  |  |  |  |

| Ala | Glu | Gln | Val | Asp | Tyr | Val | Ile | Lys | Glu | Ala | Thr | Asn | Leu | Asp |
|  | 3635 |  |  |  | 3640 |  |  |  | 3645 |  |  |  |  |  |

| Asn | Leu | Ala | Gln | Leu | Tyr | Glu | Gly | Trp | Thr | Ala | Trp | Val |
|  | 3650 |  |  |  | 3655 |  |  |  | 3660 |  |

<210> SEQ ID NO 9
<211> LENGTH: 3051
<212> TYPE: DNA
<213> ORGANISM: Homo sapiens

<400> SEQUENCE: 9

```
atgagccaag gccccccac aggggagagc agcgagcccg aagcaaaagt cctccacact      60
aagcggcttt accgggctgt ggtggaggct gtgcatcgac ttgacctcat cctttgcaac    120
aaaactgctt atcaagaagt attcaaacca gaaaacatta gcctgaggaa caagctgcgt    180
gagctctgcg tcaagcttat gttcctgcac ccagtggact atgggagaaa ggctgaggag    240
ctgctgtgga gaaggtata ctatgaagtt atccagctta tcaagactaa caaaaagcac    300
atccacagcc ggagcacttt ggaatgtgcc tacaggacgc acctggttgc tggtattggc    360
ttctaccagc atctccttct ctatatccag tcccactacc agctggaact gcagtgctgc    420
atcgactgga cccatgtcac tgacccctc ataggatgca agaagccagt gtctgcctca    480
gggaaggaga tggattgggc acagatggca tgtcaccgat gtctggtgta tctgggggat    540
ttgtcccgat atcagaatga attagctggc gtagataccg agctgctagc cgagagattt    600
tactaccaag ccctgtcagt agctcctcag attggaatgc ccttcaatca gctgggcacc    660
ctggcaggca gcaagtacta taatgtggaa gccatgtatt gctacctgcg ctgcatccag    720
tcagaagtgt cctttgaggg agcctatggg aacctcaagc ggctgtatga caaggcagcc    780
aaaatgtacc accaactgaa gagtgtgag actcggaaac tgtctcctgg caaaaagcga    840
tgtaaagaca ttaaaaggtt gctagtgaac tttatgtatc tgcaaagcct cctacagccc    900
aaaagcagct ccgtggactc agagctgacc tcactttgcc agtcagtcct ggaggacttc    960
aacctctgcc tcttctacct gccctcctca cccaacctca gcctggccag tgaggatgag   1020
```

| | | | | |
|---|---|---|---|---|
| gaggagtatg | agagtggata | tgctttcctc | ccggaccttc | tcatctttca aatggtcatc | 1080 |
| atctgcctta | tgtgtgtgca | cagcttggag | agagcaggat | ccaagcagta cagtgcagcc | 1140 |
| attgccttca | ccctggccct | cttttcccac | ctcgtcaatc | atgtcaacat acggctgcag | 1200 |
| gctgagctgg | aagagggcga | gaatcccgtc | ccggcattcc | agagtgatgg cacagatgaa | 1260 |
| ccagagtcca | aggaacctgt | ggagaaagag | gaggagccag | atcctgagcc tcctcctgta | 1320 |
| acacccaag | tgggtgaggg | cagaaagagc | cgtaagttct | ctcgcctctc ctgtctccgc | 1380 |
| cgtcgccgcc | acccacccaa | agttggtgat | gacagtgacc | tgagtgaagg ctttgaatcg | 1440 |
| gactcaagcc | atgactcagc | ccgggccagt | gagggctcag | acagtggctc tgacaagagt | 1500 |
| cttgaaggtg | ggggaacggc | ctttgatgct | gaaacagact | cggaaatgaa tagccaggag | 1560 |
| tcccgatcag | acttggaaga | tatggaggaa | gaggagggga | cacggtcacc aaccctggag | 1620 |
| cccctcggg | gcagatcaga | ggctcccgat | tccctcaatg | gcccactggg ccccagtgag | 1680 |
| gctagcattg | ccagcaatct | acaagccatg | tccacccaga | tgttccagac taagcgctgc | 1740 |
| ttccgactgg | cccccacctt | tagcaacctg | ctcctccagc | ccaccaccaa ccctcatacc | 1800 |
| tcggccagcc | acaggccttg | cgtcaatggg | gatgtagaca | agccttcaga gccagcctct | 1860 |
| gaggagggct | ctgagtcgga | ggggagtgag | tccagtggac | gctcctgtcg gaatgagcgc | 1920 |
| agcatccagg | agaagcttca | ggtcctgatg | gccgaaggtc | tgcttcctgc tgtgaaagtc | 1980 |
| ttcctggact | ggcttcggac | caaccccgac | ctcatcatcg | tgtgtgcgca gagctctcaa | 2040 |
| agtctgtgga | accgcctgtc | tgtgttgctg | aatctgttgc | ctgctgctgg tgaactccag | 2100 |
| gagtctggcc | tggccttgtg | tcctgaggtc | caagatcttc | ttgaaggttg tgaactgcct | 2160 |
| gacctcccct | ctagccttct | gctcccagag | gacatggctc | ttcgtaacct gcccccgctc | 2220 |
| cgagctgccc | acagacgctt | taactttgac | acggatcggc | ccctgctcag caccttagag | 2280 |
| gagtcagtgg | tgcgcatctg | ctgcatccgc | agctttggtc | atttcatcgc ccgcctgcaa | 2340 |
| ggcagcatcc | tgcagttcaa | cccagaggtt | ggcatcttcg | tcagcattgc ccagtctgag | 2400 |
| caggagagcc | tgctgcagca | ggcccaggca | cagttccgaa | tggcacagga ggaagctcgt | 2460 |
| cggaacaggc | tcatgagaga | catggctcag | ctacgacttc | agctcgaagt gtctcagctg | 2520 |
| gagggcagcc | tgcagcagcc | caaggcccag | tcagccatgt | ctccctacct cgtccctgac | 2580 |
| acccaggccc | tctgccacca | tctccctgtc | atccgccaac | tggccaccag tggccgcttc | 2640 |
| attgtcatca | tcccaaggac | agtgatcgat | ggcctggatt | tgctgaagaa ggaacaccca | 2700 |
| ggggcccggg | atgggattcg | gtacctggag | gcagagttta | aaaaggaaa caggtacatt | 2760 |
| cgctgccaga | aagaggtggg | aaagagcttt | gagcggcata | agctgaagag gcaggatgca | 2820 |
| gatgcctgga | ctctctataa | gatcctagac | agctgcaaac | agctgactct ggcccagggg | 2880 |
| gcaggtgagg | aggatccgag | tggcatggtg | accatcatca | caggccttcc actggacaac | 2940 |
| cccagcgtgc | tttcaggccc | catgcaggca | gccctgcagg | ccgctgccca cgccagtgtg | 3000 |
| gacatcaaga | atgttctgga | cttctacaag | cagtggaagg | aaattggttg a | 3051 |

<210> SEQ ID NO 10
<211> LENGTH: 1016
<212> TYPE: PRT
<213> ORGANISM: Homo sapiens

<400> SEQUENCE: 10

Met Ser Gln Gly Pro Pro Thr Gly Glu Ser Ser Glu Pro Glu Ala Lys
1               5                   10                  15

```
Val Leu His Thr Lys Arg Leu Tyr Arg Ala Val Glu Ala Val His
            20                  25                  30

Arg Leu Asp Leu Ile Leu Cys Asn Lys Thr Ala Tyr Gln Glu Val Phe
        35                  40                  45

Lys Pro Glu Asn Ile Ser Leu Arg Asn Lys Leu Arg Glu Leu Cys Val
    50                  55                  60

Lys Leu Met Phe Leu His Pro Val Asp Tyr Gly Arg Lys Ala Glu Glu
65                  70                  75                  80

Leu Leu Trp Arg Lys Val Tyr Tyr Glu Val Ile Gln Leu Ile Lys Thr
                85                  90                  95

Asn Lys Lys His Ile His Ser Arg Ser Thr Leu Glu Cys Ala Tyr Arg
            100                 105                 110

Thr His Leu Val Ala Gly Ile Gly Phe Tyr Gln His Leu Leu Leu Tyr
        115                 120                 125

Ile Gln Ser His Tyr Gln Leu Glu Leu Gln Cys Cys Ile Asp Trp Thr
    130                 135                 140

His Val Thr Asp Pro Leu Ile Gly Cys Lys Lys Pro Val Ser Ala Ser
145                 150                 155                 160

Gly Lys Glu Met Asp Trp Ala Gln Met Ala Cys His Arg Cys Leu Val
                165                 170                 175

Tyr Leu Gly Asp Leu Ser Arg Tyr Gln Asn Glu Leu Ala Gly Val Asp
            180                 185                 190

Thr Glu Leu Leu Ala Glu Arg Phe Tyr Gln Ala Leu Ser Val Ala
        195                 200                 205

Pro Gln Ile Gly Met Pro Phe Asn Gln Leu Gly Thr Leu Ala Gly Ser
    210                 215                 220

Lys Tyr Tyr Asn Val Glu Ala Met Tyr Cys Tyr Leu Arg Cys Ile Gln
225                 230                 235                 240

Ser Glu Val Ser Phe Glu Gly Ala Tyr Gly Asn Leu Lys Arg Leu Tyr
                245                 250                 255

Asp Lys Ala Ala Lys Met Tyr His Gln Leu Lys Lys Cys Glu Thr Arg
            260                 265                 270

Lys Leu Ser Pro Gly Lys Lys Arg Cys Lys Asp Ile Lys Arg Leu Leu
        275                 280                 285

Val Asn Phe Met Tyr Leu Gln Ser Leu Leu Gln Pro Lys Ser Ser Ser
    290                 295                 300

Val Asp Ser Glu Leu Thr Ser Leu Cys Gln Ser Val Leu Glu Asp Phe
305                 310                 315                 320

Asn Leu Cys Leu Phe Tyr Leu Pro Ser Ser Pro Asn Leu Ser Leu Ala
                325                 330                 335

Ser Glu Asp Glu Glu Glu Tyr Glu Ser Gly Tyr Ala Phe Leu Pro Asp
            340                 345                 350

Leu Leu Ile Phe Gln Met Val Ile Cys Leu Met Cys Val His Ser
        355                 360                 365

Leu Glu Arg Ala Gly Ser Lys Gln Tyr Ser Ala Ala Ile Ala Phe Thr
    370                 375                 380

Leu Ala Leu Phe Ser His Leu Val Asn His Val Asn Ile Arg Leu Gln
385                 390                 395                 400

Ala Glu Leu Glu Glu Gly Glu Asn Pro Val Pro Ala Phe Gln Ser Asp
                405                 410                 415

Gly Thr Asp Glu Pro Glu Ser Lys Glu Pro Val Glu Lys Glu Glu
            420                 425                 430

Pro Asp Pro Glu Pro Pro Pro Val Thr Pro Gln Val Gly Glu Gly Arg
```

```
                    435                 440                 445
Lys Ser Arg Lys Phe Ser Arg Leu Ser Cys Leu Arg Arg Arg His
    450                 455                 460
Pro Pro Lys Val Gly Asp Asp Ser Asp Leu Ser Glu Gly Phe Glu Ser
465                 470                 475                 480
Asp Ser Ser His Asp Ser Ala Arg Ala Ser Glu Gly Ser Asp Ser Gly
                    485                 490                 495
Ser Asp Lys Ser Leu Glu Gly Gly Thr Ala Phe Asp Ala Glu Thr
                500                 505                 510
Asp Ser Glu Met Asn Ser Gln Glu Ser Arg Ser Asp Leu Glu Asp Met
            515                 520                 525
Glu Glu Glu Glu Gly Thr Arg Ser Pro Thr Leu Glu Pro Pro Arg Gly
        530                 535                 540
Arg Ser Glu Ala Pro Asp Ser Leu Asn Gly Pro Leu Gly Pro Ser Glu
545                 550                 555                 560
Ala Ser Ile Ala Ser Asn Leu Gln Ala Met Ser Thr Gln Met Phe Gln
                    565                 570                 575
Thr Lys Arg Cys Phe Arg Leu Ala Pro Thr Phe Ser Asn Leu Leu Leu
                580                 585                 590
Gln Pro Thr Thr Asn Pro His Thr Ser Ala Ser His Arg Pro Cys Val
            595                 600                 605
Asn Gly Asp Val Asp Lys Pro Ser Glu Pro Ala Ser Glu Glu Gly Ser
        610                 615                 620
Glu Ser Glu Gly Ser Glu Ser Ser Gly Arg Ser Cys Arg Asn Glu Arg
625                 630                 635                 640
Ser Ile Gln Glu Lys Leu Gln Val Leu Met Ala Glu Gly Leu Leu Pro
                    645                 650                 655
Ala Val Lys Val Phe Leu Asp Trp Leu Arg Thr Asn Pro Asp Leu Ile
                660                 665                 670
Ile Val Cys Ala Gln Ser Ser Gln Ser Leu Trp Asn Arg Leu Ser Val
            675                 680                 685
Leu Leu Asn Leu Leu Pro Ala Ala Gly Glu Leu Gln Glu Ser Gly Leu
        690                 695                 700
Ala Leu Cys Pro Glu Val Gln Asp Leu Leu Glu Gly Cys Glu Leu Pro
705                 710                 715                 720
Asp Leu Pro Ser Ser Leu Leu Pro Glu Asp Met Ala Leu Arg Asn
                    725                 730                 735
Leu Pro Pro Leu Arg Ala Ala His Arg Arg Phe Asn Phe Asp Thr Asp
                740                 745                 750
Arg Pro Leu Leu Ser Thr Leu Glu Glu Ser Val Val Arg Ile Cys Cys
            755                 760                 765
Ile Arg Ser Phe Gly His Phe Ile Ala Arg Leu Gln Gly Ser Ile Leu
        770                 775                 780
Gln Phe Asn Pro Glu Val Gly Ile Phe Val Ser Ile Ala Gln Ser Glu
785                 790                 795                 800
Gln Glu Ser Leu Leu Gln Gln Ala Gln Ala Gln Phe Arg Met Ala Gln
                    805                 810                 815
Glu Glu Ala Arg Arg Asn Arg Leu Met Arg Asp Met Ala Gln Leu Arg
                820                 825                 830
Leu Gln Leu Glu Val Ser Gln Leu Glu Gly Ser Leu Gln Gln Pro Lys
            835                 840                 845
Ala Gln Ser Ala Met Ser Pro Tyr Leu Val Pro Asp Thr Gln Ala Leu
        850                 855                 860
```

```
Cys His His Leu Pro Val Ile Arg Gln Leu Ala Thr Ser Gly Arg Phe
865                 870                 875                 880

Ile Val Ile Ile Pro Arg Thr Val Ile Asp Gly Leu Asp Leu Leu Lys
            885                 890                 895

Lys Glu His Pro Gly Ala Arg Asp Gly Ile Arg Tyr Leu Glu Ala Glu
        900                 905                 910

Phe Lys Lys Gly Asn Arg Tyr Ile Arg Cys Gln Lys Glu Val Gly Lys
    915                 920                 925

Ser Phe Glu Arg His Lys Leu Lys Arg Gln Asp Ala Asp Ala Trp Thr
930                 935                 940

Leu Tyr Lys Ile Leu Asp Ser Cys Lys Gln Leu Thr Leu Ala Gln Gly
945                 950                 955                 960

Ala Gly Glu Glu Asp Pro Ser Gly Met Val Thr Ile Ile Thr Gly Leu
                965                 970                 975

Pro Leu Asp Asn Pro Ser Val Leu Ser Gly Pro Met Gln Ala Ala Leu
            980                 985                 990

Gln Ala Ala Ala His Ala Ser Val Asp Ile Lys Asn Val Leu Asp Phe
        995                 1000                1005

Tyr Lys Gln Trp Lys Glu Ile Gly
    1010                1015

<210> SEQ ID NO 11
<211> LENGTH: 1536
<212> TYPE: DNA
<213> ORGANISM: Homo sapiens

<400> SEQUENCE: 11
atggagacat tccctgcagt ggctgagaag gtcctcaagg agttccaggt gttactgcag      60
cacagcccct ctcccattgg aagtacccgc atgctgcagc ttatgaccat caatatgttt     120
gcagtacaca actcccagct gaaagactgc ttctcggagg agtgccgctc tgtgatccag     180
gaacaagccg cagctctggg cttggccatg ttttctctac tggtccgccg ctgcacctgc     240
ttacttaagg agtccgccaa agctcagctg tcctctcctg aggaccagga tgaccaagac     300
gacatcaagg tgtcttcctt tgtcccggac ctgaaggagc tgctcccag tgtcaaagtc      360 tggtcagatt ggatgctcgg ctaccgggac acctggaatc tcctcccac atccctggat      420 ctgccctcgc atgttgctgt ggatgtatgg tcgacgctgg ctgatttctg taacatactg     480
actgcagtga atcagtctga ggtgccactg tacaaggacc cggatgatga cctcacccttc    540 cttatcctgg aagaggatcg gcttctctcg ggctttgtcc ccttgctggc tgcccctcag     600 gaccccctgct acgtggagaa acctcggat aaggttattg cagctgactg caaaagggtc     660
acagtgctga gtattttct ggaagccctt tgtggacaag aagagcctct gctggcattc      720
aagggtggaa agtatgtgtc agtggcaccc gtcccagaca ccatgggaaa ggaaatggga     780
agccaagagg gaacacgact ggaagatgag gaggaggatg tggtgattga agactttgag     840
gaagattcag aggctgaagg cagcggaggc gaggatgaca tcagggagct tcgggccaag     900
aagctggctc tggccaggaa gatagctgag cagcagcgtc gccaggaaaa gatccaggct     960
gtcctggagg accacagtca gatgaggcag atggagctcg aaatcagacc tttgttcctc    1020
gtaccagaca ccaacggctt cattgaccac ctggccagtc tggcgcggct gctggagagc    1080
aggaagtaca tcctggtggt gccctcatc gtgatcaatg agctgacgg cctggccaag     1140 gggcaggaga cagaccaccg ggctgggggc tacgcccgtg tggtacaaga gaaggcccgc    1200
```

```
aagtccatcg agttcctcga gcagcgattc gagagtcggg actcttgcct gcgagccctg    1260
accagccgtg gcaatgaact cgaatccatc gccttccgca gtgaggacat cactggccag    1320
ctgggtaaca acgatgatct catcctgtcc tgctgcctcc actactgcaa agacaaggct    1380
aaggacttca tgcccgccag caaagaggag ccaatccggc tactgcggga ggtggtgctg    1440
ttgacggatg accggaacct gcgtgtgaag gcgctcacaa ggaatgttcc tgtacgggac    1500
atcccagcct tcctcacgtg ggcccaggtg ggctga                              1536
```

<210> SEQ ID NO 12
<211> LENGTH: 511
<212> TYPE: PRT
<213> ORGANISM: Homo sapiens

<400> SEQUENCE: 12

```
Met Glu Thr Phe Pro Ala Val Ala Glu Lys Val Leu Lys Glu Phe Gln
1               5                   10                  15

Val Leu Leu Gln His Ser Pro Ser Pro Ile Gly Ser Thr Arg Met Leu
            20                  25                  30

Gln Leu Met Thr Ile Asn Met Phe Ala Val His Asn Ser Gln Leu Lys
        35                  40                  45

Asp Cys Phe Ser Glu Glu Cys Arg Ser Val Ile Gln Glu Gln Ala Ala
    50                  55                  60

Ala Leu Gly Leu Ala Met Phe Ser Leu Leu Val Arg Arg Cys Thr Cys
65                  70                  75                  80

Leu Leu Lys Glu Ser Ala Lys Ala Gln Leu Ser Ser Pro Glu Asp Gln
                85                  90                  95

Asp Asp Gln Asp Asp Ile Lys Val Ser Ser Phe Val Pro Asp Leu Lys
            100                 105                 110

Glu Leu Leu Pro Ser Val Lys Val Trp Ser Asp Trp Met Leu Gly Tyr
        115                 120                 125

Pro Asp Thr Trp Asn Pro Pro Thr Ser Leu Asp Leu Pro Ser His
    130                 135                 140

Val Ala Val Asp Val Trp Ser Thr Leu Ala Asp Phe Cys Asn Ile Leu
145                 150                 155                 160

Thr Ala Val Asn Gln Ser Glu Val Pro Leu Tyr Lys Asp Pro Asp Asp
                165                 170                 175

Asp Leu Thr Leu Leu Ile Leu Glu Glu Asp Arg Leu Leu Ser Gly Phe
            180                 185                 190

Val Pro Leu Leu Ala Ala Pro Gln Asp Pro Cys Tyr Val Glu Lys Thr
        195                 200                 205

Ser Asp Lys Val Ile Ala Ala Asp Cys Lys Arg Val Thr Val Leu Lys
    210                 215                 220

Tyr Phe Leu Glu Ala Leu Cys Gly Gln Glu Glu Pro Leu Leu Ala Phe
225                 230                 235                 240

Lys Gly Gly Lys Tyr Val Ser Val Ala Pro Val Pro Asp Thr Met Gly
                245                 250                 255

Lys Glu Met Gly Ser Gln Glu Gly Thr Arg Leu Glu Asp Glu Glu Glu
            260                 265                 270

Asp Val Val Ile Glu Asp Phe Glu Glu Asp Ser Glu Ala Glu Gly Ser
        275                 280                 285

Gly Gly Glu Asp Asp Ile Arg Glu Leu Arg Ala Lys Lys Leu Ala Leu
    290                 295                 300

Ala Arg Lys Ile Ala Glu Gln Gln Arg Arg Gln Glu Lys Ile Gln Ala
305                 310                 315                 320
```

```
Val Leu Glu Asp His Ser Gln Met Arg Gln Met Leu Glu Ile Arg
                325                 330                 335

Pro Leu Phe Leu Val Pro Asp Thr Asn Gly Phe Ile Asp His Leu Ala
            340                 345                 350

Ser Leu Ala Arg Leu Leu Glu Ser Arg Lys Tyr Ile Leu Val Val Pro
        355                 360                 365

Leu Ile Val Ile Asn Glu Leu Asp Gly Leu Ala Lys Gly Gln Glu Thr
    370                 375                 380

Asp His Arg Ala Gly Gly Tyr Ala Arg Val Val Gln Glu Lys Ala Arg
385                 390                 395                 400

Lys Ser Ile Glu Phe Leu Glu Gln Arg Phe Glu Ser Arg Asp Ser Cys
                405                 410                 415

Leu Arg Ala Leu Thr Ser Arg Gly Asn Glu Leu Glu Ser Ile Ala Phe
            420                 425                 430

Arg Ser Glu Asp Ile Thr Gly Gln Leu Gly Asn Asn Asp Asp Leu Ile
        435                 440                 445

Leu Ser Cys Cys Leu His Tyr Cys Lys Asp Lys Ala Lys Asp Phe Met
    450                 455                 460

Pro Ala Ser Lys Glu Glu Pro Ile Arg Leu Leu Arg Glu Val Val Leu
465                 470                 475                 480

Leu Thr Asp Asp Arg Asn Leu Arg Val Lys Ala Leu Thr Arg Asn Val
                485                 490                 495

Pro Val Arg Asp Ile Pro Ala Phe Leu Thr Trp Ala Gln Val Gly
            500                 505                 510

<210> SEQ ID NO 13
<211> LENGTH: 3537
<212> TYPE: DNA
<213> ORGANISM: Homo sapiens

<400> SEQUENCE: 13
atgagcctgc agagcgcgca gtacctccgg caggcagaag tcctgaaggc tgacatgaca      60
gattctaagc tgggtccagc tgaagtctgg acatccaggc aggctctgca ggacctgtac     120
cagaaaatgc tagttaccga tttggaatac gctttagaca agaaagtaga acaggatctc     180
tggaatcacg cctttaagaa tcagatcaca acactacaag ccaggcaaa gaatcgagca      240 aatccgaatc ggagtgaagt tcaggcaaac ctttctctgt tcctagaggc agctagtggc     300
ttctatactc agttattaca agaactgtgt acagtattta atgtagattt accatgccgt     360
gtgaagtctt cccaattggg aattatcagc aataaacaga cgcataccag cgccatagtg     420
aagccacagt ctagctcctg ttcctatatc tgccagcact gcctcgtcca ccttggagac     480
attgctcgat acagaaacca gaccagccag gcagagtcct actataggca tgcagctcag     540
cttgtcccct ccaatggtca gccttataat cagttggcta tcttagcttc ttccaaagga     600
gaccatctga ccacaatttt ctactactgc agaagcattg ctgtgaagtt ccctttccca     660
gctgcctcca ctaatctgca aaaagcactt tctaaagcac tggaaagccg agatgaggtg     720
aaaaccaagt ggggtgtttc tgacttcatc aaggccttta ttaaattcca cggtcatgtg     780
tacctgagta gagcttgga aaagttgagc cctcttcgag agaaattgga agaacagttt      840
aagaggctgc tattccaaaa agctttcaac tctcagcagt tagttcatgt cactgtcatt     900
aacctgtttc aacttcatca ccttcgtgac tttagcaatg aaaccgagca gcacacttat     960
agccaagatg agcagctatg ttggacacag ttgctggccc tctttatgtc ttttctcggc    1020
```

```
atcctgtgca agtgtcctct acagaatgag tctcaggagg agtcctacaa tgcctatcct    1080
cttccagcag tcaaggtctc catggactgg ctaagactca gacccagggt ctttcaggag    1140
gcagtggtgg atgaaagaca gtacatttgg ccctggttga tttctcttct gaatagtttc    1200
catccccatg aagaggacct ctcaagtatt agtgcgacac cacttccaga ggagtttgaa    1260
ttacaaggat ttttggcatt gagaccttct ttcaggaact tggattttc caaaggtcac    1320
cagggtatta caggggacaa agaaggccag caacgacgaa tacgacagca acgcttgatc    1380
tctataggca aatggattgc tgataatcag ccaaggctga ttcagtgtga aaatgaggta    1440
gggaaattgt tgtttatcac agaaatccca gaattaatac tggaagaccc cagtgaagcc    1500
aaagagaacc tcattctgca agaaacatct gtgatagagt cgctggctgc agatgggagc    1560
ccagggctaa aatcagtgct atctacaagc cgaaatttaa gcaacaactg tgacacagga    1620
gagaagccag tggttacctt caaagaaaac attaagacac gagaagtgaa cagagaccaa    1680
ggaagaagtt ttcctcccaa agaggtaaaa tcccagacag aactaagaaa gactccagtg    1740
tctgaagcca gaaaaacacc tgtaactcaa accccaactc aagcaagtaa ctcccagttc    1800
atccccattc atcaccctgg agccttccct cctcttccca gcaggccagg gtttccgccc    1860
ccaacatatg ttatccccc gcctgtggca ttttctatgg gctcaggtta caccttccca    1920
gctggtgttt ctgtcccagg aacctttctt cagcctacag ctcactctcc agcaggaaac    1980
caggtgcaag ctgggaaaca gtcccacatt ccttacagcc agcaacgcc ctctggacca    2040
gggccaatga accagggacc tcaacaatca cagccacctt cccagcaacc ccttacatct    2100
ttaccagctc agccaacagc acagtctaca agccagctgc aggttcaagc tctaactcag    2160
caacaacaat cccctacaaa agctgtgccg gctttgggga aaagcccgcc tcaccactct    2220
ggattccagc agtatcaaca ggcagatgcc tccaaacagc tgtggaatcc ccctcaggtt    2280
caaggcccat tagggaaaat tatgcctgtg aaacagccct actaccttca gacccaagac    2340
cccataaaac tgtttgagcc gtcattgcaa cctcctgtaa tgcagcagca gcctctagaa    2400
aaaaaaatga agccttttcc catggagcca tataaccata atccctcaga agtcaaggtc    2460
ccagaattct actgggattc ttcctacagc atggctgata cagatctgt aatggcacag    2520
caagcaaaca tagaccgcag gggcaaacgg tcaccaggaa tcttccgtcc agagcaggat    2580
cctgtaccca gaatgccgtt tgaggacccc aagagctccc ctctgcttcc tccggacctg    2640
ttaaagagtc tggctgcctt ggaggaagag gaagagctga ttttttctaa cactcctgat    2700
ctttacccgg ctctgctggg gcctctcgcc tctcttcctg gacgaagcct ttttaaatcc    2760
ttattggaga agccctcaga gctcatgtca cattcatcct cttttcctgtc cctcaccgga    2820
ttctctctca atcaggaaag atacccaaat aatagtatgt tcaatgaggt atatgggaaa    2880
aacctgacat ccagctccaa agcagaactc agtccctcaa tggcccccca ggaaacatct    2940
ctgtattccc tttttgaagg gactccgtgg tctccatcac ttcctgccag ttcagatcat    3000
tcaacaccag ccagccagtc tcctcattcc tctaacccaa gcagcctacc cagctctcct    3060
ccaacacaca accataattc tgttccattc tccaattttg gacccattgg gactccagat    3120
aacagggata gaaggactgc agatcggtgg aaaactgata agccagccat gggtgggttt    3180
ggcattgatt atctctcagc aacgtcatcc tctgagagca gttggcatca ggccagcact    3240
ccgagtggca cctggacagg ccatggccct tccatggagg attcctctgc tgtcctcatg    3300
gaaagcctaa agaagcaaca gcatgggtc cagcagttgg ggcccaaaag acagtctgaa    3360
gaggaaggaa gcagcagtat ctgcgtagcc cacagagggc ccaggcccct gcccagctgc    3420
```

```
agtctcccag cctccacttt cagagtgaaa ttcaaggcag cacggacatg tgcccatcag    3480
gcacagaaga aaacacgacg tcgtccattt tggaagagac gaaagaaagg aaaataa      3537
```

<210> SEQ ID NO 14
<211> LENGTH: 1178
<212> TYPE: PRT
<213> ORGANISM: Homo sapiens

<400> SEQUENCE: 14

```
Met Ser Leu Gln Ser Ala Gln Tyr Leu Arg Gln Ala Glu Val Leu Lys
1               5                   10                  15

Ala Asp Met Thr Asp Ser Lys Leu Gly Pro Ala Glu Val Trp Thr Ser
            20                  25                  30

Arg Gln Ala Leu Gln Asp Leu Tyr Gln Lys Met Leu Val Thr Asp Leu
        35                  40                  45

Glu Tyr Ala Leu Asp Lys Lys Val Glu Gln Asp Leu Trp Asn His Ala
    50                  55                  60

Phe Lys Asn Gln Ile Thr Thr Leu Gln Gly Gln Ala Lys Asn Arg Ala
65                  70                  75                  80

Asn Pro Asn Arg Ser Glu Val Gln Ala Asn Leu Ser Leu Phe Leu Glu
                85                  90                  95

Ala Ala Ser Gly Phe Tyr Thr Gln Leu Leu Gln Glu Leu Cys Thr Val
            100                 105                 110

Phe Asn Val Asp Leu Pro Cys Arg Val Lys Ser Ser Gln Leu Gly Ile
        115                 120                 125

Ile Ser Asn Lys Gln Thr His Thr Ser Ala Ile Val Lys Pro Gln Ser
    130                 135                 140

Ser Ser Cys Ser Tyr Ile Cys Gln His Cys Leu Val His Leu Gly Asp
145                 150                 155                 160

Ile Ala Arg Tyr Arg Asn Gln Thr Ser Gln Ala Glu Ser Tyr Tyr Arg
                165                 170                 175

His Ala Ala Gln Leu Val Pro Ser Asn Gly Gln Pro Tyr Asn Gln Leu
            180                 185                 190

Ala Ile Leu Ala Ser Ser Lys Gly Asp His Leu Thr Thr Ile Phe Tyr
        195                 200                 205

Tyr Cys Arg Ser Ile Ala Val Lys Phe Pro Phe Pro Ala Ala Ser Thr
    210                 215                 220

Asn Leu Gln Lys Ala Leu Ser Lys Ala Leu Glu Ser Arg Asp Glu Val
225                 230                 235                 240

Lys Thr Lys Trp Gly Val Ser Asp Phe Ile Lys Ala Phe Ile Lys Phe
                245                 250                 255

His Gly His Val Tyr Leu Ser Lys Ser Leu Glu Lys Leu Ser Pro Leu
            260                 265                 270

Arg Glu Lys Leu Glu Glu Gln Phe Lys Arg Leu Leu Phe Gln Lys Ala
        275                 280                 285

Phe Asn Ser Gln Gln Leu Val His Val Thr Val Ile Asn Leu Phe Gln
    290                 295                 300

Leu His His Leu Arg Asp Phe Ser Asn Glu Thr Glu Gln His Thr Tyr
305                 310                 315                 320

Ser Gln Asp Glu Gln Leu Cys Trp Thr Gln Leu Leu Ala Leu Phe Met
                325                 330                 335

Ser Phe Leu Gly Ile Leu Cys Lys Cys Pro Leu Gln Asn Glu Ser Gln
            340                 345                 350
```

Glu Glu Ser Tyr Asn Ala Tyr Pro Leu Pro Ala Val Lys Val Ser Met
            355                 360                 365

Asp Trp Leu Arg Leu Arg Pro Arg Val Phe Gln Glu Ala Val Val Asp
    370                 375                 380

Glu Arg Gln Tyr Ile Trp Pro Trp Leu Ile Ser Leu Leu Asn Ser Phe
385                 390                 395                 400

His Pro His Glu Glu Asp Leu Ser Ser Ile Ser Ala Thr Pro Leu Pro
            405                 410                 415

Glu Glu Phe Glu Leu Gln Gly Phe Leu Ala Leu Arg Pro Ser Phe Arg
            420                 425                 430

Asn Leu Asp Phe Ser Lys Gly His Gln Gly Ile Thr Gly Asp Lys Glu
            435                 440                 445

Gly Gln Gln Arg Arg Ile Arg Gln Gln Arg Leu Ile Ser Ile Gly Lys
450                 455                 460

Trp Ile Ala Asp Asn Gln Pro Arg Leu Ile Gln Cys Glu Asn Glu Val
465                 470                 475                 480

Gly Lys Leu Leu Phe Ile Thr Glu Ile Pro Glu Leu Ile Leu Glu Asp
            485                 490                 495

Pro Ser Glu Ala Lys Glu Asn Leu Ile Leu Gln Glu Thr Ser Val Ile
            500                 505                 510

Glu Ser Leu Ala Ala Asp Gly Ser Pro Gly Leu Lys Ser Val Leu Ser
            515                 520                 525

Thr Ser Arg Asn Leu Ser Asn Cys Asp Thr Gly Glu Lys Pro Val
            530                 535                 540

Val Thr Phe Lys Glu Asn Ile Lys Thr Arg Glu Val Asn Arg Asp Gln
545                 550                 555                 560

Gly Arg Ser Phe Pro Pro Lys Glu Val Lys Ser Gln Thr Glu Leu Arg
                565                 570                 575

Lys Thr Pro Val Ser Glu Ala Arg Lys Thr Pro Val Thr Gln Thr Pro
            580                 585                 590

Thr Gln Ala Ser Asn Ser Gln Phe Ile Pro Ile His His Pro Gly Ala
            595                 600                 605

Phe Pro Pro Leu Pro Ser Arg Pro Gly Phe Pro Pro Thr Tyr Val
    610                 615                 620

Ile Pro Pro Pro Val Ala Phe Ser Met Gly Ser Gly Tyr Thr Phe Pro
625                 630                 635                 640

Ala Gly Val Ser Val Pro Gly Thr Phe Leu Gln Pro Thr Ala His Ser
                645                 650                 655

Pro Ala Gly Asn Gln Val Gln Ala Gly Lys Gln Ser His Ile Pro Tyr
            660                 665                 670

Ser Gln Gln Arg Pro Ser Gly Pro Gly Pro Met Asn Gln Gly Pro Gln
            675                 680                 685

Gln Ser Gln Pro Pro Ser Gln Gln Pro Leu Thr Ser Leu Pro Ala Gln
            690                 695                 700

Pro Thr Ala Gln Ser Thr Ser Gln Leu Gln Val Gln Ala Leu Thr Gln
705                 710                 715                 720

Gln Gln Gln Ser Pro Thr Lys Ala Val Pro Ala Leu Gly Lys Ser Pro
                725                 730                 735

Pro His His Ser Gly Phe Gln Tyr Gln Gln Ala Asp Ala Ser Lys
            740                 745                 750

Gln Leu Trp Asn Pro Gln Val Gln Gly Pro Leu Gly Lys Ile Met
            755                 760                 765

Pro Val Lys Gln Pro Tyr Tyr Leu Gln Thr Gln Asp Pro Ile Lys Leu

```
            770                 775                 780
Phe Glu Pro Ser Leu Gln Pro Pro Val Met Gln Gln Gln Pro Leu Glu
785                 790                 795                 800

Lys Lys Met Lys Pro Phe Pro Met Glu Pro Tyr Asn His Asn Pro Ser
                805                 810                 815

Glu Val Lys Val Pro Glu Phe Tyr Trp Asp Ser Ser Tyr Ser Met Ala
                820                 825                 830

Asp Asn Arg Ser Val Met Ala Gln Gln Ala Asn Ile Asp Arg Arg Gly
                835                 840                 845

Lys Arg Ser Pro Gly Ile Phe Arg Pro Glu Gln Asp Pro Val Pro Arg
    850                 855                 860

Met Pro Phe Glu Asp Pro Lys Ser Ser Pro Leu Leu Pro Pro Asp Leu
865                 870                 875                 880

Leu Lys Ser Leu Ala Ala Leu Glu Glu Glu Glu Leu Ile Phe Ser
                885                 890                 895

Asn Thr Pro Asp Leu Tyr Pro Ala Leu Leu Gly Pro Leu Ala Ser Leu
                900                 905                 910

Pro Gly Arg Ser Leu Phe Lys Ser Leu Leu Glu Lys Pro Ser Glu Leu
                915                 920                 925

Met Ser His Ser Ser Ser Phe Leu Ser Leu Thr Gly Phe Ser Leu Asn
                930                 935                 940

Gln Glu Arg Tyr Pro Asn Asn Ser Met Phe Asn Glu Val Tyr Gly Lys
945                 950                 955                 960

Asn Leu Thr Ser Ser Ser Lys Ala Glu Leu Ser Pro Ser Met Ala Pro
                965                 970                 975

Gln Glu Thr Ser Leu Tyr Ser Leu Phe Glu Gly Thr Pro Trp Ser Pro
                980                 985                 990

Ser Leu Pro Ala Ser Ser Asp His Ser Thr Pro Ala Ser Gln Ser Pro
                995                 1000                1005

His Ser Ser Asn Pro Ser Ser Leu Pro Ser Ser Pro Pro Thr His
    1010                1015                1020

Asn His Asn Ser Val Pro Phe Ser Asn Phe Gly Pro Ile Gly Thr
    1025                1030                1035

Pro Asp Asn Arg Asp Arg Arg Thr Ala Asp Arg Trp Lys Thr Asp
    1040                1045                1050

Lys Pro Ala Met Gly Gly Phe Gly Ile Asp Tyr Leu Ser Ala Thr
    1055                1060                1065

Ser Ser Ser Glu Ser Ser Trp His Gln Ala Ser Thr Pro Ser Gly
    1070                1075                1080

Thr Trp Thr Gly His Gly Pro Ser Met Glu Asp Ser Ser Ala Val
    1085                1090                1095

Leu Met Glu Ser Leu Lys Lys Gln Gln His Gly Val Gln Gln Leu
    1100                1105                1110

Gly Pro Lys Arg Gln Ser Glu Glu Glu Gly Ser Ser Ser Ile Cys
    1115                1120                1125

Val Ala His Arg Gly Pro Arg Pro Leu Pro Ser Cys Ser Leu Pro
    1130                1135                1140

Ala Ser Thr Phe Arg Val Lys Phe Lys Ala Ala Arg Thr Cys Ala
    1145                1150                1155
```

-continued

```
His Gln Ala Gln Lys Lys Thr Arg Arg Arg Pro Phe Trp Lys Arg
    1160            1165                1170
Arg Lys Lys Gly Lys
    1175
```

METHODS OF REDUCING TDP-43-MEDIATED NEURONAL CYTOTOXICITY IN AMYOTROPHIC LATERAL SCLEROSIS BY A UPF1 POLYPEPTIDE OR POLYNUCLEOTIDE

CROSS REFERENCE TO RELATED APPLICATIONS

The present application is the National Stage of International Application PCT/US2013/063858, filed Oct. 8, 2013, which claims the benefit of U.S. provisional application Ser. No. 61/712,322, filed on Oct. 11, 2012, the contents of each of which are herein incorporated by reference in their entirety.

SEQUENCE LISTING

In accordance with 37 CFR 1.52(e)(5), the present specification makes reference to a Sequence Listing submitted electronically in the form of a text file (entitled "Sequence_Listing.txt," created on Dec. 6, 2013, 115 KB in size). The entire contents of the Sequence Listing are herein incorporated by reference, with the intention that, upon publication (including issuance), this incorporated sequence listing will be inserted in the published document immediately before the claims.

BACKGROUND

Amyotrophic lateral sclerosis (ALS, also called Lou Gehrig's disease) is a relentlessly progressive, fatal neurodegenerative disease with a prevalence of about 5 people out of 100,000 each year and an average age of onset of about 60 years. Patients with ALS suffer from degeneration of motor neurons in the brain and spinal cord, which leads to progressive muscular weakness. ALS accounts for about 1/300 to 1/400 of all deaths, which means that about 1,000,000 people now alive in the United States will develop ALS. Death typically occurs 3-5 years after disease onset, due to respiratory paralysis. There is no effective treatment for the disease; the only approved ALS drug (riluzole) extends the lifespan of some ALS patients by only about 3 months. Thus, there remains a need for new therapeutic approaches for treatment of ALS.

SUMMARY

The present disclosure encompasses the surprising discovery that agents involved in nonsense-mediated mRNA decay (NMD) can protect neuronal cells from damage associated with TDP-43 or FUS/TLS. The present invention therefore provides NMD agents for use in medicine, and specifically in treatment or prevention (e.g., delay of onset) of certain neurological disorders including specifically amyotrophic lateral sclerosis (ALS). For example, in various aspects, the present disclosure provides methods of reducing FUS/TLS or TDP-43 toxicity in a neuronal cell or glial cell suffering from or susceptible to such toxicity, comprising providing to the cell (e.g., in vitro or in vivo) a therapeutically effective amount of an NMD polypeptide, thereby reducing the FUS/TLS or TDP-43 toxicity in the cell. In some embodiments, the step of providing comprises administering a composition comprising the NMD polypeptide, a nucleic acid encoding the NMD polypeptide, and/or an activator of the NMD polypeptide. In some embodiments, the NMD polypeptide is a UPF1, UPF2, UPF3, SMG1, SMG5, SMG6, or SMG7 polypeptide. In some embodiments, the cell is a human neuronal cell or a human glial cell.

In various aspects, the present disclosure provides methods of treating a disease, disorder or condition associated with FUS/TLS or TDP-43 toxicity, comprising administering to a subject suffering from or susceptible to the disease, disorder or condition a therapeutically effective amount of an NMD polypeptide, a nucleic acid encoding an NMD polypeptide, and/or an activator or an NMD polypeptide, thereby treating the disease, disorder or condition. In some embodiments, the therapeutically effective amount is correlated with a statistically significant probability of reducing FUS/TLS or TDP-43 toxicity in a neuronal cell or a glial cell. In some embodiments, the therapeutically effective amount is correlated with a statistically significant probability of enhancing mRNA processing in a neuronal cell or a glial cell. In some embodiments, the disease, disorder or condition is not associated with SOD1 toxicity. In some embodiments, the NMD polypeptide, nucleic acid encoding the NMD polypeptide, and/or the activator of the NMD polypeptide is administered into the CNS of the subject, such as by intrathecal injection.

In various aspects, the present disclosure provides methods of treating ALS in a human subject, comprising: administering to a subject suffering from or susceptible to ALS a therapeutically effective amount of an NMD polypeptide, thereby treating the ALS in the subject. In some embodiments, the therapeutically effective amount is correlated with a statistically significant probability of reducing toxicity in a human neuronal cell or a human glial cell. In some embodiments, the toxicity is FUS/TLS or TDP-43 toxicity. In some embodiments, the toxicity is not SOD1 toxicity. In some embodiments, the therapeutically effective amount is correlated with a statistically significant probability of enhancing mRNA processing in a human neuronal cell or a human glial cell.

In various aspects, the present disclosure provides methods of identifying an agent useful in the treatment of ALS, comprising: contacting a population of neuronal cells or glial cells that are suffering from or susceptible to FUS/TLS or TDP-43 toxicity with a test agent; determining a number of viable cells in the population after the contacting step; and comparing the number of viable cells to a control; wherein a test agent that increases the number of viable cells relative to the control is identified as an agent useful in the treatment of ALS. In some embodiments, the neuronal cells or the glial cells are transfected with a nucleic acid encoding FUS/TLS or TDP-43.

In various aspects, the present disclosure provides methods of identifying an agent useful in the treatment of ALS, comprising: contacting a population of neuronal cells or glial cells that are suffering from or susceptible to FUS/TLS or TDP-43 toxicity with a test agent; determining a level of mRNA processing in the population of neuronal cells or glial cells after the contacting step; and comparing the level of mRNA processing to a control; wherein a test agent that increases the level of mRNA processing relative to the control is identified as an agent useful in the treatment of ALS.

In various aspects, the present disclosure provides methods of identifying an agent useful in the treatment of ALS, comprising: contacting a first population of neuronal cells or glial cells that are suffering from or susceptible to FUS/TLS or TDP-43 toxicity with a test agent; determining a first number of viable cells in the first population after the contacting step; administering an NMD polypeptide to a second population of neuronal cells or glial cells that are suffering from or susceptible to FUS/TLS or TDP-43 toxicity; and determining a second number of viable cells in the second population after the administration step; wherein a first number of viable cells that is comparable to the second number of viable cells indicates the test agent is an agent useful in the treatment of ALS.

In various aspect, the present disclosure provides pharmaceutical compositions for treating ALS comprising an NMD polypeptide, a nucleic acid encoding an NMD polypeptide, or an activator of an NMD polypeptide, and a pharmaceutically acceptable excipient. In some embodiments, the pharmaceutical composition further comprising a targeting agent. In some embodiments, upon administration to a subject, the targeting agent selectively targets the composition to the brain.

In various aspect, the present disclosure provides methods of treating ALS in a human subject suffering from or susceptible to ALS, comprising: administering to the human subject a therapeutically effective amount of a UPF1 polypeptide, wherein the therapeutically effective amount is correlated with a statistically significant probability of reducing toxicity in a human neuronal cell or a human glial cell, thereby treating the ALS. In some embodiments, the subject has a mutation in an ALS2 gene, a VAPB gene, a SETX gene, a TDP-43 gene, a FUS/TLS gene, or an OPTN gene. In some embodiments, the subject does not have a mutation in a SOD1 gene.

BRIEF DESCRIPTION OF THE DRAWINGS

The following figures are presented for the purpose of illustration only, and are not intended to be limiting.

FIG. 1A is a graphical representation of cell death of neurons following expression of UPF1. FIG. 1B is a graphical representation of cell death of neurons following expression of TDP-43 and UPF1.

All publications, patent applications, patents, and other references mentioned herein, including GenBank database sequences, are incorporated by reference in their entirety. In case of conflict, the present specification, including definitions, will control. In addition, the materials, methods, and examples are illustrative only and not intended to be limiting. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below.

Other features and advantages of the invention will be apparent from the following detailed description, and from the claims.

DEFINITIONS

In order for the present invention to be more readily understood, certain terms are first defined below. Additional definitions for the following terms and other terms are set forth throughout the specification.

Approximately or about: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Amelioration: As used herein, the term "amelioration" means the prevention, reduction or palliation of a state, or improvement of the state of a subject. Amelioration includes, but does not require, complete recovery or complete prevention of a disease condition.

Characteristic portion: As used herein, the term a "characteristic portion" of a substance, in the broadest sense, is one that shares some degree of sequence or structural identity with respect to the whole substance. In certain embodiments, a characteristic portion shares at least one functional characteristic with the intact substance. For example, in some embodiments, a "characteristic portion" of a polypeptide or protein is one that contains a continuous stretch of amino acids, or a collection of continuous stretches of amino acids, that together are characteristic of a polypeptide or protein. In some embodiments, each such continuous stretch generally contains at least 2, 5, 10, 15, 20, 50, or more amino acids. In some embodiments, such a continuous stretch includes certain residues whose position and identity are fixed; certain residues whose identity tolerates some variability (i.e., one of a few specified residues is accepted); and optionally certain residues whose identity is variable (i.e., any residue is accepted). In general, a characteristic portion of a substance (e.g., of a polypeptide or protein) is one that, in addition to the sequence and/or structural identity specified above, shares at least one functional characteristic with the relevant intact substance. In some embodiments, a characteristic portion may be biologically active.

Characteristic sequence: A "characteristic sequence" is a sequence that is found in all members of a family of polypeptides or nucleic acids, and therefore can be used by those of ordinary skill in the art to define members of the family.

Combination therapy: The term "combination therapy", as used herein, refers to those situations in which two or more different pharmaceutical agents are administered in overlapping regimens so that the subject is simultaneously exposed to both agents. When used in combination therapy, two or more different agents may be administered simultaneously or separately. This administration in combination can include simultaneous administration of the two or more agents in the same dosage form, simultaneous administration in separate dosage forms, and separate administration. That is, two or more agents can be formulated together in the same dosage form and administered simultaneously. Alternatively, two or more agents can be simultaneously administered, wherein the agents are present in separate formulations. In another alternative, a first agent can be administered just followed by one or more additional agents. In the separate administration protocol, two or more agents may be administered a few minutes apart, or a few hours apart, or a few days apart.

Comparable: The term "comparable", as used herein, refers to a system, set of conditions, effects, or results that is/are sufficiently similar to a test system, set of conditions, effects, or results, to permit scientifically legitimate comparison. Those of ordinary skill in the art will appreciate and understand which systems, sets of conditions, effects, or results are sufficiently similar to be "comparable" to any particular test system, set of conditions, effects, or results as described herein.

Correlates: The term "correlates", as used herein, has its ordinary meaning of "showing a correlation with". Those of ordinary skill in the art will appreciate that two features, items or values show a correlation with one another if they show a tendency to appear and/or to vary, together. In some embodiments, a correlation is statistically significant when its p-value is less than 0.05; in some embodiments, a correlation is statistically significant when its p-value is less than 0.01. In some embodiments, correlation is assessed by regression analysis. In some embodiments, a correlation is a correlation coefficient.

Homology: As used herein, the term "homology" refers to the overall relatedness between polymeric molecules, e.g., between nucleic acid molecules (e.g., DNA molecules and/or RNA molecules) and/or between polypeptide molecules. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% identical. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% similar.

Identity: As used herein, the term "identity" refers to the overall relatedness between polymeric molecules, e.g., between nucleic acid molecules (e.g., DNA molecules and/or RNA molecules) and/or between polypeptide molecules. Calculation of the percent identity of two nucleic acid sequences, for example, can be performed by aligning the two sequences for optimal comparison purposes (e.g., gaps can be introduced in one or both of a first and a second nucleic acid sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or substantially 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleotide sequences can be determined using the algorithm of Meyers and Miller (CABIOS, 1989, 4:11-17), which has been incorporated into the ALIGN program (version 2.0) using a PAM 120 weight residue table, a gap length penalty of 12 and a gap penalty of 4. The percent identity between two nucleotide sequences can, alternatively, be determined using the GAP program in the GCG software package using an NWSgapdna.CMP matrix.

Improve, increase, or reduce: As used herein, the terms "improve," "increase" or "reduce," or grammatical equivalents, indicate values that are relative to a reference (e.g., baseline) measurement, such as a measurement taken under comparable conditions (e.g., in the same individual prior to initiation of treatment described herein, or a measurement in a control individual (or multiple control individuals) in the absence of treatment) described herein.

NMD agent: As used herein, the term "NMD agent" refers to an NMD polypeptide, a nucleic acid that encodes an NMD polypeptide, or an agent that increases NMD polypeptide level and/or activity. In some embodiments, an NMD agent is a therapeutic agent.

NMD polypeptide: As used herein, the term "NMD polypeptide" refers to a polypeptide whose amino acid sequence includes at least one characteristic sequence of and/or shows at least 100%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71% or 70% identity with a protein involved in nonsense-mediated mRNA decay (e.g., UPF1, UPF2, UPF3, SMG1, SMG5, SMG6, or SMG7). A wide variety of NMD sequences from flies, vertebrates, and mammals are known in the art, such as those described herein; in some embodiments, an NMD polypeptide shares at least one characteristic sequence of and/or shows the specified degree of overall sequence identity with one of the UPF1, UPF2, UPF3, SMG1, SMG5, SMG6, or SMG7 set forth herein (each of which may be considered a "reference" NMD polypeptide). In some embodiments, an NMD polypeptide as described herein shares at least one biological activity with a reference NMD polypeptide as set forth herein. In some such embodiment, the shared biological activity relates to nonsense-mediated mRNA decay.

Polypeptide: As used herein, a "polypeptide", generally speaking, is a string of at least two amino acids attached to one another by a peptide bond. In some embodiments, a polypeptide may include at least 3-5 amino acids, each of which is attached to others by way of at least one peptide bond. Those of ordinary skill in the art will appreciate that polypeptides sometimes include "non-natural" amino acids or other entities that nonetheless are capable of integrating into a polypeptide chain, optionally.

Protein: As used herein, the term "protein" refers to a polypeptide (i.e., a string of at least two amino acids linked to one another by peptide bonds). Proteins may include moieties other than amino acids (e.g., may be glycoproteins, proteoglycans, etc.) and/or may be otherwise processed or modified. Those of ordinary skill in the art will appreciate that a "protein" can be a complete polypeptide chain as produced by a cell (with or without a signal sequence), or can be a characteristic portion thereof. Those of ordinary skill will appreciate that a protein can sometimes include more than one polypeptide chain, for example linked by one or more disulfide bonds or associated by other means. Polypeptides may contain L-amino acids, D-amino acids, or both and may contain any of a variety of amino acid modifications or analogs known in the art. Useful modifications include, e.g., terminal acetylation, amidation, methylation, etc. In some embodiments, proteins may comprise natural amino acids, non-natural amino acids, synthetic amino acids, and combinations thereof. The term "peptide" is generally used to refer to a polypeptide having a length of less than about 100 amino acids, less than about 50 amino acids, less than 20 amino acids, or less than 10 amino acids.

Providing: As used herein, the term "providing" refers to performing a manipulation that causes an entity of interest to be present at a level and/or with an activity higher than that observed under otherwise comparable conditions prior to or absent the manipulation. In some embodiments, providing consists of or comprises administering the entity itself (alone or as part of a composition); in some embodiment, providing consists of or comprises administering an agent that causes an increase in level and/or activity of the entity of interest. For example, where the entity of interest is or comprises a polypeptide, in some embodiments, "providing" the polypeptide consists of or comprises administering the polypeptide (e.g., to a cell, whether isolated or in an organism); in some embodiments, "providing" the polypeptide consists of or comprises administering a nucleic acid encoding the polypeptide; in some embodiments, "providing" the polypeptide consists of or comprises administering an agent that results in increased expression of an endogenous copy of the polypeptide (e.g., by stimulating one or more of transcription, RNA processing, translation, etc. and/or by inhibiting an inhibitor of one of these).

Reference: A "reference" entity, system, amount, set of conditions, etc., is one against which a test entity, system, amount, set of conditions, etc. is compared as described herein. For example, in some embodiments, a "reference" individual is a control individual who is not suffering from or susceptible to any form of ALS disease; in some embodiments, a "reference" individual is a control individual afflicted with the same form of ALS disease as an individual being treated, and optionally who is about the same age as the individual being treated (to ensure that the stages of the disease in the treated individual and the control individual(s) are comparable).

Subject: As used herein, the term "subject", "individual", or "patient" refers to any organism upon which embodiments of the invention may be used or administered, e.g., for experimental, diagnostic, prophylactic, and/or therapeutic purposes. Typical subjects include animals (e.g., mammals such as mice, rats, rabbits, non-human primates, and humans; insects; worms; etc.).

Target cell or target tissue: As used herein, the terms "target cell" or "target tissue" refers to any cell, tissue, or organism that is affected by ALS to be treated, or any cell, tissue, or organism in which a protein involved in ALS is expressed. In some embodiments, target cells, target tissues, or target organisms include those cells, tissues, or organisms in which there is a detectable or abnormally high amount of FUS or TDP-43 (e.g., comparable to that observed in patients suffering from or susceptible to ALS). In some embodiments, target cells, target tissues, or target organisms include those cells, tissues, or organisms that display a disease-associated pathology, symptom, or feature.

Therapeutic agent: As used herein, the phrase "therapeutic agent" refers to any agent that, when administered to a subject, has a therapeutic effect and/or elicits a desired biological and/or pharmacological effect.

Therapeutic regimen: As used herein, the term "therapeutic regimen" refers to any method used to partially or completely alleviate, ameliorate, relieve, inhibit, prevent, delay onset of, reduce severity of and/or reduce incidence of one or more symptoms or features of a particular disease, disorder, and/or condition. It may include administration of one or more doses, optionally spaced apart by regular or varied time intervals. In some embodiments, a therapeutic regimen is one whose performance is designed to achieve and/or is correlated with achievement of (e.g., across a relevant population of cells, tissues, or organisms) a particular effect, e.g., reduction or elimination of a detrimental condition or disease such as ALS. In some embodiments, treatment includes administration of one or more therapeutic agents either simultaneously, sequentially or at different times, for the same or different amounts of time. In some embodiments, a "treatment regimen" includes genetic methods such as gene therapy, gene ablation or other methods known to induce or reduce expression (e.g., transcription, processing, and/or translation of a particular gene product, such as a primary transcript or mRNA).

Therapeutically effective amount: As used herein, the term "therapeutically effective amount" refers to an amount of a therapeutic agent (e.g., an NMD polypeptide) which confers a therapeutic effect on the treated subject, at a reasonable benefit/risk ratio applicable to any medical treatment. Such a therapeutic effect may be objective (i.e., measurable by some test or marker) or subjective (i.e., subject gives an indication of or feels an effect). In some embodiments, "therapeutically effective amount" refers to an amount of a therapeutic agent or composition effective to treat, ameliorate, or prevent (e.g., delay onset of) a relevant disease or condition, and/or to exhibit a detectable therapeutic or preventative effect, such as by ameliorating symptoms associated with the disease, preventing or delaying onset of the disease, and/or also lessening severity or frequency of symptoms of the disease. A therapeutically effective amount is commonly administered in a dosing regimen that may comprise multiple unit doses. For any particular therapeutic agent, a therapeutically effective amount (and/or an appropriate unit dose within an effective dosing regimen) may vary, for example, depending on route of administration, or on combination with other therapeutic agents. Alternatively or additionally, a specific therapeutically effective amount (and/or unit dose) for any particular patient may depend upon a variety of factors including the particular form of ALS being treated; the severity of the ALS; the activity of the specific therapeutic agent employed; the specific composition employed; the age, body weight, general health, sex and diet of the patient; the time of administration, route of administration, and/or rate of excretion or metabolism of the specific therapeutic agent employed; the duration of the treatment; and like factors as is well known in the medical arts.

Treatment: As used herein, the term "treatment" (also "treat" or "treating") refers to any administration of a therapeutic agent (e.g., an NMD polypeptide) according to a therapeutic regimen that achieves a desired effect in that it partially or completely alleviates, ameliorates, relieves, inhibits, delays onset of, reduces severity of and/or reduces incidence of one or more symptoms or features of a particular disease, disorder, and/or condition (e.g., ALS); in some embodiments, administration of the therapeutic agent according to the therapeutic regimen is correlated with achievement of the desired effect. Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition.

DETAILED DESCRIPTION

The present disclosure encompasses the surprising discovery that UPF1 can prevent neuronal toxicity due to TDP-43 or FUS/TLS. UPF1 is a protein involved in nonsense-mediated mRNA decay (NMD). Accordingly, the disclosure provides, among other things, various therapeutic modalities, including use of NMD polypeptides (e.g., UPF1, UPF2, UPF3, SMG1, SMG5, SMG6, or SMG7) to treat amyotrophic lateral sclerosis (ALS).

Amyotrophic Lateral Sclerosis (ALS)

ALS, which exists as both inherited and random forms, is characterized by degeneration of spinal motor neurons, leading to paralysis and death. While most forms of ALS are sporadic and idiopathic (sALS), about 10% of cases are inherited in a Mendelian fashion and are designated familial ALS (fALS). The present invention provides compositions and methods useful in treating ALS.

Using genetic analysis, several genes that cause fALS have been identified. The first mutations were identified in SOD1, which encodes the ubiquitously expressed copper/zinc superoxide dismutase. These variants are involved in about 20% of fALS cases worldwide (Rosen et al., Nature 362:59-62 (1993)). Other genes involved in fALS include genes coding for alsin (ALS2), vesicle associated membrane protein B (VAPB) (Nishimura et al., Am. J. Hum. Genet. 75:822-831 (2004)), senataxin (SETX) (Chen et al., Am. J. Hum. Genet. 74:1128-1135 (2004)), TAR-DNA-binding protein (TDP-43) (Sreedharan et al., Science 319:1668-1672 (2008)), fused in sarcoma or translocated in liposarcoma (FUS/TLS) (Kwiatkowski et al., Science 323:1205-1208 (2009); Vance et al., Science 323:1208-1211 (2009)), and optineurin (OPTN) (Maruyama et al., Nature 465:223-226 (2010)). FUS/TLS is a nucleic acid binding protein that, when mutated, can cause a subset of fALS and can also increase risk for the sporadic disease. Although FUS/TLS is normally located predominantly in the nucleus, pathogenic mutant forms of FUS/TLS traffic to, and form inclusions in, the cytoplasm of affected spinal motor neurons or glia.

Studies of these genes have provided insight into the biochemical processes that may underlie ALS. Putative mechanisms of toxicity targeting motor neurons include glutamate excitotoxicity, oxidative damage, proteasome inhibition, mitochondrial dysfunction, ER stress, axonal transport defects, growth factor signaling deficiency, and glial cell dysfunction (Rothstein et al., Ann. Neurol. 65:S3-S9 (2009); Ilieva et al., J. Cell Biol. 187:761-772 (2009)).

Nonsense-Mediated mRNA Decay

In mammalian cells, expression of protein-encoding genes requires a series of steps in which pre-mRNA is processed to mRNA in the nucleus before mRNA is translated into protein in the cytoplasm. These steps are subject to quality control to ensure that only completely processed mRNA is exported to the cytoplasm (see, e.g., Maquat et al., Cell 104:173-176 (2001)). One form of quality control, called mRNA surveillance or nonsense-mediated mRNA decay (NMD), degrades mRNAs that prematurely terminate translation more than 50-55 nucleotides upstream of an exon-exon junction as a means to prevent the synthesis of potentially harmful truncated proteins (see, e.g., Maquat, J. Cell Sci. 118:1773-1776 (2005); Nicholson et al., Biochem. Soc. Trans. 38:1615-20 (2010)). A number of proteins are involved in NMD in mammalian cells, including UPF1, UPF2, UPF3, SMG1, SMG5, SMG6, and SMG7 (Wittkopp et al., Mol. Cell. Biol. 29:3517-3528 (2009); Rehwinkel et al, Trends Biochem. Sci. 31:639-646 (2006); Rehwinkel et al., RNA 11:1530-1544 (2005)). According to the present disclosure, any NMD polypeptides can be used to treat ALS in methods described herein.

Nucleic Acid Sequences Encoding NMD Polypeptides

Methods and compositions described herein include, for example, nucleic acids encoding NMD polypeptides (e.g., UPF1, UPF2, UPF3, SMG1, SMG5, SMG6, or SMG7). According to the present disclosure, such nucleic acids (and polypeptides) are useful in the treatment of ALS. In some embodiments, such nucleic acids have or include nucleotide sequences as set forth in SEQ ID NO:1, 3, 5, 7, 9, 11, or 13, or characteristic sequence elements thereof or therein. In some embodiments, useful nucleic acids show at least 100%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, or 70% overall sequence identity with one or more of SEQ ID NO:1, 3, 5, 7, 9, 11, or 13. Alternatively or additionally, in some embodiments, useful nucleic acids include at least 5, 6, 7, 8, 9, 10, 11, 12, 13, 14, 15, 16, 17, 18, 19, 20, 21, 22, 23, 24, 25 or more contiguous residues found in SEQ ID NO:1, 3, 5, 7, 9, 11 or 13. In some embodiments, useful nucleic acids are generated in vitro; in some embodiments, useful nucleic acids are generated in vivo. In some embodiments, useful nucleic acids are generated using genetic engineering techniques (e.g., for production and/or mutagenesis of a reference sequence). To give but a few examples, in some embodiments, nucleic acid variants (e.g., of SEQ ID NO:1, 3, 5, 7, 9, 11 or 13) are generated using techniques such as site directed mutagenesis, random chemical mutagenesis, Exonuclease III deletion procedures, and standard cloning techniques. In some embodiments, useful nucleic acids are generating using chemical synthesis and/or modification procedures.

A variety of methods of making nucleic acids that are "variants" with respect to a reference nucleic acid (e.g., a naturally-occurring or other reference nucleic acid) are well known in the art. These include, for example, procedures in which nucleic acid sequences obtained from natural isolates are modified to generate nucleic acids that encode polypeptides having characteristics that enhance their value in industrial or laboratory applications. In such some embodiments of such procedures, a large number of variant sequences having one or more nucleotide differences with respect to the sequence obtained from the natural isolate are generated and characterized. Typically, these nucleotide differences result in amino acid changes with respect to the polypeptides encoded by the nucleic acids from the natural isolates.

For example, variants can be created using error prone PCR (see, e.g., Leung et al., Technique 1:11-15, 1989; and Caldwell et al., PCR Methods Applic. 2:28-33, 1992). In error prone PCR, PCR is performed under conditions where the copying fidelity of the DNA polymerase is low, such that a high rate of point mutations is obtained along the entire length of the PCR product. Briefly, in such procedures, nucleic acids to be mutagenized are mixed with PCR primers, reaction buffer, $MgCl_2$, $MnCl_2$, Taq polymerase, and an appropriate concentration of dNTPs for achieving a high rate of point mutation along the entire length of the PCR product. For example, the reaction can be performed using 20 fmoles of nucleic acid to be mutagenized, 30 pmole of each PCR primer, a reaction buffer comprising 50 mM KCl, 10 mM Tris HCl (pH 8.3), and 0.01% gelatin, 7 mM $MgCl_2$, 0.5 mM $MnCl_2$, 5 units of Taq polymerase, 0.2 mM dGTP, 0.2 mM dATP, 1 mM dCTP, and 1 mM dTTP. PCR can be performed for 30 cycles of 94° C. for 1 min, 45° C. for 1 min, and 72° C. for 1 min. However, it will be appreciated that these parameters can be varied as appropriate. The mutagenized nucleic acids are then cloned into an appropriate vector and the activities of the polypeptides encoded by the mutagenized nucleic acids are evaluated.

Variants can also be created using oligonucleotide directed mutagenesis to generate site-specific mutations in any cloned DNA of interest. Oligonucleotide mutagenesis is described in, for example, Reidhaar-Olson et al., Science 241:53-57 (1988). Briefly, in such procedures a plurality of double stranded oligonucleotides bearing one or more mutations to be introduced into the cloned DNA are synthesized and inserted into the cloned DNA to be mutagenized. Clones containing the mutagenized DNA are recovered, and the activities of the polypeptides they encode are assessed.

Another method for generating variants is assembly PCR. Assembly PCR involves the assembly of a PCR product from a mixture of small DNA fragments. A large number of different PCR reactions occur in parallel in the same vial, with the products of one reaction priming the products of another reaction. Assembly PCR is described in, for example, U.S. Pat. No. 5,965,408. Still another method of generating variants is sexual PCR mutagenesis. In sexual PCR mutagenesis, forced homologous recombination occurs between DNA molecules of different, but highly related, DNA sequence in vitro as a result of random fragmentation of the DNA molecule based on sequence homology. This is followed by fixation of the crossover by primer extension in a PCR reaction. Sexual PCR mutagenesis is described in, for example, Stemmer, Proc. Natl. Acad. Sci., USA 91:10747-10751 (1994).

Variants can also be created by in vivo mutagenesis. In some embodiments, random mutations in a nucleic acid sequence are generated by propagating the sequence in a bacterial strain, such as an E. coli strain, which carries mutations in one or more of the DNA repair pathways. Such "mutator" strains have a higher random mutation rate than that of a wild-type strain. Propagating a DNA sequence in one of these strains will generate random mutations within the DNA. Mutator strains suitable for use for in vivo mutagenesis are described in, for example, PCT Publication No. WO 91/16427.

Variants can also be generated using cassette mutagenesis. In cassette mutagenesis, a small region of a double stranded DNA molecule is replaced with a synthetic oligonucleotide "cassette" that differs from the native sequence. The oligonucleotide often contains a completely and/or partially randomized native sequence. Recursive ensemble mutagenesis can also be used to generate variants. Recursive ensemble mutagenesis is an algorithm for protein engineering (i.e., protein mutagenesis) developed to produce diverse populations of phenotypically related mutants whose members differ in amino acid sequence. This method uses a feedback mechanism to control successive rounds of combinatorial cassette mutagenesis. Recursive ensemble mutagenesis is described in, for example, Arkin et al., Proc. Natl. Acad. Sci., USA 89:7811-7815 (1992).

In some embodiments, variants are created using exponential ensemble mutagenesis. Exponential ensemble mutagenesis is a process for generating combinatorial libraries with a high percentage of unique and functional mutants, wherein small groups of residues are randomized in parallel to identify, at each altered position, amino acids which lead to functional proteins. Exponential ensemble mutagenesis is described in, for example, Delegrave et al., Biotech. Res. 11:1548-1552 (1993). Random and site-directed mutagenesis are described in, for example, Arnold, Curr. Opin. Biotech. 4:450-455 (1993). In some embodiments, variants are created using shuffling procedures wherein portions of a plurality of nucleic acids that encode distinct polypeptides are fused together to create chimeric nucleic acid sequences that encode chimeric polypeptides as described in, for example, U.S. Pat. Nos. 5,965,408 and 5,939,250.

In some embodiments, nucleic acids for use in accordance with the present disclosure comprise naturally-occurring nucleotide residues. In some embodiments, nucleic acids for use in accordance with the present disclosure include one or more nucleotide "analogs". A nucleotide analog is a nucleotide (i.e., an entity that is incorporated into a nucleic acid polymer without significantly disrupting the structure and/or function of that polymer) whose chemical structure differs from that of reference naturally-occurring ribonucleic or deoxyribonucleic acid residues adenine, guanine, cytosine, thymine, and uracil. In some embodiments, a nucleotide analog differs from its reference nucleotide at the base moiety, sugar moiety, and/or phosphate backbone. In some embodiments, a nucleotide analog contributes to one or more altered features in a nucleic acid polymer into which it is incorporated as compared with a comparable nucleic acid polymer containing its reference nucleotide rather than the analog. For example, in some embodiments, such analog-containing polymer shows improved, stability, hybridization, and/or solubility.

In some embodiments, base moiety alterations found in nucleotide analogs include deoxyuridine for deoxythymidine and 5-methyl-2'-deoxycytidine or 5-bromo-2'-deoxycytidine for deoxycytidine. In some embodiments, sugar moiety alterations found in nucleotide analogs include modification of the 2' hydroxyl of the ribose sugar to form 2'-O-methyl or 2'-O-allyl sugars. In some embodiments, deoxyribose phosphate backbone alterations found in nucleotide analogs include morpholino nucleic acids, in which each base moiety is linked to a six-membered, morpholino ring, or peptide nucleic acids, in which the deoxyphosphate backbone is replaced by a pseudopeptide backbone and the four bases are retained (see, e.g., Summerton et al., Antisense Nucleic Acid Drug Dev. 7:187-195 (1997); Hyrup et al., Bioorgan. Med. Chem. 4:5-23(1996)). Alternatively or additionally, nucleotide analogs may have a phosphorothioate or phosphorodithioate backbone, a phosphoroamidite, or an alkyl phosphotriester backbone.

In certain instances, an NMD polynucleotide or variant for use in accordance with the present disclosure includes alterations to codon(s) to optimize for expression in a particular host cell. For example, for expression in E. coli, an NMP polynucleotide or variant can include one or more altered codons as described in, e.g., Grosjean et al., Gene 18:199-209 (1982).

NMD Polypeptides

In some embodiments, methods and compositions described utilize NMD polypeptides (e.g., UPF1, UPF2, UPF3, SMG1, SMG5, SMG6, or SMG7 polypeptides). According to the present disclosure, such polypeptides are useful in the treatment of ALS. In some embodiments, such polypeptides useful in the practice of the present disclosure have or include amino acid sequences as set forth in SEQ ID NO:2, 4, 6, 8, 10, 12, or 14, or characteristic sequence elements thereof or therein. In some embodiments, useful polypeptides show at least 100%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, or 70% overall sequence identity with one or more of SEQ ID NO:2, 4, 6, 8, 10, 12, or 14. Alternatively or additionally, in some embodiments, useful polypeptides include at least about 5, 10, 15, 20, 25, 30, 35, 40, 45, 50, 75, 100, or 150 or more contiguous amino acid residues found in SEQ ID NO:2, 4, 6, 8, 10, 12, or 14.

In some embodiments, a useful polypeptide differs from its reference polypeptide (e.g., a polypeptide having or including an amino acid sequence as set forth in SEQ ID NO:2, 4, 6, 8, 10, 12, or 14, or characteristic sequence elements thereof or therein) by one or more amino acid residues. For example, in some embodiments, the difference is a conservative or nonconservative substitution of one or more amino acid residues. Conservative substitutions are those that substitute a given amino acid in a polypeptide by another amino acid of similar characteristics. Typical conservative substitutions are the following replacements: replacement of an aliphatic amino acid, such as alanine, valine, leucine, and isoleucine, with another aliphatic amino acid; replacement of a serine with a threonine or vice versa; replacement of an acidic residue, such as aspartic acid and glutamic acid, with another acidic residue; replacement of a residue bearing an amide group, such as asparagine and glutamine, with another residue bearing an amide group; exchange of a basic residue, such as lysine and arginine, with another basic residue; and replacement of an aromatic residue, such as phenylalanine and tyrosine, with another aromatic residue.

In some embodiments, useful NMD polypeptides include a substituent group on one or more amino acid residues. Still other useful polypeptides are associated with (e.g., fused, linked, or coupled to) another moiety (e.g., a peptide or molecule). For example, useful NMD polypeptides can be fused, linked, or coupled to an amino acid sequence (e.g., a leader sequence, a secretory sequence, a proprotein sequence, a second polypeptide, or a sequence that facilitates purification, enrichment, or stabilization of the polypeptide). In certain other embodiments, a polypeptide includes a targeting agent, e.g., a targeting agent described herein.

A variety of methods of making polypeptides are known in the art and can be used to make NMD polypeptides. For example, NMD polypeptides can be recombinantly produced by utilizing a host cell system engineered to express a nucleic acid encoding an NMD polypeptide (e.g., a nucleic acid described herein). Alternatively or additionally, an NMD polypeptide can be produced by activating an endogenous gene (e.g., a nucleic acid encoding an NMD polypeptide present endogenously in a cell). Alternatively or additionally, an NMD polypeptide can be partially or fully prepared by chemical synthesis. Alternatively or additionally, an NMD polypeptide can be purified from natural sources.

Where an NMD polypeptide is recombinantly produced, any expression system can be used. Known expression systems include, without limitation, for example, egg, baculovirus, plant, yeast, or mammalian cells.

In some embodiments, an NMD polypeptide suitable for use in methods described herein are produced in mammalian cells. Non-limiting examples of mammalian cells that can be used include BALB/c mouse myeloma line (NSO/l, ECACC No: 85110503); human retinoblasts (PER.C6, CruCell, Leiden, The Netherlands); monkey kidney CV1 line transformed by SV40 (COS-7, ATCC CRL 1651); human embryonic kidney line (293 or 293 cells subcloned for growth in suspension culture, Graham et al., J. Gen Virol., 36:59, 1977); human fibrosarcoma cell line (e.g., HT1080); baby hamster kidney cells (BHK, ATCC CCL 10); Chinese hamster ovary cells +/−DHFR (CHO, Urlaub and Chasin, Proc. Natl. Acad. Sci. USA, 77:4216, 1980); mouse sertoli cells (TM4, Mather, Biol. Reprod., 23:243-251, 1980); monkey kidney cells (CV1 ATCC CCL 70); African green monkey kidney cells (VERO-76, ATCC CRL-1 587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL 51); TRI cells (Mather et al., Annals N.Y. Acad. Sci., 383:44-68, 1982); MRC 5 cells; FS4 cells; and a human hepatoma line (Hep G2).

Targeting Agents

An NMD agent described herein can be provided in association with and/or can include a targeting agent.

The present disclosure is not limited to any particular targeting agent, and a variety of targeting agents can be used. Examples of such targeting agents include, but are not limited to, nucleic acids (e.g., RNA and DNA), polypeptides (e.g., receptor ligands, signal peptides, avidin, Protein A, and antigen binding proteins), polysaccharides, biotin, hydrophobic groups, hydrophilic groups, drugs, and any organic molecules that bind to target cells or target tissues (e.g., receptors on target cells or target tissues).

Targeting agents can be associated with NMD agents in any of a number of ways. For example, polypeptide targeting agents can be coupled to or fused to an NMD polypeptide. In other embodiments, a targeting agent is associated (e.g., covalently or noncovalently bound) to an NMD agent with either short (e.g., direct coupling), medium (e.g., using small-molecule bifunctional linkers such as SPDP (Pierce Biotechnology, Inc., Rockford, Ill.)), or long (e.g., PEG bifunctional linkers (Nektar Therapeutics, Inc., San Carlos, Calif.)) linkages.

In some instances, targeting agents are or comprise antigen binding proteins or antibodies or binding portions thereof. Antibodies can be generated to allow for specific targeting of antigens or immunogens (e.g., target cell or target tissue specific antigens). Such antibodies include, but are not limited to, polyclonal antibodies; monoclonal antibodies or antigen binding fragments thereof modified antibodies such as chimeric antibodies, reshaped antibodies, humanized antibodies, or fragments thereof (e.g., Fv, Fab', Fab, F(ab')$_2$); or biosynthetic antibodies, e.g., single chain antibodies, single domain antibodies (DAB), Fvs, or single chain Fvs (scFv) (see, e.g., in Harlow et al., Using Antibodies: A Laboratory Manual: Portable Protocol I. Cold Spring Harbor Laboratory (Dec. 1, 1998); Zola, Monoclonal Antibodies: Preparation and Use of Monoclonal Antibodies and Engineered Antibody Derivatives, Springer Verlag (Dec. 15, 2000; 1st edition)). Antibody attachment can be performed by any known method e.g., through standard covalent binding to free amine groups (see, e.g., Torchilin et al., Hybridoma 6:229-240 (1987); Torchilin et al, Biochim. Biophys. Acta 1511:397-411 (2001); Masuko et al., Biomacromol. 6:800-884 (2005)).

In some instances, a targeting agent is or comprises a nucleic acid (e.g., RNA or DNA). In some examples, nucleic acid targeting agents are designed to hybridize by base pairing to a particular nucleic acid (e.g., chromosomal DNA, mRNA, or ribosomal RNA). In some situations, nucleic acid targeting agents bind a ligand on a target cell or target tissue. For example, a nucleic acid can bind human nerve growth factor (Binkley et al., Nuc. Acids Res. 23:3198-205 (1995)). Nucleic acids that bind ligands can be identified by known methods, such as SELEX procedures (see, e.g., U.S. Pat. Nos. 5,475,096; 5,270,163; and 5,475,096; and WO 97/38134; WO 98/33941; and WO 99/07724). In some embodiments, targeting agents can be or comprise aptamers, for example that bind to particular sequences.

In some embodiments, a targeting agent binds to a receptor on the surface of a brain cell to facilitate cellular uptake. For example, a targeting agent can be mannose-6-phosphate (M6P), bis-phosphorylated oligosaccharides, or IGF-II, which are useful for targeting the cation-independent mannose-6-phosphate receptor (CI-MPR) on a brain cell. In some embodiments, a targeting agent is or comprises ascorbate, which is taken up by a sodium-dependent-vitamin C transporter (SVCT2), (see, e.g., Tsukaguchi et al., Nature 399:70-75 (1999)), which is useful for targeting to a brain cell.

Therapeutic Administration

NMD agents (e.g., NMD polynucleotides, a nucleic acid encoding an NMD polypeptide, or an agent that increases NMD polypeptide level and/or activity) described herein can be used to treat ALS, e.g., subjects suffering from or susceptible to ALS. The route and/or mode of administration of an NMD agent described herein can vary depending upon the desired results. One with skill in the art, i.e., a physician, is aware that dosage regimens can be adjusted to provide the desired response, e.g., a therapeutic response.

Methods of administration include, but are not limited to, intradermal, intramuscular, intraperitoneal, intravenous, subcutaneous, intranasal, epidural, oral, sublingual, intracerebral, intrathecal, intravaginal, transdermal, rectal, by inhalation, or topical, particularly to the ears, nose, eyes, or skin. The mode of administration is left to the discretion of the practitioner.

In some instances, an NMD agent described herein (e.g., a pharmaceutical formulation of an NMD agent) can effectively cross the blood brain barrier and enter the brain. In other instances, an NMD agent can be delivered using techniques designed to permit or to enhance the ability of the formulation to cross the blood-brain barrier. Such techniques are known in the art (e.g., WO 89/10134; Cloughesy et al., J. Neurooncol. 26:125-132 (1995); and Begley, J. Pharm. Pharmacol. 48:136-146 (1996)). Components of a formulation can also be modified (e.g., chemically) using methods known in the art to facilitate their entry into the CNS.

For example, physical methods of transporting compositions across the blood-brain barrier include, but are not limited to, circumventing the blood-brain barrier entirely, or by creating openings in the blood-brain barrier. Circumvention methods include, but are not limited to, direct injection into the brain (see e.g., Papanastassiou et al., Gene Therapy 9: 398-406 (2002)) and implanting a delivery device in the brain (see e.g., Gill et al., Nature Med. 9: 589-595 (2003); and Gliadel Wafers™, Guildford Pharmaceutical). Methods of creating openings in the barrier include, but are not limited to, ultrasound (see e.g., U.S. Patent Publication No. 2002/0038086), osmotic pressure (e.g., by administration of hypertonic mannitol (Neuwelt, E. A., Implication of the Blood-Brain Barrier and its Manipulation, Vols 1 & 2, Plenum Press, N.Y. (1989))), permeabilization by, e.g., bradykinin or permeabilizer A-7 (see, e.g., U.S. Pat. Nos. 5,112,596, 5,268,164, 5,506,206, and 5,686,416), and transfection of neurons that straddle the blood-brain barrier with vectors containing genes encoding an NMD agent (see, e.g., U.S. Patent Publ. No. 20030083299).

Lipid-based methods can also be used to transport an NMD agent across the blood-brain barrier. Exemplary, non-limiting methods include encapsulating an NMD agent in liposomes that are coupled to a targeting agent described herein (e.g., an antibody that binds to receptors on vascular endothelium of the blood-brain barrier (see, e.g., U.S. Patent Publ. No. 20020025313). In certain other embodiments, a targeting agent is coated in low-density lipoprotein particles (see, e.g., U.S. Patent Publ. No. 20040204354) or apolipoprotein E (see, e.g., U.S. Patent Publ. No. 20040131692).

In some embodiments, an NMD agent is delivered to the CNS of a subject, e.g., by administering into the cerebrospinal fluid (CSF) of a subject in need of treatment. As used herein, intrathecal administration (also referred to as intrathecal injection) refers to an injection into the spinal canal (intrathecal space surrounding the spinal cord). Various techniques may be used including, without limitation, lateral cerebroventricular injection through a burrhole or cisternal or lumbar puncture or the like. Exemplary methods are described in Lazorthes et al., Adv. Tech. Stand. Neurosurg. 18:143-192 (1991), and Omaya, Cancer Drug Deliv. 1:169-179 (1984).

In some instances, an NMD agent described herein is administered locally. This can be achieved, for example, by local infusion during surgery, topical application (e.g., in a cream or lotion), by injection, by means of a catheter, by means of a suppository or enema, or by means of an implant, said implant being of a porous, non-porous, or gelatinous material, including membranes, such as sialastic membranes, or fibers. In some situations, an NMD agent described herein is introduced into the central nervous system, circulatory system or gastrointestinal tract by any suitable route, including intraventricular injection, intrathecal injection, paraspinal injection, epidural injection, enema, and by injection adjacent to a peripheral nerve.

Specifically, various devices can be used for intrathecal delivery of NMD agents described herein. In some embodiments, a device for intrathecal administration contains a fluid access port (e.g., injectable port); a hollow body (e.g., catheter) having a first flow orifice in fluid communication with the fluid access port and a second flow orifice configured for insertion into spinal cord; and a securing mechanism for securing the insertion of the hollow body in the spinal cord. Various other devices may be used to effect intrathecal administration of a therapeutic composition. For example, formulations containing NMD agents can be administered using an Ommaya reservoir that is in common use for intrathecally administering drugs for meningeal carcinomatosis (Lancet 2: 983-84, 1963). More specifically, in this method, a ventricular tube is inserted through a hole formed in the anterior horn and is connected to an Ommaya reservoir installed under the scalp, and the reservoir is subcutaneously punctured to intrathecally deliver an NMD agent, which is injected into the reservoir. Other devices for intrathecal administration of therapeutic compositions or formulations to an individual are described in U.S. Pat. No. 6,217,552. Alternatively, an NMD agent can be intrathecally given, for example, by a single injection, or continuous infusion. It should be understood that the dosage treatment may be in the form of a single dose administration or multiple doses.

In some embodiments, intrathecal administration can be performed by either lumbar puncture (i.e., slow bolus) or via a port-catheter delivery system (i.e., infusion or bolus). Relative to intravenous administration, a single dose volume suitable for intrathecal administration is typically small. Typically, intrathecal delivery maintains the balance of the composition of the CSF as well as the intracranial pressure of the subject. In some embodiments, intrathecal delivery is performed absent the corresponding removal of CSF from a subject. In some embodiments, a suitable single dose volume may be e.g., less than about 10 ml, 8 ml, 6 ml, 5 ml, 4 ml, 3 ml, 2 ml, 1.5 ml, 1 ml, or 0.5 ml. In some embodiments, a suitable single dose volume may be about 0.5-5 ml, 0.5-4 ml, 0.5-3 ml, 0.5-2 ml, 0.5-1 ml, 1-3 ml, 1-5 ml, 1.5-3 ml, 1-4 ml, or 0.5-1.5 ml. In some embodiments, intrathecal delivery according to the present invention involves a step of removing a desired amount of CSF first. In some embodiments, less than about 10 ml (e.g., less than about 9 ml, 8 ml, 7 ml, 6 ml, 5 ml, 4 ml, 3 ml, 2 ml, 1 ml) of CSF is first removed before intrathecal administration. In those cases, a suitable single dose volume may be e.g., more than about 3 ml, 4 ml, 5 ml, 6 ml, 7 ml, 8 ml, 9 ml, 10 ml, 15 ml, or 20 ml.

Pulmonary administration can also be employed, e.g., by use of an inhaler or nebulizer, and formulation with an aerosolizing agent, or via perfusion in a fluorocarbon or synthetic pulmonary surfactant.

An NMD agent described herein can be formulated as a pharmaceutical composition that includes a suitable amount of a physiologically acceptable excipient (see, e.g., Remington's Pharmaceutical Sciences pp. 1447-1676 (Alfonso R. Gennaro, ed., 19th ed. 1995)). Such physiologically acceptable excipients can be, e.g., liquids, such as water and oils, including those of petroleum, animal, vegetable, or synthetic origin, such as peanut oil, soybean oil, mineral oil, sesame oil and the like. The physiologically acceptable excipients can be saline, gum acacia, gelatin, starch paste, talc, keratin, colloidal silica, urea and the like. In addition, auxiliary, stabilizing, thickening, lubricating, and coloring agents can be used. In one situation, the physiologically acceptable excipients are sterile when administered to an animal. The physiologically acceptable excipient should be stable under the conditions of manufacture and storage and should be preserved against the contaminating action of microorganisms. Saline solutions and aqueous dextrose and glycerol solutions can also be employed as liquid excipients, particularly for injectable solutions. Suitable physiologically acceptable excipients also include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Other examples of suitable physiologically acceptable excipients are described in Remington's Pharmaceutical Sciences pp. 1447-1676 (Alfonso R. Gennaro, ed., 19th ed. 1995). The pharmaceutical compositions, if desired, can also contain minor amounts of wetting or emulsifying agents, or pH buffering agents.

Liquid carriers can be used in preparing solutions, suspensions, emulsions, syrups, and elixirs. An NMD agent described herein can be suspended in a pharmaceutically acceptable liquid carrier such as water, an organic solvent, a mixture of both, or pharmaceutically acceptable oils or fat. The liquid carrier can contain other suitable pharmaceutical additives including solubilizers, emulsifiers, buffers, preservatives, sweeteners, flavoring agents, suspending agents, thickening agents, colors, viscosity regulators, stabilizers, or osmo-regulators. Suitable examples of liquid carriers for oral and parenteral administration include water (particular containing additives described herein, e.g., cellulose derivatives, including sodium carboxymethyl cellulose solution), alcohols (including monohydric alcohols and polyhydric alcohols, e.g., glycols) and their derivatives, and oils (e.g., fractionated coconut oil and arachis oil). For parenteral administration the carrier can also be an oily ester such as ethyl oleate and isopropyl myristate. The liquid carriers can be in sterile liquid form for administration. The liquid carrier for pressurized compositions can be halogenated hydrocarbon or other pharmaceutically acceptable propellant.

In other instances, an NMD agent described herein is formulated for intravenous administration. Compositions for intravenous administration can comprise a sterile isotonic aqueous buffer. The compositions can also include a solubilizing agent. Compositions for intravenous administration can optionally include a local anesthetic such as lidocaine to lessen pain at the site of the injection. The ingredients can be supplied either separately or mixed together in unit dosage form, for example, as a dry lyophilized powder or water-free concentrate in a hermetically sealed container such as an ampule or sachette indicating the quantity of active agent. Where an NMD agent described herein is administered by infusion, it can be dispensed, for example, with an infusion bottle containing sterile pharmaceutical grade water or saline. Where an NMD agent described herein is administered by injection, an ampule of sterile water for injection or saline can be provided so that the ingredients can be mixed prior to administration.

An NMD agent described herein can be administered rectally or vaginally in the form of a conventional suppository. Suppository formulations can be made using methods known to those in the art from traditional materials, including cocoa butter, with or without the addition of waxes to alter the suppository's melting point, and glycerin. Water-soluble suppository bases, such as polyethylene glycols of various molecular weights, can also be used.

The amount of an NMD agent described herein that is effective for treating ALS can be determined using standard clinical techniques known to those with skill in the art. In addition, in vitro or in vivo assays can optionally be employed to help identify optimal dosage ranges. The precise dose to be employed can also depend on the route of administration, the condition, the seriousness of the condition being treated, as well as various physical factors related to the individual being treated, and can be decided according to the judgment of a health-care practitioner.

Compositions described herein (e.g., therapeutically effective amounts of compositions described herein) can be administered as single administrations or as multiple administrations. Such compositions can be administered at regular intervals, depending on the nature, severity and extent of the subject's condition (e.g., ALS). In some embodiments, a therapeutically effective amount of a therapeutic agent (e.g., an NMD agent) is administered intrathecally periodically at regular intervals (e.g., once every year, once every six months, once every five months, once every three months, bimonthly (once every two months), monthly (once every month), biweekly (once every two weeks), or weekly).

As used herein, the term "therapeutically effective amount" is largely determined based on the total amount of the therapeutic agent contained in pharmaceutical compositions described herein. Generally, a therapeutically effective amount is sufficient to achieve a meaningful benefit to a subject (e.g., treating, modulating, curing, preventing and/or ameliorating ALS). For example, a therapeutically effective amount can be an amount sufficient to achieve a desired therapeutic and/or prophylactic effect, such as an amount sufficient to treat ALS or the symptoms thereof. Generally, the amount of a therapeutic agent (e.g., an NMD agent) administered to a subject in need thereof will depend upon the characteristics of the subject. Such characteristics include the condition, disease severity, general health, age, sex and body weight of the subject. One of ordinary skill in the art will be readily able to determine appropriate dosages depending on these and other related factors. In addition, both objective and subjective assays can optionally be employed to identify optimal dosage ranges. A therapeutically effective amount can be administered in a dosing regimen that can include multiple unit doses.

In some embodiments, a therapeutically effective dose ranges from about 0.005 mg/kg brain weight to 500 mg/kg brain weight, e.g., from about 0.005 mg/kg brain weight to 400 mg/kg brain weight, from about 0.005 mg/kg brain weight to 300 mg/kg brain weight, from about 0.005 mg/kg brain weight to 200 mg/kg brain weight, from about 0.005 mg/kg brain weight to 100 mg/kg brain weight, from about 0.005 mg/kg brain weight to 90 mg/kg brain weight, from about 0.005 mg/kg brain weight to 80 mg/kg brain weight, from about 0.005 mg/kg brain weight to 70 mg/kg brain weight, from about 0.005 mg/kg brain weight to 60 mg/kg brain weight, from about 0.005 mg/kg brain weight to 50 mg/kg brain weight, from about 0.005 mg/kg brain weight to 40 mg/kg brain weight, from about 0.005 mg/kg brain weight to 30 mg/kg brain weight, from about 0.005 mg/kg brain weight to 25 mg/kg brain weight, from about 0.005 mg/kg brain weight to 20 mg/kg brain weight, from about 0.005 mg/kg brain weight to 15 mg/kg brain weight, from about 0.005 mg/kg brain weight to 10 mg/kg brain weight.

In some embodiments, a therapeutically effective dose is greater than about 0.1 mg/kg brain weight, greater than about 0.5 mg/kg brain weight, greater than about 1.0 mg/kg brain weight, greater than about 3 mg/kg brain weight, greater than about 5 mg/kg brain weight, greater than about 10 mg/kg brain weight, greater than about 15 mg/kg brain weight, greater than about 20 mg/kg brain weight, greater than about 30 mg/kg brain weight, greater than about 40 mg/kg brain weight, greater than about 50 mg/kg brain weight, greater than about 60 mg/kg brain weight, greater than about 70 mg/kg brain weight, greater than about 80 mg/kg brain weight, greater than about 90 mg/kg brain weight, greater than about 100 mg/kg brain weight, greater than about 150 mg/kg brain weight, greater than about 200 mg/kg brain weight, greater than about 250 mg/kg brain weight, greater than about 300 mg/kg brain weight, greater than about 350 mg/kg brain weight, greater than about 400 mg/kg brain weight, greater than about 450 mg/kg brain weight, greater than about 500 mg/kg brain weight.

In some embodiments, a therapeutically effective dose can be expressed as mg/kg body weight. As one skilled in the art would appreciate, brain weights and body weights can be correlated (see, e.g., Dekaban, Ann. Neurol. 4:345-56 (1978)).

In some embodiments, a therapeutically effective dose can be expressed as mg/15 cc of CSF. As one skilled in the art would appreciate, therapeutically effective doses based on brain weights and body weights can be converted to mg/15 cc of CSF. For example, the volume of CSF in adult humans is approximately 150 mL (Johanson et al., Cerebrospinal Fluid Res. 14:5:10 (2008)). Therefore, single dose injections of 0.1 mg to 50 mg protein to adults would be approximately 0.01 mg/15 cc of CSF (0.1 mg) to 5.0 mg/15 cc of CSF (50 mg) doses in adults.

It is to be further understood that for any particular subject, specific dosage regimens can be adjusted over time according to the individual need and the professional judgment of the person administering or supervising the administration of an NMD agent and that dosage ranges set forth herein are exemplary only and are not intended to limit the scope or practice of the claimed invention.

In some instances, a pharmaceutical composition described herein is in unit dosage form, e.g., as a tablet, capsule, powder, solution, suspension, emulsion, granule, or suppository. In such form, the pharmaceutical composition can be sub-divided into unit doses containing appropriate quantities of an NMD agent described herein. The unit dosage form can be a packaged pharmaceutical composition, for example, packeted powders, vials, ampoules, pre-filled syringes or sachets containing liquids. The unit dosage form can be, for example, a capsule or tablet itself, or it can be the appropriate number of any such compositions in package form. Such unit dosage form can contain from about 1 mg/kg to about 250 mg/kg, and can be given in a single dose or in two or more divided doses.

Gene Therapy

In embodiments in which an NMD agent consists of or comprises a nucleic acid encoding an NMD polypeptide, the present disclosure includes methods of administering such nucleic acid to a subject to treat ALS.

In some embodiments, a nucleic acid encoding an NMD polypeptide is inserted into a viral vector for delivery to a subject. For example, retrovirus vectors can be used as a recombinant delivery system for transferring nucleic acids encoding NMD polypeptides vivo (see, e.g., Dropulic, Hum. Gene Ther. 22:649-57 (2011); and Kumar et al., Curr. Gene Ther. 11:144-53 (2011)). Retroviruses useful in methods of the present disclosure include, but are not limited to, murine leukemia virus (MLV), human immunodeficiency virus (HIV), equine infectious anaemia virus (EIAV), mouse mammary tumour virus (MMTV), Rous sarcoma virus (RSV), Fujinami sarcoma virus (FuSV), FBR murine osteosarcoma virus (FBR MSV), Moloney murine sarcoma virus (Mo-MSV), Abelson murine leukemia virus (A-MLV), Avian myelocytomatosis virus-29 (MC29), Avian erythroblastosis virus (AEV) and all other retroviridiae including lentiviruses (see, e.g., Coffin et al., "Retroviruses", 1997 Cold Spring Harbor Laboratory Press Eds: J M Coffin, S M Hughes, H E Varmus, pp 758-763)). A replication defective retrovirus can be packaged into virions that can be used to infect a target cell through the use of a helper virus by standard techniques (see, e.g., Current Protocols in Molecular Biology, Ausubel, F. M. et al. (eds.) Greene Publishing Associates, (1989), Sections 9.10-9.14).

In other embodiments, adenovirus-derived vectors are used to deliver nucleic acids encoding NMD polypeptides. The genome of an adenovirus can be manipulated such that it encodes and expresses an NMD polypeptide, but is inactivated in terms of its ability to replicate in a normal lytic viral life cycle (see, e.g., Berkner et al. (1988) BioTechniques 6:616; Rosenfeld et al. (1991) Science 252:431-434; and Rosenfeld et al. (1992) Cell 68:143-155). Suitable adenoviral vectors useful in the methods of the present disclosure include those derived from the adenovirus strain Ad type 5 d1324 or other strains of adenovirus (e.g., Ad2, Ad3, Ad7 etc.).

In some embodiments, an adeno-associated virus (AAV) is used to deliver a nucleic acid encoding an NMD polypeptide (see, e.g., Muzyczka et al. (1992) Curr. Topics in Micro. and Immunol. 158:97-129). A variety of nucleic acids have been introduced into different cell types using AAV vectors (see, e.g., Hermonat et al. (1984) Proc. Natl. Acad. Sci. USA 81:6466-6470; Tratschin et al. (1985) Mol. Cell. Biol. 4:2072-2081; Wondisford et al. (1988) Mol. Endocrinol. 2:32-39; Tratschin et al. (1984) J. Virol. 51:611-619; and Flotte et al. (1993) J. Biol. Chem. 268:3781-3790). Particularly useful AAVs include those that normally infect humans (e.g., serotypes 1, 2, 3A, 3B, 4, 5, and 6) or primates (e.g., serotypes 1 and 4).

In other embodiments, non-viral methods are useful to deliver a nucleic acid encoding an NMD polypeptide to a subject. Such nonviral methods of gene transfer can exploit mechanisms normally used by mammalian cells for uptake and intracellular transport of macromolecules. For example, liposomal delivery systems, poly-lysine conjugates, and artificial viral envelopes can be used. In some embodiments, a nucleic acid encoding an NMD polypeptide is entrapped in liposomes bearing positive charges on their surface (e.g., lipofectins). In some embodiments, a liposome can be conjugated to a targeting agent described herein (see, e.g., Mizuno et al. (1992) No Shinkei Geka 20:547-551).

Certain cationic polymers ("complexation agents") known to spontaneously bind to and condense nucleic acids into nanoparticles can also be used including, e.g., naturally occurring proteins, peptides, or derivatives, as well as synthetic cationic polymers such as polyethylenimine (PEI), polylysine (PLL), etc. Many useful polymers contain both chargeable amino groups, to allow for ionic interaction with negatively charged DNA phosphate, and a degradable region, such as a hydrolyzable ester linkage. Examples of these include, without limitation, poly(alpha-(4-aminobutyl)-L-glycolic acid), network poly(amino ester), and poly (beta-amino esters). Such complexation agents can protect DNA against degradation, e.g., by nucleases, serum components, etc., and create a less negative surface charge, which may facilitate passage through hydrophobic membranes (e.g., cytoplasmic, lysosomal, endosomal, nuclear) of the cell. Certain complexation agents facilitate intracellular trafficking events such as endosomal escape, cytoplasmic transport, and nuclear entry, and can dissociate from the nucleic acid.

Cell-Based Therapy

An NMD polynucleotide can also be advantageously provided to a cell ex vivo, followed by administration of the living cell to the subject. In some embodiments, primary or secondary cells are genetically engineered to express an NMD polypeptide. Such cells can be obtained from a variety of tissues and include cell types which can be maintained propagated in culture. For example, primary and secondary cells include fibroblasts, endothelial cells, glial cells, and neural cells. In some embodiments, primary cells are obtained from an individual to whom a genetically engineered primary or secondary cells is to be administered. Primary cells can also be obtained from a donor (other than the recipient) of the same species or another species (e.g., mouse, rat, rabbit, cat, dog, pig, cow, bird, sheep, goat, horse).

Primary or secondary cells (e.g., of vertebrate or mammalian origin) can be transfected with a nucleic acid encoding an NMD polypeptide. In some embodiments, a cell is transfected with an exogenous nucleic acid sequence that includes a nucleic acid encoding an NMD polypeptide and an additional nucleic acid sequence (e.g., a regulatory sequence, e.g., a promoter, which causes expression, e.g., inducible expression or upregulation, of an endogenous NMD sequence). Transfected primary or secondary cells may also include DNA encoding a selectable marker which confers a selectable phenotype upon them, facilitating their identification and isolation.

Methods for treating disease by implanting a cell that has been modified to express a recombinant protein are also well known. See, for example, U.S. Pat. No. 5,399,346, disclosing methods for introducing a nucleic acid into a primary human cell for introduction into a human. Although use of human cells for ex vivo therapy is preferred in some embodiments, other cells such as bacterial cells may be implanted in a subject's vasculature, continuously releasing a therapeutic agent. See, for example, U.S. Pat. Nos. 4,309, 776 and 5,704,910.

Kits

An NMD agent described herein (e.g., a pharmaceutical composition comprising an NMD agent) can be provided in a kit. In some instances, the kit includes (a) a container that contains an NMD agent described herein (e.g., a pharmaceutical composition comprising an NMD agent) and, optionally (b) informational material. The informational material can be descriptive, instructional, marketing or other material that relates to the methods described herein and/or the use of an NMD agent, e.g., for therapeutic benefit.

The informational material of the kits is not limited in its form. In some instances, the informational material can include information about production of an NMD agent, molecular weight of an NMD agent, concentration, date of expiration, batch or production site information, and so forth. In other situations, the informational material relates to methods of administering an NMD agent, e.g., in a suitable amount, manner, or mode of administration (e.g., a dose, dosage form, or mode of administration described herein). The method can be a method of treating a subject having ALS.

In some cases, the informational material, e.g., instructions, is provided in printed matter, e.g., a printed text, drawing, and/or photograph, e.g., a label or printed sheet. The informational material can also be provided in other formats, such as Braille, computer readable material, video recording, or audio recording. In other instances, the informational material of the kit is contact information, e.g., a physical address, email address, website, or telephone number, where a user of the kit can obtain substantive information about an NMD agent therein and/or their use in the methods described herein. The informational material can also be provided in any combination of formats.

In addition to an NMD agent, the kit can include other ingredients, such as a solvent or buffer, a stabilizer, or a preservative. The kit can also include other agents, e.g., a second or third agent, e.g., other therapeutic agents. The components can be provided in any form, e.g., liquid, dried or lyophilized form. The components can be substantially pure (although they can be combined together or delivered separate from one another) and/or sterile. When the components are provided in a liquid solution, the liquid solution can be an aqueous solution, such as a sterile aqueous solution. When the components are provided as a dried form, reconstitution generally is by the addition of a suitable solvent. The solvent, e.g., sterile water or buffer, can optionally be provided in the kit.

The kit can include one or more containers for an NMD agent or other agents. In some cases, the kit contains separate containers, dividers or compartments for an NMD agent and informational material. For example, an NMD agent can be contained in a bottle, vial, or syringe, and the informational material can be contained in a plastic sleeve or packet. In other situations, the separate elements of the kit are contained within a single, undivided container. For example, an NMD agent can be contained in a bottle, vial or syringe that has attached thereto the informational material in the form of a label. In some cases, the kit can include a plurality (e.g., a pack) of individual containers, each containing one or more unit dosage forms (e.g., a dosage form described herein) of an NMD agent. The containers can include a unit dosage, e.g., a unit that includes an NMD agent. For example, the kit can include a plurality of syringes, ampules, foil packets, blister packs, or medical devices, e.g., each containing a unit dose. The containers of the kits can be air tight, waterproof (e.g., impermeable to changes in moisture or evaporation), and/or light-tight.

The kit can optionally include a device suitable for administration of an NMD agent, e.g., a syringe or other suitable delivery device. The device can be provided preloaded with an NMD agent, e.g., in a unit dose, or can be empty, but suitable for loading.

Treatment of ALS

The present invention encompasses the surprising finding that NMD agents are useful, among other things, in the treatment or prevention (i.e., delay of onset) of ALS. UPF1 was initially identified as one of many genes able to rescue toxicity mediated by FUS/TLS in a yeast model (Ju et al., PLoS Biol. 9:e1001052 (2011)). However, the present finding that expressing UPF1 in neuronal cells expressing FUS/TLS or TDP-43 reduces cellular toxicity is surprising, especially given the finding that expression of UPF1 had no effect on the cytoplasmic levels of FUS/TLS or TDP-43 in the neuronal cells. Accordingly, in some embodiments, an NMD agent is provided to the central nervous system of a subject, e.g., a subject suffering from or susceptible to ALS. In some embodiments, an NMD agent is provided to one or more of target cells or tissues of brain, spinal cord, and/or peripheral organs. In some embodiments, target cells or tissues include those cells or tissues that display a disease-associated pathology, symptom, or feature. In some embodiments, target cells or tissues include those cells or tissues in which TDP-43 or FUS/TLS is expressed at an elevated level, e.g., cells in which TDP-43 or FUS/TLS is expressed at an elevated level in the cytoplasm of the cells. As used herein, a target tissue may be a brain target tissue, a spinal cord target tissue and/or a peripheral target tissue.

Compositions described herein can be provided directly into the CNS of a subject suffering from or at risk of developing ALS, thereby achieving a therapeutic concentration within the affected cells and tissues of the CNS (e.g., the brain). For example, one or more NMD agents can be provided to target cells or tissues of the brain, spinal cord and/or peripheral organs to treat ALS. As used herein, the term "treat" or "treatment" refers to amelioration of one or more symptoms associated with the disease, prevention or delay of the onset of one or more symptoms of the disease, and/or lessening of the severity or frequency of one or more symptoms of the disease.

In some embodiments, treatment refers to partially or complete alleviation, amelioration, relief, inhibition, delaying onset, reducing severity and/or incidence of neurological impairment in a patient suffering from or susceptible to ALS. As used herein, the term "neurological impairment" includes various symptoms associated with impairment of the central nervous system (e.g., the brain and spinal cord). Symptoms of neurological impairment may include, for example, developmental delay, progressive cognitive impairment, hearing loss, impaired speech development, deficits in motor skills, hyperactivity, aggressiveness and/or sleep disturbances, among others.

In some embodiments, treatment refers to decreased toxicity of various cells or tissues. In some embodiments, treatment refers to decreased neuronal toxicity due to FUS or TDP-43 in brain target tissues, spinal cord neurons, and/or peripheral target tissues. In certain embodiments, toxicity is decreased by about 5%, 10%, 15%, 20%, 25%, 30%, 35%, 40%, 45%, 50%, 55%, 60%, 65%, 70%, 75%, 80%, 85%, 90%, 95%, 100% or more as compared to a control. In some embodiments, toxicity is decreased by at least 1-fold, 2-fold, 3-fold, 4-fold, 5-fold, 6-fold, 7-fold, 8-fold, 9-fold or 10-fold as compared to a control. In some embodiments, toxicity is measured by tests known to those of ordinary skill in the art including, but not limited to, neuroimaging methods (e.g., CT scans, MRI, functional MRI, etc.).

In certain embodiments, treatment according to the present disclosure results in a reduction (e.g., about a 5%, 10%, 15%, 20%, 25%, 30%, 40%, 50%, 55%, 60%, 65%, 70%, 75%, 80%, 90%, 95%, 97.5%, 99% or more reduction) or a complete elimination of the presence, or alternatively the accumulation, of one or more pathological, clinical, or biological markers that are associated with ALS. For example, in some embodiments, upon administration to a subject, a pharmaceutical composition described herein demonstrates or achieves a reduction in muscle loss, muscle twitching, muscle weakness, spasticity, abnormal tendon reflexes, Babinski sign, breathing problems, facial weakness, slurred speech, loss of perception, loss of reasoning, loss of judgment, and/or loss of imagination.

In some embodiments, treatment refers to increased survival (e.g., survival time). For example, treatment can result in an increased life expectancy of a patient. In some embodiments, treatment results in an increased life expectancy of a patient by more than about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 105%, about 110%, about 115%, about 120%, about 125%, about 130%, about 135%, about 140%, about 145%, about 150%, about 155%, about 160%, about 165%, about 170%, about 175%, about 180%, about 185%, about 190%, about 195%, about 200% or more, as compared to the average life expectancy of one or more control individuals with ALS without treatment. In some embodiments, treatment results in an increased life expectancy of a patient by more than about 6 months, about 7 months, about 8 months, about 9 months, about 10 months, about 11 months, about 12 months, about 2 years, about 3 years, about 4 years, about 5 years, about 6 years, about 7 years, about 8 years, about 9 years, about 10 years or more, as compared to the average life expectancy of one or more control individuals with ALS without treatment. In some embodiments, treatment results in long term survival of a patient. As used herein, the term "long term survival" refers to a survival time or life expectancy longer than about 40 years, 45 years, 50 years, 55 years, 60 years, or longer.

The term "improve," "increase" or "reduce," as used herein, indicates values that are relative to a control. In some embodiments, a suitable control is a baseline measurement, such as a measurement in the same individual prior to initiation of the treatment described herein, or a measurement in a control individual (or multiple control individuals) in the absence of the treatment described herein. A "control individual" is an individual afflicted with ALS, who is about the same age and/or gender as the individual being treated (to ensure that the stages of the disease in the treated individual and the control individual(s) are comparable).

The individual (also referred to as "patient" or "subject") being treated is an individual (fetus, infant, child, adolescent, or adult human) having ALS or having the potential to develop ALS. In some instances, a subject to be treated is genetically predisposed to developing ALS. For example, a subject to be treated has a mutation in a SOD1 gene, ALS2 gene, VAPB gene, SETX gene, TDP-43 gene, FUS/TLS gene, and/or OPTN gene.

Combination Therapy

In some embodiments, an NMD agent described herein is administered to a subject in combination with one or more additional therapies to treat ALS or one or more symptoms of ALS. For example, an NMD agent can be administered in combination with riluzole (Rilutek®, Sanofi-Aventis, Bridgewater, N.J.), baclofen, diazepam, trihexyphenidyl or amitriptyline.

In some embodiments, combined administration of an NMD agent and a second agent results in an improvement in ALS or a symptom thereof to an extent that is greater than one produced by either the NMD agent or the second agent alone. The difference between the combined effect and the effect of each agent alone can be a statistically significant difference.

In some embodiments, combined administration of an NMD agent and a second agent allows administration of the second agent at a reduced dose, at a reduced number of doses, and/or at a reduced frequency of dosage compared to a standard dosing regimen approved for the second agent. For example, approved standard regimen for Rilutek® is 50 mg every 12 hours. Accordingly, for administration in combination with an NMD agent, a therapeutically effective amount of Rilutek® can be a dosage of less than about 50 mg and/or a frequency of greater than about every 12 hours.

In some embodiments, an immunosuppressant agent known to the skilled artisan can be administered to a subject in combination with an NMD polypeptide described herein. Exemplary immunosuppressant agents include, without limitation, cyclosporine, FK506, rapamycin, CTLA4-Ig, anti-TNF agents (such as etanercept), daclizumab (e.g., Zenapax™), anti-CD2 agents, anti-CD4 agents, and anti-CD40 agents.

Methods of Identifying Modulators of NMD Polypeptide Expression or Activity

NMD polypeptides described herein (e.g., UPF1, UPF2, UPF3, SMG1, SMG5, SMG6, or SMG7 polypeptides) are useful for identifying agents that can be potentially used to treat ALS. For example, an agent that increases expression or activity of an NMD polypeptide can be identified as an agent that can be used to treat ALS. Numerous methods exist for evaluating whether an agent alters NMD polypeptide expression or NMD polypeptide activity or level. In one embodiment, the ability of a test agent to modulate (e.g., increase or decrease) (e.g., permanently or temporarily) expression from an NMD polynucleotide promoter is evaluated by e.g., routine reporter (e.g., LacZ, luciferase, or GFP) transcription assay. For example, a cell or transgenic animal whose genome comprises a reporter gene operably linked to an NMD polynucleotide promoter, can be contacted with a test agent, and the ability of the test agent to increase or decrease reporter activity is indicative of the ability of the agent to modulate an NMD polypeptide.

In some embodiments, effects of a test agent on NMD polypeptide expression or NMD polypeptide activity or level can be evaluated in a cell, cell lysate, or subject, preferably a non-human experimental mammal, and more preferably a rodent (e.g., a rat, mouse, rabbit), or explant thereof. Methods of assessing NMD polypeptide expression are well know in the art, e.g., Northern analysis, ribonuclease protection assay, reverse transcription-polymerase chain reaction (RT-PCR) or RNA in situ hybridization (see, e.g., Sambrook et al. Molecular Cloning: A Laboratory Manual ($3^{rd}$ ed. 2001)). The level of NMD polypeptide can be monitored by, e.g., Western analysis, immunoassay, or in situ hybridization. In some embodiments, a DNA construct encoding an NMD polypeptide/GFP fusion protein is transfected into cells, and level of GFP fluorescence in the presence or absence of a test agent is determined. An increase in fluorescence in the presence of the test agent is indicative of the ability of the test agent to increase NMD polypeptide level.

In some embodiments, the effect of a test agent on NMD polypeptide expression or NMD polypeptide activity or level is confirmed in a second assay, e.g., is observed as a change, in the presence of the test agent, in the ability of the NMD polypeptide to reduce toxicity of a cell, e.g., a neuronal cell, expressing TDP-43 and/or FUS.

Agents and test agents to be used in the methods described herein include crude or partially or substantially purified extracts of organic sources, e.g., botanical (e.g., herbal) and algal extracts, inorganic elements or compounds, as well as partially or substantially purified or synthetic agents, e.g., small molecules, polypeptides, antibodies, and polynucleotides, and libraries of these.

In one example, combinatorial chemical libraries can be produced or obtained that sample chemical compounds that are structurally or chemically related or unrelated. Preparation and screening of combinatorial chemical libraries is well known to those of skill in the art. Such combinatorial chemical libraries include, but are not limited to, peptide libraries (see, e.g., U.S. Pat. No. 5,010,175; Furka, Int. J. Pept. Prot. Res. 37:487-493 (1991); and Houghton et al., Nature 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication No. WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., Proc. Nat. Acad. Sci. USA 90:6909-6913 (1993)), vinylogous polypeptides (Hagihara et al., J. Amer. Chem. Soc. 114:6568 (1992)), nonpeptidal peptidomimetics with glucose scaffolding (Hirschmann et al., J. Amer. Chem. Soc. 114:9217-9218 (1992)), analogous organic syntheses of small compound libraries (Chen et al., J. Amer. Chem. Soc. 116:2661 (1994)), oligocarbamates (Cho et al., Science 261:1303 (1993)), and/or peptidyl phosphonates (Campbell et al., J. Org. Chem. 59:658 (1994)), nucleic acid libraries, peptide nucleic acid libraries (see, e.g., U.S. Pat. No. 5,539,083), antibody libraries (see, e.g., Vaughn et al., Nature Biotechnology, 14(3):309-314 (1996) and PCT/US96/10287), carbohydrate libraries (see, e.g., Liang et al., Science, 274:1520-1522 (1996) and U.S. Pat. No. 5,593,853), and small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

The invention is further illustrated by the following examples. The examples are provided for illustrative purposes only. They are not to be construed as limiting the scope or content of the invention in any way.

EXAMPLES

Example 1: Expression of UPF1 in Neurons Eliminates Toxicity of FUS or TDP-43

The present Example describes reduction of TDP-43 or FUS-mediated neuronal toxicity by UPF1.

A yeast model of ALS was used to identify a human gene, UPF1, which suppressed toxicity of FUS/TLS in yeast (Ju et al., PLoS Biol. 9:e1001052 (2011)). Further, UPF1 was able to suppress the cytotoxicity of ALS-associated TDP-43 mutations in yeast as well.

To test the efficacy of UPF1 in reducing TDP-43 or FUS-mediated cytotoxicity in neurons, UPF1 was expressed in motor neurons expressing disease-associated FUS or TDP-43. Motor neurons were either isolated from mice or created from fibroblasts taken from human ALS patients using iPS cell techniques (described in Yamanaka et al., Cell 126:663-676 (2006)). FUS or TDP-43 were tagged with EGFP (Enhanced Green Fluorescent Protein) and expressed in motor neurons, which were visualized by fluorescent microscopy using mApple.

The motor neurons died within a few days of FUS or TDP-43 expression due to toxicity of these ALS-related proteins. UPF1 was expressed in the motor neurons and Kaplan-Meyer survival curves were determined. As shown in FIG. 1A, UPF1 expression had no effect on survival of wild type neurons, indicating that UPF1 was not a generic survival factor. However, as shown in FIG. 1B, UPF1 was able to completely eliminate the toxicity of TDP-43 in a dose-dependent manner. UPF1 had a similar effect on cells expressing FUS (data not shown). Moreover, UPF1 expression was unable to rescue the toxicity of ALS-associated mutants of SOD1, demonstrating for the first time that SOD1-dependent fALS is a distinct disease mechanistically.

Example 2: Yeast Screening Assay for Compounds that Rescue FUS Toxicity

A drug screen based on the yeast model described in Example 1 was developed to identify compounds that rescue toxicity that resulted from FUS expression. Because the phenotype was rescue from cell death, the screen demonstrated exceptionally good signal-to noise, with a Z' score of around 0.8.

Briefly, two yeast strains were engineered: "1×FUS", in which a FUS gene was stably integrated at the HIS locus; and "1×Vec", in which an empty vector was integrated at the same locus. The media used were YPRaffinose and 2×YP-Galactose (2× concentrated). Yeast cells were grown by inoculating a single colony of 1×FUS strain or 1×Vec strain into 2 ml YPRaffinose medium and were grown overnight at 30° C. The overnight cultures were then used to inoculate 50 ml YPRaffinose medium at OD600=0.2 and were grown for 24 hrs at 30° C.

The cultures were then diluted in 500 ml 2×YPGalactose medium at OD600=0.2. 384 well plates were pre-filled with 25 μl of each test compound at a concentration of 30 μM. A Multidrop was used to add 25 μl of the suspension of 1×FUS to each well on columns 1-23 of the plate; 1×Vec was added to each well on column 24 as control. The yeast and compounds were mixed thoroughly. The plates were kept in a humidified incubator at 30° C. The OD600 of each plate was monitored at 24 hr and 48 hrs.

The compound(s) that rescued the growth of 1×FUS were selected and retested. The compounds that passed the retest were further checked in a 10-dose response experiment. The compounds that demonstrated good dose responses were re-ordered, and retested.

EQUIVALENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

```
Sequences
UPF1 nucleotide sequence (GenBank Accession No.
U59323.1, nt 176-3532)
                                                              (SEQ ID NO: 1)
    176                                                                  atgag 181cgtggaggcg tacgggccca gctcgcagac tctcactttc ctggacacgg aggaggccga 241gctgcttggc gccgacacac agggctccga gttcgagttc accgacttta ctcttcctag 301ccagacgcag acgcccccg gcggccccgg cggcccgggc ggtggcggcg cgggaagccc 361gggcggcgcg ggcgccggcg ctgcggcggg acagctcgac gcgcaggttg ggcccgaagg 421catcctgcag aacggggctg tggacgacag tgtagccaag accagccagt tgttggctga 481gttgaacttc gaggaagatg aagaagacac ctattacacg aaggacctcc ccatacacgc 541ctgcagttac tgtggaatac acgatcctgc ctgcgtggtt tactgtaata ccagcaagaa 601gtggttctgc aacggacgtg gaaatacttc tggcagccac attgtaaatc accttgtgag 661ggcaaaatgc aaagaggtga ccctgcacaa ggacgggccc ctgggggaga cagtcctgga 721gtgctacaac tgcggctgtc gcaacgtctt cctcctcggc ttcatcccgg ccaaagctga 781ctcagtggtg gtgctgctgt gcaggcagcc ctgtgccagc cagagcagcc tcaaggacat 841caactgggac agctcgcagt ggcagccgct gatccaggac cgctgcttcc tgtcctggct 901ggtcaagatc ccctccgagc aggagcagct gcgggcacgc cagatcacgg cacagcagat 961caacaagctg gaggagctgt ggaaggaaaa cccttctgcc acgctggagg acctggagaa 1021gccggggggtg gacgaggagc cgcagcatgt cctcctgcgg tacgaggacg cctaccagta 1081ccagaacata ttcgggcccc tggtcaagct ggaggccgac tacgacaaga agctgaagga 1141gtcccagact caagataaca tcactgtcag gtgggacctg ggccttaaca agaagagaat 1201cgcctacttc actttgccca agactgactc tgacatgcgg ctcatgcagg gggatgagat 1261atgcctgcgg tacaaagggg accttgcgcc cctgtggaaa gggatcggcc acgtcatcaa 1321ggtccctgat aattatggcg atgagatcgc cattgagctg cggagcagcg tgggtgcacc 1381tgtggaggtg actcacaact tccaggtgga ttttgtgtgg aagtcgacct cctttgacag
```

-continued

```
1441 gatgcagagc gcattgaaaa cgtttgccgt ggatgagacc tcggtgtctg gctacatcta
1501 ccacaagctg ttgggccacg aggtggagga cgtaatcacc aagtgccagc tgcccaagcg
1561 cttcacggcg cagggcctcc ccgacctcaa ccactcccag gtttatgccg tgaagactgt
1621 gctgcaaaga ccactgagcc tgatccaggg cccgccaggc acggggaaga cggtgacgtc
1681 ggccaccatc gtctaccacc tggcccggca aggcaacggg ccggtgctgg tgtgtgctcc
1741 gagcaacatc gccgtggacc agctaacgga gaagatccac cagacggggc taaaggtcgt
1801 gcgcctctgc gccaagagcc gtgaggccat cgactccccg gtgtcttttc tggccctgca
1861 caaccagatc aggaacatgg acagcatgcc tgagctgcag aagctgcagc agctgaaaga
1921 cgagactggg gagctgtcgt ctgccgacga gaagcggtac cgggccttga agcgcaccgc
1981 agagagagag ctgctgatga acgcagatgt catctgctgc acatgtgtgg gcgccggtga
2041 cccgaggctg gccaagatgc agttccgctc cattttaatc gacgaaagca cccaggccac
2101 cgagccggag tgcatggttc ccgtggtcct cggggccaag cagctgatcc ttgtaggcga
2161 ccactgccag ctgggcccag tggtgatgtg caagaaggcg gccaaggccg gctgtcaca
2221 gtcgctcttc gagcgcctgg tggtgctggg catccggccc atccgcctgc aggtccagta
2281 ccggatgcac cctgcactca gcgccttccc atccaacatc ttctacgagg ctccctcca
2341 gaatggtgtc actgcagcgg atcgtgtgaa aagggatt gacttccagt ggccccaacc
2401 cgataaaccg atgttcttct acgtgaccca gggccaagag gagattgcca gctcgggcac
2461 ctcctacctg aacaggaccg aggctgcgaa cgtggagaag atcaccacga agttgctgaa
2521 ggcaggcgcc aagccggacc agattggcat catcacgccc tacgagggcc agcgctccta
2581 cctggtgcag tacatgcagt tcagcggctc cctgcacacc aagctctacc aggaagtgga
2641 gatcgccagt gtggacgcct ttcagggacg cgagaaggac ttcatcatcc tgtcctgtgt
2701 gcgggccaac gagcaccaag gcattggctt tttaaatgac cccaggcgtc tgaacgtggc
2761 cctgaccaga gcaaggtatg gcgtcatcat tgtgggcaac ccgaaggcac tatcaaagca
2821 gccgctctgg aaccacctgc tgaactacta taaggagcag aaggtgctgg tggaggggcc
2881 gctcaacaac ctgcgtgaga gcctcatgca gttcagcaag ccacggaagc tggtcaacac
2941 tatcaacccg ggagcccgct tcatgaccac agccatgtat gatgcccggg aggccatcat
3001 cccaggctcc gtctatgatc ggagcagcca gggccggcct tccagcatgt acttccagac
3061 ccatgaccag attggcatga tcagtgccgg ccctagccca gtggctgcca tgaacattcc
3121 catcccttc aacctggtca tgccacccat gccaccgcct ggctattttg acaagccaa
3181 cgggcctgct gcagggcgag gcaccccgaa aggcaagact ggtcgtgggg gacgccagaa
3241 gaaccgcttt gggcttcctg gacccagcca gactaacctc cccaacagcc aagccagcca
3301 ggatgtggcg tcacagccct ctctcaggg cgccctgacg cagggctaca tctccatgag
3361 ccagccttcc cagatgagcc agcccggcct ctcccagccg gagctgtccc aggacagtta
3421 ccttggtgac gagtttaaat cacaaatcga cgtggcgctc tcacaggact ccacgtacca
3481 gggagagcgg gcttaccagc atggcggggt gacggggctg tcccagtatt aa
```

UPF1 amino acid sequence (GenBank Accession No. AAC51140.1)
(SEQ ID NO: 2)

```
  1 msveaygpss qtltfldtee aellgadtqg sefeftdftl psqtqtppgg pggpgggag
 61 spggagagaa agqldaqvgp egilqngavd dsvaktsqll aelnfeedee dtyytkdlpi
121 hacsycgihd pacvvycnts kkwfcngrgn tsgshivnhl vrakckevtl hkdgplgetv
181 lecyncgcrn vfllgfipak adsvvvllcr qpcasqsslk dinwdssqwq pliqdrcfls
241 wlvkipseqe qlrarqitaq qinkleelwk enpsatledl ekpgvdeepq hvllryeday
```

```
301 qyqnifgplv kleadydkkl kesqtqdnit vrwdlglnkk riayftlpkt dsdmrlmqgd
361 eiclrykgdl aplwkgighv ikvpdnygde iaielrssvg apvevthnfq vdfvwkstsf
421 drmqsalktf avdetsysgy iyhkllghev edvitkcqlp krftaqglpd lnhsqvyavk
481 tvlqrplsli qgppgtgktv tsativyhla rqgngpvlvc apsniavdql tekihqtglk
541 vvvrlcaksre aidspvsfla lhnqirnmds mpelqklqql kdetgelssa dekryralkr
601 taerellmna dvicctcvga gdprlakmqf rsilidestq atepecmvpv vlgakqlilv
661 gdhcqlgpvv mckkaakagl sqslferlvv lgirpirlqv qyrmhpalsa fpsnifyegs
721 lqngvtaadr vkkgfdfqwp qpdkpmffyv tqgqeeiass gtsylnrtea anvekittkl
781 lkagakpdqi giitpyegqr sylvqymqfs gslhtklyqe veiasvdafq grekdfiils
841 cvranehqgi gflndprrln valtrarygv iivgnpkals kqplwnhlln yykeqkvlve
901 gplnnlresl mqfskprklv ntinpgarfm ttamydarea iipgsvydrs sqgrpssmyf
961 qthdqigmis agpshvaamn ipipfnlvmp pmpppgyfgq angpaagrgt pkgktgrggr
1021 qknrfglpgp sqtnlpnsqa sqdvasqpfs qgaltqgyis msqpsqmsqp glsqpelsqd
1081 sylgdefksq idvalsqdst yqgerayqhg gvtglsqy
```

UPF2 nucleotide sequence (GenBank Accession No. AF318574.1)
(nt 76-3894)

(SEQ ID NO: 3)

```
  76                 atgcc agctgagcgt aaaaagccag caagtatgga agaaaaagac
 121 tctttaccaa acaacaagga aaaagactgc agtgaaaggc ggacagtgag cagcaaggag
 181 aggccaaaag acgatatcaa gctcactgcc aagaaggagg tcagcaaggc ccctgaagac
 241 aagaagaaga gactggaaga tgataagaga aaaaggaag acaaggaacg caagaaaaaa
 301 gacgaagaaa aggtgaaggc agaggaagaa tcaaagaaaa aagaagagga agaaaaaaag
 361 aaacatcaag aggaagagag aaagaagcaa gaagagcagg ccaaacgtca gcaagaagaa
 421 gaagcagctg ctcagatgaa agaaaaagaa gaatccattc agcttcatca ggaagcttgg
 481 gaacgacatc atttaagaaa ggaacttcgt agcaaaaacc aaaatgctcc ggacagccga
 541 ccagaggaaa acttcttcag ccgcctcgac tcaagtttga agaaaaatac tgcttttgtc
 601 aagaaactaa aaactattac agaacaacag agagactcct tgtcccatga ttttaatggc
 661 ctaaatttaa gcaaatacat tgcagaagct gtagcttcca tcgtggaagc aaaactaaaa
 721 atctctgatg tgaactgtgc tgtgcacctc tgctctctct ttcaccagcg ttatgctgac
 781 ttttgccccat cacttcttca ggtctggaaa aaacattttg aagcaaggaa agaggagaaa
 841 acacctaaca tcaccaagtt aagaactgat ttgcgtttta ttgcagaatt gacaatagtt
 901 gggatttttca ctgacaagga aggtctttcc ttaatctatg aacagctaaa aaatattatt
 961 aatgctgatc gggagtccca cactcatgtc tctgtagtga ttagtttctg tcgacattgt
1021 ggagatgata ttgctggact tgtaccaagg aaagtaaaga gtgctgcaga aagtttaat
1081 ttgagttttc ctcctagtga gataattagt ccagagaaac aacagccctt ccagaatctt
1141 ttaaaagagt actttacgtc tttgaccaaa cacctgaaaa gggaccacag ggagctccag
1201 aatactgaga gacaaaacag gcgcattcta cattctaaag gggagctcag tgaagataga
1261 cataaacagt atgaggaatt tgctatgtct taccagaagc tgctggcaaa ttctcaatcc
1321 ttagcagacc ttttggatga aaatatgcca gatcttcctc aagacaaacc cacaccagaa
1381 gaacatgggc ctggaattga tatattcaca cctggtaaac ctggagaata tgacttggaa
1441 ggtggtatat gggaagatga agatgctcgg aattttttatg agaacctcat tgatttgaag
1501 gcttttgtcc cagccatctt gtttaaagac aatgaaaaaa gttgtcagaa taaagagtcc
```

-continued

```
1561 aacaaagatg ataccaaaga ggcaaaagaa tctaaggaga ataaggaggt atcaagtccc
1621 gatgatttgg aacttgagtt ggagaatcta gaaattaatg atgacacctt agaattagag
1681 ggtggagatg aagctgaaga tcttacaaag aaacttcttg atgaacaaga acaagaagat
1741 gaggaagcca gcactggatc tcatctcaag ctcatagtag atgctttcct acagcagtta
1801 cccaactgtg tcaaccgaga tctgatagac aaggcagcaa tggattttg catgaacatg
1861 aacacaaaag caaacaggaa gaagttggta cgggcactct tcatagttcc tagacaaagg
1921 ttggatttgc taccatttta tgcaagattg gttgctacat tgcatccctg catgtctgat
1981 gtagcagagg atctttgttc catgctgagg ggggatttca gatttcatgt acggaaaaag
2041 gaccagatca atattgaaac aaagaataaa actgttcgtt ttataggaga actaactaag
2101 tttaagatgt tcaccaaaaa tgacacactg cattgtttaa agatgcttct gtcagacttc
2161 tctcatcacc atattgaaat ggcatgcacc ctgctggaga catgtggacg gtttctttc
2221 agatctccag aatctcacct gaggaccagt gtacttttgg agcaaatgat gagaaagaag
2281 caagcaatgc atcttgatgc gagatacgtc acaatggtag agaatgcata ttactactgc
2341 aaccccacctc cagctgaaaa aaccgtgaaa aagaaacgtc ctcctctcca ggaatatgtc
2401 cggaaacttt tgtacaaaga tctctctaag gttaccaccg agaaggtttt gagacagatg
2461 cgaaagctgc cctggcagga ccaagaagtg aaagactatg ttatttgttg tatgataaac
2521 atctggaatg tgaaatataa tagtattcat tgtgtagcca acctcttagc aggactagtg
2581 ctctaccaag aggatgttgg gatccacgtt gtggatggag tgttagaaga tattcgatta
2641 ggaatggagg ttaatcaacc taaatttaat cagaggcgca tcagcagtgc caagttctta
2701 ggagaacttt acaattaccg aatggtggaa tcagctgtta ttttcagaac tctgtattct
2761 tttacctcat ttggtgttaa tcctgatggc tctccaagtt ccctggaccc acctgagcat
2821 cttttcagaa ttagactcgt atgcactatt ctggacacat gtggccagta cttttgacaga
2881 ggttccagta aacgaaaact tgattgtttc cttgtatatt ttcagcgtta tgtttggtgg
2941 aagaaaagtt tggaggtttg gacaaaagac catccatttc ctattgatat agattacatg
3001 atcagtgata cactagaact gctaagacca aagatcaaac tctgtaattc tctggaagaa
3061 tccatcaggc aggtacaaga cttggaacga gaattcttaa taaaactagg cctagtaaat
3121 gacaaagact caaagattc tatgacagaa ggagaaaatc ttgaagagga tgaagaagaa
3181 gaagaaggtg gggctgaaac agaagaacaa tctggaaatg aaagtgaagt aaatgagcca
3241 gaagaagagg agggttctga taatgatgat gatgagggag aagaagagga ggaagagaat
3301 acagattacc ttacagattc caataaggaa aatgaaaccg atgaagagaa tactgaggta
3361 atgattaaag gcggtggact taagcatgta ccttgtgtag aagatgagga cttcattcaa
3421 gctctggata aaatgatgct agaaaatcta cagcaacgaa gtggtgaatc tgttaaagtg
3481 caccaactag atgtggccat tcctttgcat ctcaaaagcc agctgaggaa agggccccca
3541 ctgggaggtg gggaaggaga ggctgagtct gcagacacaa tgccgtttgt catgttaaca
3601 agaaaaaggca ataaacagca gtttaagatc cttaatgtac ccatgtcctc tcaacttgct
3661 gcaaatcact ggaaccagca acaggcagaa caagaagaga ggatgagaat gaagaagctc
3721 acactagata tcaatgaacg gcaagaacaa gaagattatc aagaaatgtt gcagtctctt
3781 gcacagcgcc cagctccagc aaacaccaat cgtgagaggg ggcctcgcta ccaacatccg
3841 aagggagcac ctaatgcaga tctaatcttt aagactggtg ggaggagacg ttga
```

UPF2 amino acid sequence (GenBank Accession No. AAG60689.1)

(SEQ ID NO: 4)

```
   1 mpaerkkpas meekdslpnn kekdcserrt vsskerpkdd ikltakkevs kapedkkkrl
  61 eddkrkkedk erkkkdeekv kaeeeskkke eeekkkhqee erkkqeeqak rqqeeeaaaq
 121 mkekeesiql hqeawerhhl rkelrsknqn apdsrpeenf fsrldsslkk ntafvkklkt
 181 iteqqrdsls hdfnglnlsk yiaeavasiv eaklkisdvn cavhlcslfh qryadfapsl
 241 lqvwkkhfea rkeektpnit klrtdlrfia eltivgiftd keglsliyeq lkniinadre
 301 shthvsvvis fcrhcgddia glvprkvksa aekfnlsfpp seiispekqq pfqnllkeyf
 361 tsltkhhlkrd hrelqnterq nrrilhskge lsedrhkqye efamsyqkll ansqsladll
 421 denmpdlpqd kptpeehgpg idiftpgkpg eydleggiwe dedarnfyen lidlkafvpa
 481 ilfkdneksc qnkesnkddt keakeskenk evsspddlel elenleindd tleleggdea
 541 edltkkllde qeqedeeast gshlklivda flqqlpncvn rdlidkaamd fcmnmntkan
 601 rkklvralfi vprqrldllp fyarlvatlh pcmsdvaedl csmlrgdfrf hvrkkdqini
 661 etknktvrfi geltkfkmft kndtlhclkm llsdfshhhi emactlletc grflfrspes
 721 hlrtsvlleq mmrkkqamhl daryvtmven ayyycnpppa ektvkkkrpp lqeyvrklly
 781 kdlskvttek vlrqmrklpw qdqevkdyvi ccminiwnvk ynsihcvanl laglvlyqed
 841 vgihvvdgvl edirlgmevn qpkfnqrris sakflgelyn yrmvesavif rtlysftsfg
 901 vnpdgspssl dppehlfrir lvctildtcg qyfdrgsskr kldcflvyfq ryvwwkksle
 961 vwtkdhpfpi didymisdtl ellrpkiklc nsleesirqv qdlereflik lglvndkdsk
1021 dsmtegenle edeeeeegga eteeqsgnes evnepeeeeg sdndddegee eeeentdylt
1081 dsnkenetde entevmikgg glkhvpcved edfiqaldkm mlenlqqrsg esvkvhqldv
1141 aiplhlksql rkgpplggge geaesadtmp fvmltrkgnk qqfkilnvpm ssqlaanhwn
1201 qqqaeqeerm rmkkltldin erqeqedyqe mlqslaqrpa pantnrerrp ryqhpkgapn
1261 adlifktggr rr
```

UPF3 nucleotide sequence (GenBank Accession No. AF318575_1)
(nt 22-1380)

(SEQ ID NO: 5)

```
  22                    atgctgtcg gccctagaag tgcagttcca ccgcgactcg
  61 cagcagcagg aggctgagac gccgccaact tcgtcctccg gttgcggggg cggtgcgggc
 121 aaaccctcgcg aggagaagag gacggccctg agcaaggtgg tcatccgccg cctgcctccg
 181 ggcctcacca aggagcagct ggaggagcag ctgcgcccgc tgccagcaca cgactacttc
 241 gagttcttcg ccgccgacct gagtctttat cctcatctct actcaagagc atacattaat
 301 ttttaggaatc ctgatgacat ccttcttttt agagatcgtt ttgatggata tatcttcctt
 361 gacagcaaag gcctagaata tcctgcagtg gtagagtttg ctccattcca gaagatagcc
 421 aaaaagaagc tgagaaaaaa agatgccaag actggaagca tcgaagatga tccagaatat
 481 aagaagtttt tagaaaccta ctgtgtggag gaagagaaga ccagtgccaa ccctgagact
 541 ctgctggggg agatggaggc gaagacaaga gagctcattg ctagaagaac cacacctctt
 601 ttggaatata ttaaaaatag aaaattagaa aagcagagaa ttcgagaaga gaagcgagaa
 661 gaacggagga ggagagagtt agaaaagaaa cgtttgcggg aagaggaaaa aagaagaaga
 721 agagaagaag aaagatgcaa aaaaaagag acagataaac agaagaaaat tgcagagaaa
 781 gaagtaagga ttaagcttct taagaaacca gaaaagggag aggaaccaac cacagagaaa
 841 ccaaaagaaa gaggagagga gattgatact ggaggtggca agcaggaatc ctgtgccccc
 901 ggtgcagtcg taaaagccag gcccatggaa ggctcgctgg aggagcccca ggagacgtca
```

```
 961 cacagcggca gtgataaaga gcacagggat gtggagagat ctcaagaaca agaatctgaa
1021 gcacaaagat accatgtgga tgacggcagg aggcacagag ctcaccacga gcctgaacgg
1081 ctttccagaa ggagtgagga tgagcagaga tgggggaaag gacctggcca agacagaggg
1141 aagaagggga gccaggacag cggggctccg gggaggcca tggagagact gggaagagcg
1201 caaaggtgtg acgacagtcc agcacccaga aaagagcgac tggcaaacaa ggaccggcca
1261 gccttgcagc tgtatgatcc aggagctcgc ttccgagcgc gagagtgtgg cggaaacagg
1321 aggatctgca aggcagaagg ttcggggact ggtcctgaga gagggaaga ggcagagtga
```

UPF3 amino acid sequence (GenBank Accession No. AAG60690.1)

(SEQ ID NO: 6)

```
  1 mlsalevqfh rdsqqqeaet pptsssgcgg gagkpreekr talskvvirr lppgltkeql
 61 eeqlrplpah dyfeffaadl slyphlysra yinfrnpddi llfrdrfdgy ifldskgley
121 pavvefapfq kiakkklrkk daktgsiedd peykkflety cveeektsan petllgemea
181 ktreliarrt tplleyiknr klekqriree kreerrrrel ekkrlreeek rrrreeerck
241 kketdkqkki aekevrikll kkpekgeept tekpkergee idtgggkqes capgavvkar
301 pmegsleepq etshsgsdke hrdversqeq eseaqryhvd dgrrhrahhe perlsrrsed
361 eqrwgkgpgq drgkkgsqds gapgeamerl graqrcddsp aprkerlank drpalqlydp
421 garfrarecg gnrrickaeg sgtgpekree ae
```

SMG1 nucleotide sequence (GenBank Accession No. NM_015092.4, nt 364-11349)

(SEQ ID NO: 7)

```
 364    atgagcc gcagagcccc gggtctcgg ctgagcagcg gcggcggcgg cggcggcacc
 421 aagtatccgc ggagctggaa tgactggcaa cccagaactg atagtgcatc agccgaccca
 481 gataatttaa atattcttc atccagagat agaggtggtt cttcctctta tggactgcaa
 541 ccttcaaatt cagctgtggt gtctcggcaa aggcacgatg ataccagagt ccacgctgac
 601 atacagaatg acgaaaaggg tggctacagt gtcaatggag gatctgggga aaatacttat
 661 ggtcggaagt cgttggggca agagctgagg gttaacaatg tgaccagccc tgagttcacc
 721 agtgttcagc atggcagtcg tgctttagcc accaaagaca tgaggaaatc acaggagaga
 781 tcgatgtctt attctgatga gtctcgactg tcgaatcttc ttcggaggat cacccgggaa
 841 gacgacagag accgaagatt ggctactgta aagcagttga agaatttat tcagcaacca
 901 gaaaataagc tggtactagt taaacaattg gataatatct tggctgctgt acatgacgtg
 961 cttaatgaaa gtagcaaatt gcttcaggag ttgagacagg agggagcttg ctgtcttggc
1021 ctttctttgtg cttctctgag ctatgaggct gagaagatct tcaagtggat ttttagcaaa
1081 ttttagctcat ctgcaaaaga tgaagttaaa ctcctctact tatgtgccac ctacaaagca
1141 ctagagactg taggagaaaa gaaagccttt tcatctgtaa tgcagcttgt aatgaccagc
1201 ctgcagtcta ttcttgaaaa tgtggataca ccagaattgc tttgtaaatg tgttaagtgc
1261 attcttttgg tggctcgatg ttaccctcat attttcagca ctaattttag ggatacagtt
1321 gatatattag ttggatggca tatagatcat actcagaaac cttcgctcac gcagcaggta
1381 tctgggtggt tgcagagttt ggagccattt tgggtagctg atcttgcatt ttctactact
1441 cttcttggtc agtttctgga agacatggaa gcatatgctg aggacctcag ccatgtggcc
1501 tctgggggaat cagtggatga agatgtccct cctccatcag tgtcattacc aaagctggct
1561 gcacttctcc gggtatttag tactgtggtg aggagcattg gggaacgctt cagcccaatt
1621 cggggtcctc caattactga ggcatatgta acagatgttc tgtacagagt aatgagatgt
1681 gtgacggctg caaaccaggt gtttttttct gaggctgtgt tgacagctgc taatgagtgt
```

-continued

```
1741 gttggtgttt tgctcggcag cttggatcct agcatgacta tacattgtga catggtcatt
1801 acatatggat tagaccaact ggagaattgc cagacttgtg gtaccgatta tatcatctca
1861 gtcttgaatt tactcacgct gattgttgaa cagataaata cgaaactgcc atcatcattt
1921 gtagaaaaac tgtttatacc atcatctaaa ctactattct tgcgttatca taaagaaaaa
1981 gaggttgttg ctgtagccca tgctgtttat caagcagtgc tcagcttgaa gaatattcct
2041 gttttggaga ctgcctataa gttaatattg ggagaaatga cttgtgccct aaacaacctc
2101 ctacacagtc tacaacttcc tgaggcctgt tctgaaataa acatgaggc ttttaagaat
2161 catgtgttca atgtagacaa tgcaaaattt gtagttatat ttgacctcag tgccctgact
2221 acaattggaa atgccaaaaa ctcactaata gggatgtggg cgctatctcc aactgtcttt
2281 gcacttctga gtaagaatct gatgattgtg cacagtgacc tggctgttca cttccctgcc
2341 attcagtatg ctgtgctcta cacattgtat tctcattgta ccaggcatga tcactttatc
2401 tctagtagcc tcagttcttc ctctccttct ttgtttgatg gagctgtgat tagcactgta
2461 actacggcta caaagaaaca tttctcaatt atattaaatc ttctgggaat attacttaag
2521 aaagataacc ttaaccagga cacgaggaaa ctgttaatga cttgggcttt ggaagcagct
2581 gttttaatga agaagtctga aacatacgca cctttattct ctcttccgtc tttccataaa
2641 ttttgcaaag cctttttagc caacactctc gttgaagatg tgaatatctg tctgcaggca
2701 tgcagcagtc tacatgctct gtcctcttcc ttgccagatg atcttttaca gagatgtgtc
2761 gatgtttgcc gtgttcaact agtgcacagt ggaactcgta ttcgacaagc atttggaaaa
2821 ctgttgaaat caattccttt agatgttgtc ctaagcaata acaatcacac agaaattcaa
2881 gaaatttctt tagcattaag aagtcacatg agtaaagcac caagtaatac attccacccc
2941 caagatttct ctgatgttat tagttttatt ttgtatggga actctcatag aacagggaag
3001 gacaattggt tggaaagact gttctatagc tgccagagac tggataagcg tgaccagtca
3061 acaattccac gcaatctcct gaagacagat gctgtccttt ggcagtgggc catatgggaa
3121 gctgcacaat tcactgttct ttctaagctg agaaccccac tgggcagagc tcaagacacc
3181 ttccagacaa ttgaaggtat cattcgaagt ctcgcagctc acacattaaa ccctgatcag
3241 gatgttagtc agtggacaac tgcagacaat gatgaaggcc atggtaacaa ccaacttaga
3301 cttgttcttc ttctgcagta tctggaaaat ctggagaaat taatgtataa tgcatacgag
3361 ggatgtgcta atgcattaac ttcacctccc aaggtcatta gaactttttt ctataccaat
3421 cgccaaactt gtcaggactg gctaacgcgg attcgactct ccatcatgag ggtaggattg
3481 ttggcaggcc agcctgcagt gacagtgaga catggctttg acttgcttac agagatgaaa
3541 acaaccagcc tatctcaggg gaatgaattg gaagtaacca ttatgatggt ggtagaagca
3601 ttatgtgaac ttcattgtcc tgaagctata cagggaattg ctgtctggtc atcatctatt
3661 gttggaaaaa atcttctgtg gattaactca gtggctcaac aggctgaagg gaggtttgaa
3721 aaggcctctg tggagtacca ggaacacctg tgtgccatga caggtgttga ttgctgcatc
3781 tccagctttg acaaatcggt gctcaccta gccaatgctg ggcgtaacag tgccagcccg
3841 aaacattctc tgaatggtga atccagaaaa actgtgctgt ccaaaccgac tgactcttcc
3901 cctgaggtta taaattattt aggaaataaa gcatgtgagt gctacatctc aattgccgat
3961 tgggctgctg tgcaggaatg gcagaacgct atccatgact gaaaaagag taccagtagc
4021 acttccctca acctgaaagc tgacttcaac tatataaaat cattaagcag ctttgagtct
4081 ggaaaatttg ttgaatgtac cgagcagtta gaattgttac caggagaaaa tatcaatcta
```

-continued

```
4141 cttgctggag gatcaaaaga aaaaatagac atgaaaaaac tgcttcctaa catgttaagt
4201 ccggatccga gggaacttca gaaatccatt gaagttcaat tgttaagaag ttctgtttgt
4261 ttggcaactg ctttaaaccc gatagaacaa gatcagaagt ggcagtctat aactgaaaat
4321 gtggtaaagt acttgaagca aacatcccgc atcgctattg gacctctgag actttctact
4381 ttaacagttt cacagtcttt gccagttcta agtaccttgc agctgtattg ctcatctgct
4441 ttggagaaca cagtttctaa cagactttca acagaggact gtcttattcc actcttcagt
4501 gaagctttac gttcatgtaa acagcatgac gtgaggccat ggatgcaggc attaaggtat
4561 actatgtacc agaatcagtt gttggagaaa attaaagaac aaacagtccc aattagaagc
4621 catctcatgg aattaggtct aacagcagca aaatttgcta gaaaacgagg gaatgtgtcc
4681 cttgcaacaa gactgctggc acagtgcagt gaagttcagc tgggaaagac caccactgca
4741 caggatttag tccaacattt taaaaaacta tcaacccaag gtcaagtgga tgaaaaatgg
4801 gggcccgaac ttgatattga aaaaaccaaa ttgctttata cagcaggcca gtcaacacat
4861 gcaatggaaa tgttgagttc ttgtgccata tctttctgca agtctgtgaa agctgaatat
4921 gcagttgcta aatcaattct gacactggct aaatggatcc aggcagaatg gaaagagatt
4981 tcaggacagc tgaaacaggt ttacagagct cagcaccaac agaacttcac aggtctttct
5041 actttgtcta aaaacatact cactctaata gaactgccat ctgttaatac gatggaagaa
5101 gagtatcctc ggatcgagag tgaatctaca gtgcatattg gagttggaga acctgacttc
5161 attttgggac agttgtatca cctgtcttca gtacaggcac ctgaagtagc caaatcttgg
5221 gcagcgttgg ccagctgggc ttataggtgg ggcagaaagg tggttgacaa tgccagtcag
5281 ggagaaggtg ttcgtctgct gcctagagaa aaatctgaag ttcagaatct acttccagac
5341 actataactg aggaagagaa agagagaata tatggtattc ttggacaggc tgtgtgtcgg
5401 ccggcgggga ttcaggatga agatataaca cttcagataa ctgagagtga agacaacgaa
5461 gaagatgaca tggttgatgt tatctggcgt cagttgatat caagctgccc atggcttca
5521 gaacttgatg aaagtgcaac tgaaggagtt attaaagtgt ggaggaaagt tgtagataga
5581 atattcagcc tgtacaaact ctcttgcagt gcatacttta cttccttaa actcaacgct
5641 ggtcaaattc ctttagatga ggatgaccct aggctgcatt taagtcacag agtggaacag
5701 agcactgatg acatgattgt gatggccaca ttgcgcctgc tgcggttgct cgtgaagcat
5761 gctggtgagc ttcggcagta tctggagcac ggcttggaga caacacccac tgcaccatgg
5821 agaggaatta ttccgcaact tttctcacgc ttaaaccacc tgaagtgta tgtgcgccaa
5881 agtatttgta accttctctg ccgtgtggct caagattccc cacatctcat attgtatcct
5941 gcaatagtgg gtaccatatc gcttagtagt gaatcccagg cttcaggaaa taaattttcc
6001 actgcaattc caactttact tggcaatatt caaggagaag aattgctggt ttctgaatgt
6061 gagggaggaa gtcctcctgc atctcaggat agcaataagg atgaacctaa agtggatta
6121 aatgaagacc aagccatgat gcaggattgt tacagcaaaa ttgtagataa gctgtcctct
6181 gcaaaccccca ccatggtatt acaggttcag atgctcgtgg ctgaactgcg cagggtcact
6241 gtgctctggg atgagctctg gctggagtt ttgctgcaac aacacatgta tgtcctgaga
6301 cgaattcagc agcttgaaga tgaggtgaag agagtccaga caacaacac cttacgcaaa
6361 gaagagaaaa ttgcaatcat gagggagaag cacacagctt tgatgaagcc catcgtattt
6421 gcttttggagc atgtgaggag tatcacagcg gctcctgcag aaacacctca tgaaaaatgg
6481 tttcaggata actatggtga tgccattgaa atgccctag aaaaactgaa gactccattg
6541 aaccctgcaa agcctgggag cagctggatt ccattaaag agataatgct aagtttgcaa
```

-continued

```
6601 cagagagcac agaaacgtgc aagttacatc ttgcgtcttg aagaaatcag tccatggttg
6661 gctgccatga ctaacactga aattgctctt cctggggaag tctcagccag agacactgtc
6721 acaatccata gtgtgggcgg aaccatcaca atcttaccga ctaaaaccaa gccaaagaaa
6781 cttctctttc ttggatcaga tgggaagagc tatccttatc ttttcaaagg actggaggat
6841 ttacatctgg atgagagaat aatgcagttc ctatctattg tgaataccat gtttgctaca
6901 attaatcgcc aagaaacacc ccggttccat gctcgacact attctgtaac accactagga
6961 acaagatcag gactaatcca gtgggtagat ggagccacac ccttatttgg tctttacaaa
7021 cgatggcaac aacgggaagc tgccttacaa gcacaaaagg cccaagattc ctaccaaact
7081 cctcagaatc ctggaattgt accccgtcct agtgaacttt attacagtaa aattggccct
7141 gctttgaaaa cagttgggct tagcctggat gtgtcccgtc gggattggcc tcttcatgta
7201 atgaaggcag tattggaaga gttaatggag gccacacccc cgaatctcct tgccaaagag
7261 ctctggtcat cttgcacaac acctgatgaa tggtggagag ttacgcagtc ttatgcaaga
7321 tctactgcag tcatgtctat ggttggatac ataattggcc ttggagacag acatctggat
7381 aatgttctta tagatatgac gactggagaa gttgttcaca tagattacaa tgtttgcttt
7441 gaaaaaggta aaagccttag agttcctgag aaagtacctt ttcgaatgac acaaaacatt
7501 gaaacagcac tgggtgtaac tggagtagaa ggtgtattta ggctttcatg tgagcaggtt
7561 ttacacatta tgcggcgtgg cagagagacc ctgctgacgc tgctggaggc ctttgtgtac
7621 gaccctctgg tggactggac agcaggaggc gaggctgggt ttgctggtgc tgtctatggt
7681 ggaggtggcc agcaggccga gagcaagcag agcaagagag agatggagcg agagatcacc
7741 cgcagcctgt tttcttctag agtagctgag attaaggtga actggtttaa gaatagagat
7801 gagatgctgg ttgtgcttcc caagttggac ggtagcttag atgaatacct aagcttgcaa
7861 gagcaactga cagatgtgga aaaactgcag ggcaaactac tggaggaaat agagtttcta
7921 gaaggagctg aaggggtgga tcatccttct catactctgc aacacaggta ttctgagcac
7981 acccaactac agactcagca aagagctgtt caggaagcaa tccaggtgaa gctgaatgaa
8041 tttgaacaat ggataacaca ttatcaggct gcattcaata atttagaagc aacacagctt
8101 gcaagcttgc ttcaagagat aagcacacaa atggaccttg gtcctccaag ttacgtgcca
8161 gcaacagcct ttctgcagaa tgctggtcag gcccacttga ttagccagtg cgagcagctg
8221 gagggggagg ttggtgctct cctgcagcag aggcgctccg tgctccgtgg ctgtctggag
8281 caactgcatc actatgcaac cgtggccctg cagtatccga aggccatatt tcagaaacat
8341 cgaattgaac agtggaagac ctggatggaa gagctcatct gtaacaccac agtagagcgt
8401 tgtcaagagc tctataggaa atatgaaatg caatatgctc cccagccacc cccaacagtg
8461 tgtcagttca tcactgccac tgaaatgacc ctgcagcgat acgcagcaga catcaacagc
8521 agacttatta gacaagtgga acgcttgaaa caggaagctg tcactgtgcc agtttgtgaa
8581 gatcagttga agaaattga acgttgcatt aaagttttcc ttcatgagaa tggagaagaa
8641 ggatctttga gtctagcaag tgttattatt tctgcccttt gtaccttac aaggcgtaac
8701 ctgatgatgg aaggtgcagc gtcaagtgct ggagaacagc tggttgatct gacttctcgg
8761 gatggagcct ggttcttgga ggaactctgc agtatgagcg aaacgtcac ctgcttggtt
8821 cagttactga agcagtgcca cctggtgcca caggacttag atatcccgaa ccccatggaa
8881 gcgtctgaga cagttcactt agccaatgga gtgtatacct cacttcagga attgaattcg
8941 aatttccggc aaatcatatt tccagaagca cttcgatgtt aatgaaagg ggaatacacg
```

```
9001  ttagaaagta tgctgcatga actggacggt cttattgagc agaccaccga tggcgttccc
9061  ctgcagactc tagtggaatc tcttcaggcc tacttaagaa acgcagctat gggactggaa
9121  gaagaaacac atgctcatta catcgatgtt gccagactac tacatgctca gtacggtgaa
9181  ttaatccaac cgagaaatgg ttcagttgat gaaacaccca aaatgtcagc tggccagatg
9241  cttttggtag cattcgatgg catgtttgct caagttgaaa ctgctttcag cttattagtt
9301  gaaaagttga caagatgga aattcccata gcttggcgaa agattgacat cataagggaa
9361  gccaggagta ctcaagttaa ttttttgat gatgataatc accggcaggt gctagaagag
9421  attttctttc taaaaagact acagactatt aaggagttct tcaggctctg tggtaccttt
9481  tctaaaacat tgtcaggatc aagttcactt gaagatcaga atactgtgaa tgggcctgta
9541  cagattgtca atgtgaaaac cctttttaga aactcttgtt tcagtgaaga ccaaatggcc
9601  aaacctatca aggcattcac agctgacttt gtgaggcagc tcttgatagg gctacccaac
9661  caagccctcg gactcacact gtgcagtttt atcagtgctc tgggtgtaga catcattgct
9721  caagtagagg caaaggactt tggtgccgaa agcaaagttt ctgttgatga tctctgtaag
9781  aaagcggtgg aacataacat ccagataggg aagttctctc agctggttat gaacagggca
9841  actgtgttag caagttctta cgacactgcc tggaagaagc atgacttggt gcgaaggcta
9901  gaaaccagta tttcttcttg taagacaagc ctgcagcggg ttcagctgca tattgccatg
9961  tttcagtggc aacatgaaga tctacttatc aatagaccac aagccatgtc agtcacacct
10021 cccccacggt ctgctatcct aaccagcatg aaaaagaagc tgcataccct gagccagatt
10081 gaaacttcta ttgcaacagt tcaggagaag ctagctgcac ttgaatcaag tattgaacag
10141 cgactcaagt gggcaggtgg tgccaaccct gcattggccc ctgtactaca agattttgaa
10201 gcaacgatag ctgaaagaag aaatcttgtc cttaaagaga gccaaagagc aagtcaggtc
10261 acatttctct gcagcaatat cattcatttt gaaagtttac gaacaagaac tgcagaagcc
10321 ttaaacctgg atgcggcgtt atttgaacta atcaagcgat gtcagcagat gtgttcgttt
10381 gcatcacagt ttaacagttc agtgtctgag ttagagcttc gtttattaca gagagtggac
10441 actggtcttg aacatcctat tggcagctct gaatggcttt tgtcagcaca caaacagttg
10501 acccaggata tgtctactca gagggcaatt cagacagaga aagagcagca gatagaaacg
10561 gtctgtgaaa caattcagaa tctggttgat aatataaaga ctgtgctcac tggtcataac
10621 cgacagcttg gagatgtcaa acatctcttg aaagctatgg ctaaggatga agaagctgct
10681 ctggcagatg gtgaagatgt tccctatgag aacagtgtta ggcagttttt gggtgaatat
10741 aaatcatggc aagacaacat tcaaacagtt ctatttacat tagtccaggc tatgggtcag
10801 gttcgaagtc aagaacacgt tgaaatgctc caggaaatca ctcccacctt gaaagaactg
10861 aaaacacaaa gtcagagtat ctataataat ttagtgagtt ttgcatcacc cttagtcacc
10921 gatgcaacaa atgaatgttc gagtccaacg tcatctgcta cttatcagcc atccttcgct
10981 gcagcagtcc ggagtaacac tggccagaag actcagcctg atgtcatgtc acagaatgct
11041 agaaagctga tccagaaaaa tcttgctaca tcagctgata ctccaccaag caccgttcca
11101 ggaactggca agagtgttgc ttgtagtcct aaaaaggcag tcagagaccc taaaactggg
11161 aaagcggtgc aagagagaaa ctcctatgca gtgagtgtgt ggaagagagt gaaagccaag
11221 ttagagggcc gagatgttga tccgaatagg aggatgtcag ttgctgaaca ggttgactat
11281 gtcattaagg aagcaactaa tctagataac ttggctcagc tgtatgaagg ttggacagcc
11341 tgggtgtga
```

```
SMG1 amino acid sequence (GenBank Accession No. NP_055907.3)
                                                                 (SEQ ID NO: 8)
   1 msrrapgsrl ssgggggtk  yprswndwqp rtdsasadpd nlkysssrdr ggsssyglqp
  61 snsavvsrqr hddtrvhadi qndekggysv nggsgentyg rkslgqelrv nnvtspefts
 121 vqhgsralat kdmrksqers msysdesrls nllrritred drdrrlatvk qlkefiqqpe
 181 nklvlvkqld nilaavhdvl nesskllqel rqegacclgl lcaslsyeae kifkwifskf
 241 sssakdevkl lylcatykal etvgekkafs svmqlvmtsl qsilenvdtp ellckcvkci
 301 llvarcyphi fstnfrdtvd ilvgwhidht qkpsltqqvs gwlqslepfw vadlafsttl
 361 lgqfledmea yaedlshvas gesvdedvpp psvslpklaa llrvfstvvr sigerfspir
 421 gppiteayvt dvlyrvmrcv taanqvffse avltaanecv gvllgsldps mtihcdmvit
 481 ygldqlencq tcgtdyiisv lnlltliveq intklpssfv eklfipsskl lflryhkeke
 541 vvavahavyq avlslknipv letayklilg emtcalnnll hslqlpeacs eikheafknh
 601 vfnvdnakfv vifdlsaltt ignaknslig mwalsptvfa llsknlmivh sdlavhfpai
 661 qyavlytlys hctrhdhfis sslsssspsl fdgavistvt tatkkhfsii lnllgillkk
 721 dnlnqdtrkl lmtwaleaav lmkksetyap lfslpsfhkf ckgllantlv edvniclqac
 781 ssslhalsssl pddllqrcvd vcrvqlvhsg trirqafgkl lksipldvvl snnnhteiqe
 841 islalrshms kapsntfhpq dfsdvisfil ygnshrtgkd nwlerlfysc qrldkrdqst
 901 iprnllktda vlwqwaiwea aqftvlsklr tplgraqdtf qtiegiirsl aahtlnpdqd
 961 vsqwttadnd eghgnnqlrl vlllgylenl eklmynayeg canaltsppk virtffytnr
1021 qtcqdwltri rlsimrvgll agqpavtvrh gfdlltemkt tslsqgnele vtimmvveal
1081 celhcpeaiq giavwsssiv gknllwinsv aqqaegrfek asveyqehlc amtgvdccis
1141 sfdksvltla nagrnsaspk hslngesrkt vlskptdssp evinylgnka cecyisiadw
1201 aavqewqnai hdlkkstsst slnlkadfny ikslssfesg kfvecteqle llpgeninll
1261 aggskekidm kkllpnmlsp dprelqksie vqllrssvcl atalnpieqd qkwqsitenv
1321 vkylkqtsri aigplrlstl tvsqslpvls tlqlycssal entvsnrlst edcliplfse
1381 alrsckqhdv rpwmqalryt myqnqlleki keqtvpirsh lmelgltaak farkrgnvsl
1441 atrllaqcse vqlgktttaq dlvqhfkkls tqgqvdekwg peldiektkl lytagqstha
1501 memlsscais fcksvkaeya vaksiltlak wiqaewkeis gqlkqvyraq hqqnftglst
1561 lskniltlie lpsvntmeee ypriesestv higvgepdfi lgqlyhlssv qapevakswa
1621 alaswayrwg rkvvdnasqg egvrllprek sevqnllpdt iteeekeriy gilgqavcrp
1681 agiqdeditl qitesednee ddmvdviwrq lisscpwlse ldesategvi kvwrkvvdri
1741 fslyklscsa yftflklnag qipldeddpr lhlshrveqs tddmivmatl rllrllvkha
1801 gelrqylehg lettptapwr giipqlfsrl nhpevyvrqs icnllcrvaq dsphlilypa
1861 ivgtislsse sqasgnkfst aiptllgniq geellvsece ggsppasqds nkdepksgln
1921 edqammqdcy skivdklssa nptmvlqvqm lvaelrrvtv lwdelwlgvl lqqhmyvlrr
1981 iqqledevkr vqnnntlrke ekiaimrekh talmkpivfa lehvrsitaa paetphekwf
2041 qdnygdaien aleklktpln pakpgsswip fkeimlslqq raqkrasyil rleeispwla
2101 amtnteialp gevsardtvt ihsvggtiti lptktkpkkl lflgsdgksy pylfkgledl
2161 hlderimqfl sivntmfati nrqetprfha rhysvtplgt rsgliqwvdg atplfglykr
2221 wqqreaalqa qkaqdsyqtp qnpgivprps elyyskigpa lktvglsldv srrdwplhvm
2281 kavleelmea tppnllakel wsscttpdew wrvtqsyars tavmsmvgyi iglgdrhldn
```

-continued

```
2341 vlidmttgev vhidynvcfe kgkslrvpek vpfrmtqnie talgvtgveg vfrlsceqvl 2401 himrrgretl ltlleafvyd plvdwtagge agfagavygg ggqqaeskqs kremereitr 2461 slfssrvaei kvnwfknrde mlvvlpkldg sldeylslqe qltdveklqg klleeiefle 2521 gaegvdhpsh tlqhryseht qlqtqqravq eaiqvklnef eqwithyqaa fnnleatqla 2581 sllqeistqm dlgppsyvpa taflqnagqa hlisqceqle gevgallqqr rsvlrgcleq 2641 lhhyatvalq ypkaifqkhr ieqwktwmee licnttverc qelyrkyemq yapqppptvc 2701 qfitatemtl qryaadinsr lirgverlkq eavtvpvced qlkeiercik vflhengeeg 2761 slslasviis alctltrrnl mmegaassag eqlvdltsrd gawfleelcs msgnvtclvq 2821 llkqchlvpq dldipnpmea setvhlangv ytslqelnsn frqiifpeal rclmkgeytl 2881 esmlheldgl ieqttdgvpl qtlveslqay lrnaamglee ethahyidva rllhaqygel 2941 iqprngsvde tpkmsagqml lvafdgmfaq vetafsllve klnkmeipia wrkidiirea 3001 rstqvnffdd dnhrqvleei fflkrlqtik effrlcgtfs ktlsgsssle dqntvngpvq 3061 ivnvktlfrn scfsedqmak pikaftadfv rqlliglpnq alglticsfi salgvdiiaq 3121 veakdfgaes kvsvddlckk avehniqigk fsqlvmnrat vlassydtaw kkhdlvrrle 3181 tsisscktsl grvqlhiamf qwqhedllin rpqamsvtpp prsailtsmk kklhtlsqie 3241 tsiatvqekl aalessieqr lkwagganpa lapvlqdfea tiaerrnlvl kesqrasqvt 3301 flcsniihfe slrtrtaeal nldaalfeli krcqqmcsfa sqfnssysel elrllqrvdt 3361 glehpigsse wllsahkqlt gdmstqraiq tekeqqietv cetiqnlvdn iktvltghnr 3421 qlgdvkhllk amakdeeaal adgedvpyen svrqflgeyk swqdniqtvl ftlvqamgqv 3481 rsqehvemlq eitptlkelk tqsqsiynnl vsfasplvtd atnecsspts satyqpsfaa 3541 avrsntgqkt qpdvmsqnar kliqknlats adtppstvpg tgksvacspk kavrdpktgk 3601 avqernsyav svwkrvkakl egrdvdpnrr msvaeqvdyv ikeatnldnl aqlyegwtaw 3661 v
```

SMG5 nucleotide sequence (GenBank Accession No. NM_015327.2, nt 150-3200)

(SEQ ID NO: 9)

```
 150                     a tgagccaagg cccccccaca ggggagagca 181 gcgagcccga agcaaaagtc ctccacacta agcggcttta ccgggctgtg gtggaggctg 241 tgcatcgact tgacctcatc ctttgcaaca aaactgctta tcaagaagta ttcaaaccag 301 aaaacattag cctgaggaac aagctgcgtg agctctgcgt caagcttatg ttcctgcacc 361 cagtggacta tgggagaaag gctgaggagc tgctgtggag aaaggtatac tatgaagtta 421 tccagcttat caagactaac aaaaagcaca tccacagccg gagcactttg gaatgtgcct 481 acaggacgca cctggttgct ggtattggct tctaccagca tctccttctc tatatccagt 541 cccactacca gctggaactg cagtgctgca tcgactggac ccatgtcact gaccccctca 601 taggatgcaa gaagccagtg tctgcctcag ggaaggagag ggattgggca cagatggcat 661 gtcaccgatg tctggtgtat ctgggggatt tgtcccgata tcagaatgaa ttagctggcg 721 tagataccga gctgctagcc gagagatttt actaccaagc cctgtcagta gctcctcaga 781 ttggaatgcc cttcaatcag ctgggcaccc tggcaggcag caagtactat aatgtggaag 841 ccatgtattg ctacctgcgc tgcatccagt cagaagtgtc ctttgaggga gcctatggga 901 acctcaagcg gctgtatgac aaggcagcca aaatgtacca ccaactgaag aagtgtgaga 961 ctcggaaact gtctcctggc aaaaagcgat gtaaagacat taaaaggttg ctagtgaact 1021 ttatgtatct gcaaagcctc ctacagccca aaagcagctc cgtggactca gagctgacct
```

-continued

```
1081 cactttgcca gtcagtcctg gaggacttca acctctgcct cttctacctg ccctcctcac 1141 ccaacctcag cctggccagt gaggatgagg aggagtatga gagtggatat gctttcctcc 1201 cggaccttct catctttcaa atggtcatca tctgccttat gtgtgtgcac agcttggaga 1261 gagcaggatc caagcagtac agtgcagcca ttgccttcac cctggccctc ttttcccacc 1321 tcgtcaatca tgtcaacata cggctgcagg ctgagctgga gagggcgag aatcccgtcc 1381 cggcattcca gagtgatggc acagatgaac cagagtccaa ggaacctgtg gagaaagagg 1441 aggagccaga tcctgagcct cctcctgtaa cacccccaagt gggtgagggc agaaagagcc 1501 gtaagttctc tcgcctctcc tgtctccgcc gtcgccgcca cccacccaaa gttggtgatg 1561 acagtgacct gagtgaaggc tttgaatcgg actcaagcca tgactcagcc cgggccagtg 1621 agggctcaga cagtggctct gacaagagtc ttgaaggtgg gggaacggcc tttgatgctg 1681 aaacagactc ggaaatgaat agccaggagt cccgatcaga cttggaagat atggaggaag 1741 aggaggggac acggtcacca accctggagc cccctcgggg cagatcagag gctcccgatt 1801 ccctcaatgg cccactgggc cccagtgagg ctagcattgc cagcaatcta caagccatgt 1861 ccacccagat gttccagact aagcgctgct tccgactggc ccccaccttt agcaacctgc 1921 tcctccagcc caccaccaac cctcatacct cggccagcca caggccttgc gtcaatgggg 1981 atgtagacaa gccttcagag ccagcctctg aggagggctc tgagtcggag gggagtgagt 2041 ccagtggacg ctcctgtcgg aatgagcgca gcatccagga gaagcttcag gtcctgatgg 2101 ccgaaggtct gcttcctgct gtgaaagtct tcctggactg gcttcggacc aaccccgacc 2161 tcatcatcgt gtgtgcgcag agctctcaaa gtctgtggaa ccgcctgtct gtgttgctga 2221 atctgttgcc tgctgctggt gaactccagg agtctggcct ggccttgtgt cctgaggtcc 2281 aagatcttct tgaaggttgt gaactgcctg acctccctc tagccttctg ctcccagagg 2341 acatggctct tcgtaacctg cccccgctcc gagctgccca cagacgcttt aactttgaca 2401 cggatcggcc cctgctcagc acctagagg agtcagtggt gcgcatctgc tgcatccgca 2461 gctttggtca tttcatcgcc cgcctgcaag gcagcatcct gcagttcaac ccagaggttg 2521 gcatcttcgt cagcattgcc cagtctgagc aggagagcc gctgcagcag gcccaggcac 2581 agttccgaat ggcacaggag gaagctcgtc ggaacaggct catgagagac atggctcagc 2641 tacgacttca gctcgaagtg tctcagctgg agggcagcct gcagcagccc aaggcccagt 2701 cagccatgtc tccctacctc gtccctgaca cccaggccct ctgccaccat ctccctgtca 2761 tccgccaact ggccaccagt ggccgcttca ttgtcatcat cccaaggaca gtgatcgatg 2821 gcctggattt gctgaagaag gaacacccag gggcccggga tgggattcgg tacctggagg 2881 cagagtttaa aaaggaaac aggtacattc gctgccagaa agaggtggga aagagctttg 2941 agcggcataa gctgaagagg caggatgcag atgcctggac tctctataag atcctagaca 3001 gctgcaaaca gctgactctg gcccagggg caggtgagga ggatccgagt ggcatggtga 3061 ccatcatcac aggccttcca ctggacaacc ccagcgtgct tcaggcccc atgcaggcag 3121 ccctgcaggc cgctgcccac gccagtgtgg acatcaagaa tgttctggac ttctacaagc 3181 agtggaagga aattggttga
```

SMG5 amino acid sequence (GenBank Accession No. NP_056142.2)

(SEQ ID NO: 10)

```
  1 msqgpptges sepeakvlht krlyravvea vhrldlilcn ktayqevfkp enislrnklr 61 elcvklmflh pvdygrkaee llwrkvyyev iqliktnkkh ihsrstleca yrthlvagig 121 fyqhllllyiq shyqlelqcc idwthvtdpl igckkpvsas gkemdwaqma chrclvylgd 181 lsryqnelag vdtellaerf yyqalsvapq igmpfnqlgt lagskyynve amycylrciq
```

-continued

```
241 sevsfegayg nlkrlydkaa kmyhqlkkce trklspgkkr ckdikrllvn fmylqsllqp
301 ksssvdselt slcqsvledf nlclfylpss pnlslasede eeyesgyafl pdllifqmvi
361 iclmcvhsle ragskqysaa iaftlalfsh lvnhvnirlq aeleegenpv pafqsdgtde
421 peskepveke eepdpepppv tpqvgegrks rkfsrlsclr rrrhppkvgd dsdlsegfes
481 dsshdsaras egsdsgsdks legggtafda etdsemnsqe srsdledmee eegtrsptle
541 pprgrseapd slngplgpse asiasnlqam stqmfqtkrc frlaptfsnl llqpttnpht
601 sashrpcvng dvdkpsepas eegsesegse ssgrscrner siqeklqvlm aegllpavkv
661 fldwlrtnpd liivcaqssq slwnrlsvll nllpaagelq esglalcpev qdllegcelp
721 dlpsslllpe dmalrnlppl raahrrfnfd tdrpllstle esvvriccir sfghfiarlq
781 gsilqfnpev gifvsiaqse qesllqqaqa qfrmaqeear rnrlmrdmaq lrlqlevsql
841 egslqqpkaq samspylvpd tqalchhlpv irqlatsgrf iviiprtvid gldllkkehp
901 gardgiryle aefkkgnryi rcqkevgksf erhklkrqda dawtlykild sckqltlaqg
961 ageedpsgmv tiitglpldn psvlsgpmqa alqaaahasv diknvldfyk qwkeig
```

SMG6 nucleotide sequence (GenBank Accession No. BC064916.1, nt 296-1831)

(SEQ ID NO: 11)

```
 296                                                           atgga
 301 gacattccct gcagtggctg agaaggtcct caaggagttc caggtgttac tgcagcacag
 361 cccctctccc attggaagta cccgcatgct gcagcttatg accatcaata tgtttgcagt
 421 acacaactcc cagctgaaag actgcttctc ggaggagtgc cgctctgtga tccaggaaca
 481 agccgcagct ctgggcttgg ccatgttttc tctactggtc cgccgctgca cctgcttact
 541 taaggagtcc gccaaagctc agctgtcctc tcctgaggac caggatgacc aagacgacat
 601 caaggtgtct tcctttgtcc cggacctgaa ggagctgctc cccagtgtca agtctggtc
 661 agattggatg ctcggctacc cggacacctg aatcctcct cccacatccc tggatctgcc
 721 ctcgcatgtt gctgtggatg tatggtcgac gctggctgat ttctgtaaca tactgactgc
 781 agtgaatcag tctgaggtgc cactgtacaa ggacccggat gatgacctca cccttcttat
 841 cctggaagag gatcggcttc tctcgggctt tgtccccttg ctggctgccc ctcaggaccc
 901 ctgctacgtg gagaaaacct cggataaggt tattgcagct gactgcaaaa gggtcacagt
 961 gctgaagtat tttctggaag ccctttgtgg acaagaagag cctctgctgg cattcaaggg
1021 tggaaagtat gtgtcagtgg cacccgtccc agacaccatg ggaaaggaaa tgggaagcca
1081 agagggaaca cgactggaag atgaggagga ggatgtggtg attgaagact tgaggaaga
1141 ttcagaggct gaaggcagcg gaggcgagga tgacatcagg gagcttcggg ccaagaagct
1201 ggctctggcc aggaagatag ctgagcagca gcgtcgccag gaaaagatcc aggctgtcct
1261 ggaggaccac agtcagatga gcagatgga gctcgaaatc agacctttgt tcctcgtacc
1321 agacaccaac ggcttcattg accacctggc cagtctggcg cggctgctgg agagcaggaa
1381 gtacatcctg gtggtgcccc tcatcgtgat caatgagctg gacggcctgg ccaaggggca
1441 ggagacagac caccgggctg ggggctacgc cgtgtggta caagagaagg cccgcaagtc
1501 catcgagttc ctcgagcagc gattcgagag tcgggactct tgcctgcgag ccctgaccag
1561 ccgtggcaat gaactcgaat ccatcgcctt ccgcagtgag gacatcactg ccagctggg
1621 taacaacgat gatctcatcc tgtcctgctg cctccactac tgcaaagaca aggctaagga
1681 cttcatgccc gccagcaaag aggagccaat ccggctactg cggaggtgg tgctgttgac
1741 ggatgaccgg aacctgcgtg tgaaggcgct cacaaggaat gttcctgtac gggacatccc
```

```
1801 agccttcctc acgtgggccc aggtgggctg a
```

SMG6 amino acid sequence (GenBank Accession No. AAH64916.1)

(SEQ ID NO: 12)
```
   1 metfpavaek vlkefqvllq hspspigstr mlqlmtinmf avhnsqlkdc fseecrsviq
  61 eqaaalglam fsllvrrctc llkesakaql sspedqddqd dikvssfvpd lkellpsvkv
 121 wsdwmlgypd twnppptsld lpshvavdvw stladfcnil tavnqsevpl ykdpdddltl
 181 lileedrlls gfvpllaapq dpcyvektsd kviaadckrv tvlkyfleal cgqeepllaf
 241 kggkyvsvap vpdtmgkemg sqegtrlede eedvviedfe edseaegsgg eddirelrak
 301 klalarkiae qqrrqekiqa vledhsqmrq meleirplfl vpdtngfidh laslarlles
 361 rkyilvvpli vineldglak gqetdhragg yarvvqekar ksiefleqrf esrdsclral
 421 tsrgnelesi afrseditgq lgnnddlils cclhyckdka kdfmpaskee pirllrevvl
 481 ltddrnlrvk altrnvpvrd ipafltwaqv g
```

SMG7 nucleotide sequence (GenBank Accession No. BC036381.1, nt 119-3655)

(SEQ ID NO: 13)
```
 119                                                                at
 121 gagcctgcag agcgcgcagt acctccggca ggcagaagtc ctgaaggctg acatgacaga
 181 ttctaagctg ggtccagctg aagtctggac atccaggcag gctctgcagg acctgtacca
 241 gaaaatgcta gttaccgatt tggaatacgc tttagacaag aaagtagaac aggatctctg
 301 gaatcacgcc tttaagaatc agatcacaac actacaaggc caggcaaaga tcgagcaaa
 361 tccgaatcgg agtgaagttc aggcaaacct ttctctgttc ctagaggcag ctagtggctt
 421 ctatactcag ttattacaag aactgtgtac agtatttaat gtagatttac catgccgtgt
 481 gaagtcttcc caattgggaa ttatcagcaa taaacagacg cataccagcg ccatagtgaa
 541 gccacagtct agctcctgtt cctatatctg ccagcactgc ctcgtccacc ttggagacat
 601 tgctcgatac agaaaccaga ccagccaggc agagtcctac tataggcatg cagctcagct
 661 tgtcccctcc aatggtcagc cttataatca gttggctatc ttagcttctt ccaaaggaga
 721 ccatctgacc acaattttct actactgcag aagcattgct gtgaagttcc ctttcccagc
 781 tgcctccact aatctgcaaa aagcactttc taaagcactg gaaagccgag atgaggtgaa
 841 aaccaagtgg ggtgtttctg acttcatcaa ggcctttatt aaattccacg gtcatgtgta
 901 cctgagtaag agcttggaaa agttgagccc tcttcgagag aaattggaag aacagtttaa
 961 gaggctgcta ttccaaaaag ctttcaactc tcagcagtta gttcatgtca ctgtcattaa
1021 cctgtttcaa cttcatcacc ttcgtgactt tagcaatgaa accgagcagc acacttatag
1081 ccaagatgag cagctatgtt ggacacagtt gctggccctc tttatgtctt ttctcggcat
1141 cctgtgcaag tgtcctctac agaatgagtc tcaggaggag tcctacaatg cctatcctct
1201 tccagcagtc aaggtctcca tggactggct aagactcaga cccagggtct tcaggaggc
1261 agtggtggat gaaagacagt acatttggcc ctggttgatt tctcttctga atagtttcca
1321 tccccatgaa gaggacctct caagtattag tgcgacacca cttccagagg agtttgaatt
1381 acaaggattt ttggcattga gaccttcttt caggaacttg gattttttcca aaggtcacca
1441 gggtattaca ggggacaaag aaggccagca acgacgaata cgacagcaac gcttgatctc
1501 tataggcaaa tggattgctg ataatcagcc aaggctgatt cagtgtgaaa atgaggtagg
1561 gaaattgttg tttatcacag aaatcccaga attaatactg gaagaccca gtgaagccaa
1621 agagaacctc attctgcaag aaacatctgt gatagagtcg ctggctgcag atgggagccc
1681 agggctaaaa tcagtgctat ctacaagccg aaatttaagc aacaactgtg acacaggaga
```

-continued

```
1741 gaagccagtg gttaccttca agaaaaacat taagacacga gaagtgaaca gagaccaagg
1801 aagaagtttt cctcccaaag aggtaaaatc ccagacagaa ctaagaaaga ctccagtgtc
1861 tgaagccaga aaaacacctg taactcaaac ccaactcaa gcaagtaact cccagttcat
1921 ccccattcat caccctggag ccttccctcc tcttcccagc aggccagggt ttccgccccc
1981 aacatatgtt atcccccgc ctgtggcatt ttctatgggc tcaggttaca ccttcccagc
2041 tggtgtttct gtcccaggaa cctttcttca gcctacagct cactctccag caggaaacca
2101 ggtgcaagct gggaaacagt cccacattcc ttacagccag caacggccct ctggaccagg
2161 gccaatgaac cagggacctc aacaatcaca gccaccttcc cagcaacccc ttacatcttt
2221 accagctcag ccaacagcac agtctacaag ccagctgcag gttcaagctc taactcagca
2281 acaacaatcc cctacaaaag ctgtgccggc tttggggaaa agcccgcctc accactctgg
2341 attccagcag tatcaacagg cagatgcctc caaacagctg tggaatcccc ctcaggttca
2401 aggcccatta gggaaaatta tgcctgtgaa acagccctac taccttcaga cccaagaccc
2461 cataaaactg tttgagccgt cattgcaacc tcctgtaatg cagcagcagc ctctagaaaa
2521 aaaaaatgaag ccttttccca tggagccata taaccataat ccctcagaag tcaaggtccc
2581 agaattctac tgggattctt cctacagcat ggctgataac agatctgtaa tggcacagca
2641 agcaaacata daccgcaggg gcaaacggtc accaggaatc ttccgtccag agcaggatcc
2701 tgtacccaga atgccgtttg aggaccccaa gagctcccct ctgcttcctc cggacctgtt
2761 aaagagtctg gctgccttgg aggaagagga agagctgatt ttttctaaca ctcctgatct
2821 ttacccggct ctgctggggc ctctcgcctc tcttcctgga cgaagccttt ttaaatcctt
2881 attggagaag ccctcagagc tcatgtcaca ttcatcctct ttcctgtccc tcaccggatt
2941 ctctctcaat caggaaagat acccaaataa tagtatgttc aatgaggtat atgggaaaaa
3001 cctgacatcc agctccaaag cagaactcag tccctcaatg gcccccagg aaacatctct
3061 gtattccctt tttgaaggga ctccgtggtc tccatcactt cctgccagtt cagatcattc
3121 aacaccagcc agccagtctc ctcattcctc taacccaagc agcctaccca gctctcctcc
3181 aacacacaac cataattctg ttccattctc caattttgga cccattggga ctccagataa
3241 cagggataga aggactgcag atcggtggaa aactgataag ccagccatgg gtgggtttgg
3301 cattgattat ctctcagcaa cgtcatcctc tgagagcagt tggcatcagg ccagcactcc
3361 gagtggcacc tggacaggcc atggcccttc catggaggat tcctctgctg tcctcatgga
3421 aagcctaaag aagcaacagc atgggtcca gcagttgggg cccaaaagac agtctgaaga
3481 ggaaggaagc agcagtatct gcgtagccca cagagggccc aggccctgc ccagctgcag
3541 tctcccagcc tccactttca gagtgaaatt caaggcagca cggacatgtg cccatcaggc
3601 acagaagaaa acacgacgtc gtccattttg gaagagacga agaaaggaa aataa
```

SMG7 amino acid sequence (GenBank Accession No. AAH36381.1)

(SEQ ID NO: 14)

```
  1 mslqsaqylr qaevlkadmt dsklgpaevw tsrqalqdly qkmlvtdley aldkkveqdl
 61 wnhafknqit tlqgqaknra npnrsevqan lslfleaasg fytqllqelc tvfnvdlpcr
121 vkssqlgiis nkqthtsaiv kpqssscsyi cqhclvhlgd iaryrnqtsq aesyyrhaaq
181 lvpsngqpyn qlailassskg dhlttifyyc rsiavkfpfp aastnlqkal skalesrdev
241 ktkwgvsdfi kafikfhghv ylskslekls plrekleeqf krllfqkafn sqqlvhvtvi
301 nlfqlhhlrd fsneteqhty sqdeqlcwtq llalfmsflg ilckcplqne sqeesynayp
361 lpavkvsmdw lrlrprvfqe avvderqyiw pwlisllnsf hpheedlssi satplpeefe
```

-continued

```
421 lqgflalrps frnldfskgh qgitgdkegq qrrirqqrli sigkwiadnq prliqcenev 481 gkllfiteip eliledpsea kenlilqets vieslaadgs pglksvlsts rnlsnncdtg 541 ekpvvtfken iktrevnrdq grsfppkevk sqtelrktpv searktpvtq tptqasnsqf 601 ipihhpgafp plpsrpgfpp ptyvipppva fsmgsgytfp agvsvpgtfl qptahspagn 661 qvqagkqshi pysqqrpsgp gpmnqgpqqs qppsqqplts lpaqptaqst sqlqvqaltq 721 qqqsptkavp algkspphhs gfqqyqqada skqlwnppqv qgplgkimpv kqpyylqtqd 781 piklfepslq ppvmqqqple kkmkpfpmep ynhnpsevkv pefywdssys madnrsvmaq 841 ganidrrgkr spgifrpeqd pvprmpfedp ksspllppdl lkslaaleee eelifsntpd 901 lypallgpla slpgrslfks llekpselms hsssflsltg fslnqerypn nsmfnevygk 961 nltssskael spsmapqets lyslfegtpw spslpassdh stpasqsphs snpsslpssp 1021 pthnhnsvpf snfgpigtpd nrdrrtadrw ktdkpamggf gidylsatss sesswhqast 1081 psgtwtghgp smedssavlm eslkkqqhgv qqlgpkrqse eegsssicva hrgprplpsc 1141 slpastfrvk fkaartcahq aqkktrrrpf wkrrkkgk
```

---

We claim:

1. A method of reducing TDP-43-mediated neuronal cytotoxicity in a human subject suffering from amyotrophic lateral sclerosis (ALS), wherein the subject does not have a mutation in a SOD1 gene, comprising: administering to the subject suffering from ALS a therapeutically effective amount of a UPF1 polypeptide or a nucleic acid encoding the UPF1 polypeptide, thereby reducing the TDP-43 mediated neuronal cytotoxicity in the subject; wherein the UPF1 polypeptide comprises the amino acid sequence of SEQ ID NO:2.

2. The method of claim 1, wherein the step of administering comprises administering to the subject a composition comprising the nucleic acid encoding the UPF1 polypeptide.

3. The method of claim 1, wherein the UPF1 polypeptide or the nucleic acid encoding the UPF1 polypeptide is administered into the CNS of the subject.

* * * * *